(12) United States Patent
Amrein et al.

(10) Patent No.: US 7,652,057 B2
(45) Date of Patent: Jan. 26, 2010

(54) PYRAZOLONES AS 11B-HSD1 INHIBITORS FOR DIABETES

(75) Inventors: Kurt Amrein, Itingen (CH); Daniel Hunziker, Moehlin (CH); Bernd Kuhn, Liestal (CH); Alexander V Mayweg, Basel (CH); Werner Neidhart, Hagenthal le Bas (FR)

(73) Assignee: Hoffman-La Roche Inc., Nutley, NJ (US)

( * ) Notice: Subject to any disclaimer, the term of this patent is extended or adjusted under 35 U.S.C. 154(b) by 453 days.

(21) Appl. No.: 11/511,542

(22) Filed: Aug. 29, 2006

(65) Prior Publication Data
US 2007/0049574 A1 Mar. 1, 2007

(30) Foreign Application Priority Data
Aug. 31, 2005 (EP) ................... 05107970

(51) Int. Cl.
*A61K 31/4152* (2006.01)
*C07D 231/08* (2006.01)

(52) U.S. Cl. ................. 514/404; 548/356.1; 548/366.1; 548/371.1; 514/403

(58) Field of Classification Search ............. 548/356.1, 548/366.1, 371.1; 514/403, 404; 546/268.1, 546/268.4, 275.4
See application file for complete search history.

(56) References Cited

U.S. PATENT DOCUMENTS

| | | | |
|---|---|---|---|
| 2,731,473 A | 1/1956 | Taub et al. | |
| 5,559,244 A | 9/1996 | König et al. | |
| 5,663,365 A | 9/1997 | Yamamoto et al. | |
| 6,057,364 A | 5/2000 | Jasys et al. | |
| 6,294,567 B1 | 9/2001 | Hashizume et al. | |
| 6,972,283 B2 * | 12/2005 | Fujikura et al. | 514/27 |
| 7,084,123 B2 * | 8/2006 | Fujikura et al. | 514/27 |
| 7,368,578 B2 * | 5/2008 | Momose et al. | 548/235 |

FOREIGN PATENT DOCUMENTS

| | | |
|---|---|---|
| DE | 668 628 | 12/1938 |
| EP | 0680954 | 4/1995 |
| GB | 2 062 635 A | 5/1981 |
| WO | WO 2004/056324 | 7/2004 |
| WO | WO 2005/016877 A2 | 2/2005 |

OTHER PUBLICATIONS

Guven, A., et al., Chemical Abstracts, XP002421231 & Theochem, 499, pp. 13-19 (2000).
Heitmeier, S., et al., Journal of Chromatography B: Biomedical Applications, vol. 721, No. 1, pp. 109-125 (1999), XP004153909.
Lee, John, et al., Journal of the American Pharmaceutical Association, 25 pp. 691-694 (1936), XP008075435.
Masuzaki H. et al., Science. Dec. 7, 2001; 294(5549):2166-70.
Walker et al. 1995; J. Clin. Endocrinol. Metab. 80, 31155-3159.
P.M. Stewart and Z.S. Krozowski, Vitam. Horm. 57 (1999), pp. 249-324.
Kotelevtsev Y. et al., Proc Natl Acad Sci U S A. Dec. 23, 1997;94(26):14924-9.
Masuzaki H. et al., J Clin Invest. Jul. 2003;112(1):83-90.
Rauz S. et al., QJM. Jul. 2003;96(7):481-90.
Sandeep TC. et al., Proc Natl Acad Sci U S A. Apr. 27, 2004;101(17):6734-9.
Marsden, S. P. et al. *Synlett* 1996, 893-894.
Wallace, D. J. et al. *Tetrahedron Lett.* 2002, 49, 6987-6990.
*J. Org. Chem.* 1984, 49, 336-42.
*J. Am. Chem. Soc.* 1986, 108, 7981-4.
*Bioorg. Med. Chem.* 2004, 12, 1357-1366.
*J. Am. Chem. Soc.* 1968, 90, 2882-2889.
Alex Odermatt et al.; J Biol Chem.,1999, vol. 274, Issue 40, 28762-28770.
v. Auwers and Niemeyer in *J. Prakt. Chem.* 1925, 110, 179.
*Synthesis* 1979, 4, 283-287.
Elend et al. *Synth Comm*, 2005, 35, 657.

\* cited by examiner

*Primary Examiner*—Golam M Shameem
(74) *Attorney, Agent, or Firm*—George W. Johnston; Dennis P. Tramaloni; Samuel H. Megerditchian

(57) ABSTRACT

Compounds of formula

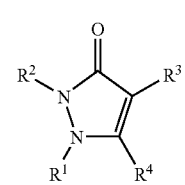

(I)

as well as pharmaceutically acceptable salts and esters thereof, wherein $R^1$ to $R^4$ have the significance given in claim 1 can be used in the form of pharmaceutical compositions.

19 Claims, No Drawings

PYRAZOLONES AS 11B-HSD1 INHIBITORS FOR DIABETES

PRIORITY TO RELATED APPLICATIONS

This application claims the benefit of European Application No. 05107970.5, filed Aug. 31, 2005, which is hereby incorporated by reference in its entirety.

FIELD OF THE INVENTION

The present invention is concerned with novel pyrazolone derivatives useful as 11b-HSD1 inhibitors (T2D).

The invention is concerned particularly with compounds of formula

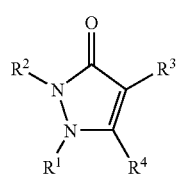

and pharmaceutically acceptable salts and esters thereof.

All documents cited or relied upon below are expressly incorporated herein by reference.

BACKGROUND

Glucocorticoids (cortisol in humans, corticosterone in mice and rats) are an important class of adrenocorticosteroids that regulate many metabolic and homeostatic processes and form a key component of the response to stress. Glucocorticoids act via intracellular glucocorticoid receptors and, in some tissues, mineralocorticoid receptors; both being nuclear transcription factors. Glucocorticoid action on target tissues depends not only on circulating steroid concentrations and the cellular expression of receptors, but also on intracellular enzymes that critically determine to which extent glucocorticoids gain access to receptors in an active forms. 11beta-hydroxysteroid dehydrogenases (11beta-HSD's) catalyze the interconversion of the principal active 11-hydroxy-glucocorticoid (Cortisol in man) and their inactive 11-keto metabolites (cortisone in man).

The enzyme 11beta-hydroxysteroid dehydrogenase type 1 (11beta-HSD1) inter-converts inactive into active glucocorticoids, thereby playing a major role in local modulation of cellular agonist concentration and thus activation of corticosteroid receptors in target tissues. In a recent study made by F. Hoffmann-La Roche differences in gene expression in lean and obese man were analyzed using gene array technology in order to identify specific changes in gene expression that might be associated with insulin resistance or altered metabolism. This study revealed that the mRNA for 11beta-HSD1 is approximately two-fold up regulated in adipose tissue in obese individuals. Moreover, overexpressing 11beta-HSD1 in adipocytes of mice led to visceral obesity and to a syndrome-X like phenotype (Masuzaki H. et al., Science. 2001 Dec. 7; 294(5549):2166-70.). Taken together, these data very strongly support an important role of 11beta-HSD1 in the induction of obesity and the impairment of glucose homeostasis and lipid parameters. Thus, selective inhibition of this enzyme could lower blood glucose levels in Type 2 diabetic patients, normalize elevated lipid parameters and/or reduce weight in obese subjects.

The first pharmacological indication that 11beta-HSD1 inhibition in man might have beneficial effects were obtained by using carbenoxolone, an anti-ulcer drug which inhibits both 11beta-HSD1 and the related enzyme 11beta-HSD2. Treatment with carbenoxolone led to an increase in insulin sensitivity indicating that that inhibition of 11beta-HSD1 may reduce cellular cortisol levels and therefore minimizing some of its deleterious effects. (Walker et al. 1995; J. Clin. Endocrinol. Metab. 80, 31155-3159).

11beta-HSD1 is expressed in many tissues including liver, adipose tissue, vascular smooth muscles, pancreas and brain. Its activity is dependent on NADP(H) and it has a relatively low affinity for its substrate (compared to 11beta-HSD2). 11beta-HSD1 in tissue homogenates and when purified is bidirectional, exhibiting both 11beta-dehydrogenase and 11beta-reductase reactions, with greater stability of the dehydrogenase activity (P. M. Stewart and Z. S. Krozowski, Vitam. Horm. 57 (1999), pp. 249-324). However, when the enzyme activity is tested in intact cells, the 11beta-reductase activity predominates, which regenerates active glucocorticoids from inert 11-keto forms. Such glucocorticoid regeneration will increase effective intracellular glucocorticoid levels and thereby amplifying glucocorticoid activity. It is this elevated cellular cortisol concentration that might lead to increased hepatic glucose production, adipocyte differentiation and insulin resistance.

Inhibition of 11beta-HSD1 should not only reduce the typical Syndrome-X/Diabetes associated symptoms, but it should also be safe and without major side effect. Studies with the unspecific inhibitor carbenoxolone highlight the importance of developing specific 11beta-HSD1 inhibitors. The inhibition of the 11beta-HSD2 enzyme is badly tolerated and results in increased blood pressure. In contrast inhibition of 11beta-HSD1 should be well tolerated since 11beta-HSD1 knockout mice were found be healthy and to resist hyperglycemia provoked by obesity or stress (Kotelevtsev Y. et al., Proc Natl Acad Sci U S A. 1997 Dec. 23; 94(26):14924-9). Similar upon starvation these mice had attenuated activation of key hepatic enzymes that are involved in gluconeogenesis. In addition, these mice had improved lipid and lipoprotein profiles suggesting that inhibition of HSD1 might be highly efficacious and safe. Recent reports indicate that 11beta-HSD1 inhibitors might also be beneficial to reduce high blood pressure (Masuzaki H. et al., J Clin Invest. 2003 July; 112(1): 83-90; Rauz S. et al., QJM. 2003 July; 96(7):481-90) to improve cognition (Sandeep T C. et al., Proc Natl Acad Sci U S A. 2004 Apr. 27; 101(17):6734-9) or to improve Alzheimer associated deficits. Taken together 11beta-HSD1 inhibition might be a safe and efficacious approach to treat symptoms of diabetes, obesity and other diseases.

SUMMARY OF THE INVENTION

In an embodiment of the present invention, provided is a compound of the formula (I):

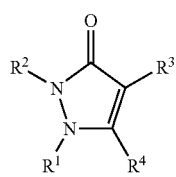

wherein

R¹ is hydrogen, alkyl, cycloalkyl, cycloalkylalkyl, aralkyl, haloalkyl, aryl, pyridinylmethyl or heterocyclyl; and with the proviso that in case R¹ is hydrogen then R³ is adamantanyl or adamantanyl substituted with one to three substituents independently selected from alkyl, hydroxy, halogen and haloalkyl;

R² is hydrogen, alkyl, cycloalkyl, aryl, aralkyl, benzothiazolyl, bicyclo(2.2.1)heptyl or bicyclo(2.2.2)octyl, wherein bicyclo(2.2.1)heptyl and bicyclo(2.2.2)octyl are optionally substituted with one to three substituents independently selected from alkyl, hydroxy, halogen and haloalkyl;
  or R¹ and R² together with the nitrogen atoms to which they are attached form pyrazolidine, hexahydro-pyridazine, (1,2)diazepane or 2,3,4,5, tetrahydro-1H-benzo(c)(1,2)diazepine, wherein pyrazolidine, hexahydro-pyridazine, (1,2)diazepane and 2,3,4,5, tetrahydro-1H-benzo(c)(1,2)diazepine are optionally substituted with one to three alkyl groups;
  or R¹ and R⁴ together form —(CH₂)ₘ—;
  m is 3, 4, 5 or 6;

R³ is cyclopropyl, arylcyclopropyl, isopropyl, tert.-butyl, adamantanyl or bicyclo(2.2.2)octyl, wherein adamantanyl and bicyclo(2.2.2)octyl are optionally substituted with one to three substituents independently selected from alkyl, hydroxy, halogen and haloalkyl;

R⁴ is hydrogen, alkyl, cycloalkyl, aryloxyalkyl, alkylcarbonylaminoaryloxyalkyl, alkyloxyalkyl, aryl, aralkyl, haloalkyl or halocycloalkyl;
  or R³ and R⁴ together form —(CH₂)ₙ—;
  n is 3, 4, 5 or 6;

and pharmaceutically acceptable salts and esters thereof; with the proviso that in case R³ and R⁴ together form —(CH₂)ₙ— then R¹ is alkyl and R² is not hydrogen or alkyl; and with the proviso that in case R⁴ is hydrogen or alkyl then R³ is not isopropyl; and with the proviso that 3-cyclopropyl-4-isopropyl-2-methyl-1-phenyl-3-pyrazolin-5-one; 1,2-dihydro-5-methyl-4-tricyclo(3.3.1.13,7)dec-1-yl-3H-pyrazol-3-one; 1,2,3,4,6,7,8,9-octahydro-10H,12H-indazolo(1,2-a)indazole-10,12-dione; 1,2,4,5,6,7-hexahydro-1-methyl-2-phenyl-3H-indazol-3-one; 1,4,5,6-tetrahydro-1-methyl-2-phenyl-3(2H)-cyclopentapyrazolone; 1,4,5,6-tetrahydro-1-benzyl-2-phenyl-3(2H)-cyclopentapyrazolone; 1,4,5,6-tetrahydro-1-ethyl-2-(4-methyl)-phenyl-3(2H)-cyclopentapyrazolone; 1,4,5,6-tetrahydro-1-ethyl-2-phenyl-3(2H)-cyclopentapyrazolone; and 1,4,5,6,7,8-hexahydro-1-methyl-2-phenyl-3(2H)-cycloheptapyrazolone are excluded.

In another embodiment of the present invention, provided is a process for the preparation of a compound of formula (I)

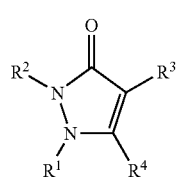
(I)

comprising one of the following reactions:

reacting a compound according to formula

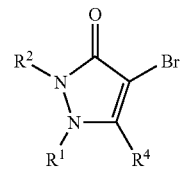

in the presence of a compound of formula

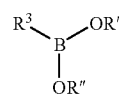
III in order to obtain a compound of formula I; or reacting a compound of formula

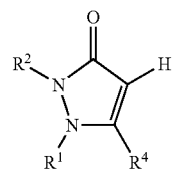
II in the presence of R³—OH in order to obtain a compound of formula I;

wherein R¹ to R⁴ are as defined above and R' and R'' are hydrogen or R' and R'' form together —(CH₂)₂— or —(CH₂)₃—.

In a further embodiment of the present invention, provided is a pharmaceutical composition, comprising a therapeutically effective amount of a compound according to formula I and a therapeutically inert carrier.

In a yet another embodiment of the present invention, provided is a method for the treatment and prophylaxis of diabetes, obesity, eating disorders, dyslipidemiae and hypertension, comprising the step of administering a therapeutically effective amount of a compound according to formula I to a patient in need thereof.

DETAILED DESCRIPTION

The compounds of formula I and their pharmaceutically acceptable salts and esters are novel and have valuable pharmacological properties. In particular they are 11b-HSD1 inhibitors (T2D) and they display selectivity against the related 11beta-HSD2 enzyme. Therefore the compounds which are specific 11beta-HSD1 inhibitors (T2D) represent an approach to e.g. lower blood glucose levels and normalize lipid parameters in Type 2 diabetic patients by modulating the local concentration of the active glucocorticoid cortisol in target tissue (liver, adipose tissue).

The compounds of the present invention can be used in the prophylaxis and/or treatment of metabolic disorders, obesity, dyslipidemiae, hypertension and/or diabetes, particularly diabetes Type II.

The compounds of this invention can further be used in the prophylaxis and/or treatment of high ocular eye pressure, cognition, Alzheimer and/or neurodegeneration.

Further, the compounds of this invention can be used for promoting wound healing, particularly by topical application. Moreover, the compounds of the present invention can be used to improve cognitive impairment, particularly impairment developed with age, and improvement of memory.

Further, the compounds of this invention can be used in the prophylaxis and/or treatment of atherosclerosis.

Embodiments of the present invention are the compounds of formula I and their aforementioned salts and esters per se and their use as therapeutically active substances, a process for the manufacture of the said compounds, intermediates, pharmaceutical compositions, medicaments containing the said compounds, their pharmaceutically acceptable salts and esters, the use of the said compounds, esters and salts for the prophylaxis and/or therapy of illnesses, especially in the treatment or prophylaxis of eating disorders, obesity, dyslipidemiae, hypertension and/or diabetes, particularly diabetes Type II, and the use of the said compounds, salts and esters for the production of medicaments for the treatment or prophylaxis of metabolic disorders, obesity, dyslipidemiae, hypertension and/or diabetes, particularly diabetes Type II.

The compounds of the present invention can further be combined with PPAR (alpha, gamma, delta) agonists, DHEA (dehydroepiandrosterone), DPPIV inhibitors, insulin and/or lipase inhibitors, particularly orlistat.

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl", alone or in combination, signifies a cycloalkyl ring with 3 to 8 carbon atoms and preferably a cycloalkyl ring with 3 to 6 carbon atoms. Examples of $C_3$-$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec. butoxy and tert.butoxy, preferably methoxy and ethoxy and most preferred methoxy.

The term "haloalkyl", alone or in combination, signifies an alkyl group as previously defined, wherein one to five hydrogen atoms are substituted by halogen, preferably fluoro. Preferred examples are pentafluoroethyl and particularly trifluoromethyl.

The term "halocycloalkyl", alone or in combination, signifies an cycloalkyl group as previously defined, wherein one to five hydrogen atoms are substituted by halogen, preferably fluoro. Preferred examples are 2,2-difluoro-cyclopropyl and 3,3-difluoro-cyclobutyl.

The term "hydroxyalkyl", alone or in combination, signifies an alkyl group as defined before, wherein one or more hydrogen atoms, preferably one hydrogen atom is replaced by a hydroxy group. Examples of hydroxyalkyl are hydroxymethyl and hydroxyethyl.

The term "aryl", alone or in combination, signifies a phenyl or naphthyl group, preferably a phenyl group which optionally carries one or more substituents, preferably one to three, each independently selected from halogen, trifluoromethyl, trifluoromethoxy, amino, alkyl, alkoxy, alkylcarbonyl, cyano, carbamoyl, alkoxycarbamoyl, methylendioxy, carboxy, alkoxycarbonyl, aminocarbonyl, alkylaminocarbonyl, dialkylaminocarbonyl, hydroxy, nitro, alkyl-$SO_2$—, amino-$SO_2$—, cycloalkyl and the like. Examples are phenyl or naphthyl, particularly phenyl optionally substituted with one to three, preferably one or two substituents independently selected from alkyl, halogen, alkoxy, trifluoromethoxy, nitro and trifluoromethyl.

The term "aryloxy", alone or in combination, signifies a aryl-O— group in which the term "aryl" has the previously given significance.

The term "heterocyclyl", alone or in combination signifies a saturated, partially unsaturated or aromatic 5- to 10-membered heterocycle which contains one or more hetero atoms selected from nitrogen, oxygen and sulphur. If desired, it can be substituted on one or more carbon atoms e.g. by halogen, alkyl, alkoxy, oxo etc. and/or on a secondary nitrogen atom (i.e. —NH—) by alkyl, cycloalkyl, aralkoxycarbonyl, alkanoyl, phenyl or phenylalkyl or on a tertiary nitrogen atom (i.e. =N—) by oxido, with halogen, alkyl, cycloalkyl and alkoxy being preferred. Examples of such heterocyclyl groups are pyrrolidinyl, piperidinyl, piperazinyl, morpholinyl, thiomorpholinyl, pyrazoyl, imidazoyl (e.g. imidazol-4-yl and 1-benzyloxycarbonyl-imidazol-4-yl), pyrazoyl, pyridyl, pyrazinyl, pyrimidinyl, hexahydro-pyrimidinyl, furyl, thienyl, thiazolyl, oxazolyl, indolyl (e.g. 2-indolyl), quinolyl (e.g. 2-quinolyl, 3-quinolyl and 1-oxido-2-quinolyl), isoquinolyl (e.g. 1-isoquinolyl and 3-isoquinolyl), tetrahydroquinolyl (e.g. 1,2,3,4-tetrahydro-2-quinolyl), 1,2,3,4-tetrahydroisoquinolyl (e.g. 1,2,3,4-tetrahydro-1-oxo-isoquinolyl) and quinoxalinyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —$NH_2$, methylamino, ethylamino, dimethylamino, diethylamino, methyl-ethylamino, pyrrolidin-1-yl or piperidino etc., preferably primary amino, dimethylamino and diethylamino and particularly dimethylamino.

The term "halogen", alone or in combination, signifies fluorine, chlorine, bromine or iodine and preferably fluorine, chlorine or bromine.

The term "carbonyl", alone or in combination, signifies the —C(O)— group.

The term "aralkyl", alone or in combination, signifies the aryl-alkyl group, wherein the terms "aryl" and "alkyl" are as previously defined.

The term "oxy", alone or in combination, signifies the —O— group.

The term "nitro", alone or in combination signifies the —$NO_2$ group.

The term "cyano", alone or in combination signifies the group —CN.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Pharmaceutically acceptable esters" means that compounds of general formula (I) may be derivatized at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The compounds of formula I can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

The term "asymmetric carbon atom" (C*) means a carbon atom with four different substituents. According to the Cahn-Ingold-Prelog Convention the asymmetric carbon atom can be of the "R" or "S" configuration.

Preferred are the compounds of formula I and pharmaceutically acceptable salts thereof, particularly the compounds of formula I.

Preferred are those compounds of formula I, wherein $R^1$ is hydrogen, alkyl, cycloalkyl, cycloalkylalkyl, aralkyl, haloalkyl, aryl or heterocyclyl; and with the proviso that in case $R^1$ is hydrogen then $R^3$ is adamantanyl or adamantanyl substituted with one to three substituents independently selected from alkyl, hydroxy, halogen and haloalkyl;

$R^2$ is hydrogen, alkyl, cycloalkyl, aryl, aralkyl, bicyclo(2.2.1)heptyl or bicyclo(2.2.2)octyl, wherein bicyclo(2.2.1)heptyl and bicyclo(2.2.2)octyl are optionally substituted with one to three substituents independently selected from alkyl, hydroxy, halogen and haloalkyl;

or $R^1$ and $R^2$ together with the nitrogen atoms to which they are attached form pyrazolidine, hexahydro-pyridazine, (1,2)diazepane or 2,3,4,5, tetrahydro-1H-benzo(c)(1,2) diazepine, wherein pyrazolidine, hexahydro-pyridazine, (1,2)diazepane and 2,3,4,5, tetrahydro-1H-benzo(c)(1, 2)diazepine are optionally substituted with one to three alkyl groups;

or $R^1$ and $R^4$ together form —$(CH_2)_m$—;

m is 3, 4, 5 or 6;

$R^4$ is hydrogen, alkyl, cycloalkyl, aryloxyalkyl, alkylcarbonylaminoaryloxyalkyl, alkyloxyalkyl, aryl, aralkyl or haloalkyl;

or $R^3$ and $R^4$ together form —$(CH_2)_n$—; and n is 3, 4, 5 or 6.

Further preferred are compounds of formula I, wherein $R^3$ is cyclopropyl, isopropyl, tert-butyl, adamantanyl or 4-methyl-bicyclo(2.2.2)octyl. Particularly preferred are those compounds of formula I, wherein $R^3$ is cyclopropyl or adamantanyl. Very preferred are those compounds according to formula I, wherein $R^3$ is adamantanyl.

Preferred are compounds of formula I, wherein $R^4$ is alkyl, cycloalkyl, aryloxyalkyl, alkylcarbonylaminoaryloxyalkyl, alkyloxyalkyl, aryl, aralkyl or haloalkyl.

Moreover, preferred are compounds according to formula I, wherein $R^4$ is cyclopropyl, cyclobutyl, 1-methyl-cyclopropyl, tert-butyl, 2,2-dimethyl-cyclopropyl, fluoro-phenoxymethyl, fluoro-phenyl-ethyl, chloro-phenoxymethyl, dichlorophenoxymethyl, isopropoxymethyl, methyl, hydrogen or trifluoromethyl. Particularly preferred are the compounds of formula I, wherein $R^4$ is cyclopropyl, cyclobutyl, 1-methyl-cyclopropyl, tert-butyl, 2,2-dimethyl-cyclopropyl or 4-fluoro-phenoxymethyl.

Another preferred aspect of the present invention are the compounds of formula I, wherein $R^3$ is adamantanyl and $R^4$ is hydrogen, methyl or cyclopropyl.

Preferred are compounds of formula I, wherein $R^1$ is alkyl, cycloalkyl, cycloalkylalkyl, aralkyl, haloalkyl, aryl or heterocyclyl.

The term "heterocyclyl" as used in the definition of $R^1$ means preferably pyridinyl and particularly pyridin-2-yl.

Further preferred are those compounds of formula I, wherein $R^1$ is hydrogen, methyl, ethyl, isopropyl, cyclopropyl, benzyl, cyclopropylmethyl, phenyl, pyridinyl or fluorophenyl. Particularly preferred are the compounds of formula I, wherein $R^1$ is methyl or phenyl.

Preferred are compounds of formula I, wherein $R^1$ and $R^2$ together with the nitrogen atoms to which they are attached form pyrazolidine, hexahydro-pyridazine or (1,2)diazepane.

Further preferred are those compounds of formula I, wherein $R^1$ and $R^4$ together form —$(CH_2)_m$—, wherein m is 4 or 5.

Additionally preferred are compounds according to formula I, wherein $R^3$ and $R^4$ together form —$(CH_2)_n$—, wherein n is 4 or 5.

Preferred are compounds of formula I, wherein $R^2$ is alkyl, cycloalkyl, aryl, aralkyl, bicyclo(2.2.1)heptyl or bicyclo (2.2.2)octyl, wherein bicyclo(2.2.1)heptyl and bicyclo(2.2.2) octyl are optionally substituted with one to three substituents independently selected from alkyl, hydroxy, halogen and haloalkyl.

Another preferred aspect of the present invention are compounds of formula I, wherein $R^2$ is hydrogen, methyl, ethyl, 1,7,7-trimethyl-bicyclo(2.2.1)hept-2-yl, naphthyl, phenyl or substituted phenyl, wherein the substituted phenyl is phenyl substituted with one to three substituents, preferably one or two substituents, independently selected from fluoro, chloro, trifluoromethyl and hydroxy. Particularly preferred are those compounds of formula I, wherein $R^2$ is methyl, fluoro-phenyl, chloro-phenyl or trifluoromethyl-phenyl.

Preferred are compounds of formula I, wherein m is 3, 4 or 5. Particularly preferred are those, wherein m is 4 or 5.

Preferred are compounds of formula I, wherein n is 3, 4 or 5. Particularly preferred are those, wherein n is 4 or 5.

Examples of preferred compounds of formula (I) are:

4,5-Dicyclopropyl-1-methyl-2-phenyl-1,2-dihydro-pyrazol-3-one;
4,5-Dicyclopropyl-2-(2-fluoro-phenyl)-1-methyl-1,2-dihydro-pyrazol-3-one;
4,5-Dicyclopropyl-2-(4-fluoro-phenyl)-1-methyl-1,2-dihydro-pyrazol-3-one;
4,5-Dicyclopropyl-2-(2,4-difluoro-phenyl)-1-methyl-1,2-dihydro-pyrazol-3-one;
4,5-Dicyclopropyl-2-(3-fluoro-phenyl)-1-methyl-1,2-dihydro-pyrazol-3-one;
2-(2-Chloro-phenyl)-4,5-dicyclopropyl-1-methyl-1,2-dihydro-pyrazol-3-one;
2-(3-Chloro-phenyl)-4,5-dicyclopropyl-1-methyl-1,2-dihydro-pyrazol-3-one;
4,5-Dicyclopropyl-1-methyl-2-(2-trifluoromethyl-phenyl)-1,2-dihydro-pyrazol-3-one;
4,5-Dicyclopropyl-1-methyl-2-(3-trifluoromethyl-phenyl)-1,2-dihydro-pyrazol-3-one;
4,5-Dicyclopropyl-2-(4-fluoro-2-trifluoromethyl-phenyl)-1-methyl-1,2-dihydro-pyrazol-3-one;
4,5-Dicyclopropyl-2-(2-methoxy-phenyl)-1-methyl-1,2-dihydro-pyrazol-3-one;
4,5-Dicyclopropyl-1-methyl-2-naphthalen-1-yl-1,2-dihydro-pyrazol-3-one;
4,5-Dicyclopropyl-1-ethyl-2-(4-fluoro-phenyl)-1,2-dihydro-pyrazol-3-one;
4,5-Dicyclopropyl-1-ethyl-2-(3-fluoro-phenyl)-1,2-dihydro-pyrazol-3-one;
2-(2-Chloro-phenyl)-4,5-dicyclopropyl-1-ethyl-1,2-dihydro-pyrazol-3-one;
2-(3-Chloro-phenyl)-4,5-dicyclopropyl-1-ethyl-1,2-dihydro-pyrazol-3-one;
4,5-Dicyclopropyl-1-ethyl-2-(2-trifluoromethyl-phenyl)-1,2-dihydro-pyrazol-3-one;
Benzyl-4,5-dicyclopropyl-2-(2-trifluoromethyl-phenyl)-1,2-dihydro-pyrazol-3-one;
4,5-Dicyclopropyl-1-cyclopropylmethyl-2-(2-trifluoromethyl-phenyl)-1,2-dihydro-pyrazol-3-one;
Benzyl-4,5-dicyclopropyl-1-methyl-1,2-dihydro-pyrazol-3-one;
2,3-Dicyclopropyl-6,7,8,9-tetrahydro-5H-pyrazolo[1,2-a][1,2]diazepin-1-one;
5-Cyclobutyl-4-cyclopropyl-1-methyl-2-phenyl-1,2-dihydro-pyrazol-3-one;
5-Cyclobutyl-4-cyclopropyl-1-methyl-2-(2-trifluoromethyl-phenyl)-1,2-dihydro-pyrazol-3-one;
Cyclopropyl-1-methyl-5-(1-methyl-cyclopropyl)-2-(2-trifluoromethyl-phenyl)-1,2-dihydro-pyrazol-3-one;
tert-Butyl-4-cyclopropyl-1-methyl-2-(2-trifluoromethyl-phenyl)-1,2-dihydro-pyrazol-3-one;
Cyclopropyl-5-(2,2-dimethyl-cyclopropyl)-1-methyl-2-(2-trifluoromethyl-phenyl)-1,2-dihydro-pyrazol-3-one;
3-Cyclopropyl-1-phenyl-4,5,6,7-tetrahydro-pyrazolo[1,5-a]pyridin-2-one;
4-Cyclopropyl-5-(4-fluoro-phenoxymethyl)-1-methyl-2-phenyl-1,2-dihydro-pyrazol-3-one;
4-Cyclopropyl-5-(4-fluoro-phenoxymethyl)-2-(4-fluoro-phenyl)-1-methyl-1,2-dihydro-pyrazol-3-one;
N-{4-[4-Cyclopropyl-1-(4-fluoro-phenyl)-2-methyl-5-oxo-2,5-dihydro-1H-pyrazol-3-ylmethoxy]-phenyl}-acetamide;
N-{4-[4-Cyclopropyl-1-(2-fluoro-phenyl)-2-methyl-5-oxo-2,5-dihydro-1H-pyrazol-3-ylmethoxy]-phenyl}-acetamide;
4-Cyclopropyl-5-(4-fluoro-phenoxymethyl)-2-(2-fluoro-phenyl)-1-methyl-1,2-dihydro-pyrazol-3-one;
4-Cyclopropyl-2-(4-fluoro-phenyl)-5-[2-(4-fluoro-phenyl)-ethyl]-1-methyl-1,2-dihydro-pyrazol-3-one;
4-Cyclopropyl-2-(2-fluoro-phenyl)-5-[2-(4-fluoro-phenyl)-ethyl]-1-methyl-1,2-dihydro-pyrazol-3-one;
4-Cyclopropyl-1-ethyl-5-(4-fluoro-phenoxymethyl)-2-(4-fluoro-phenyl)-1,2-dihydro-pyrazol-3-one;
5-(4-Chloro-phenoxymethyl)-4-isopropyl-1-methyl-2-phenyl-1,2-dihydro-pyrazol-3-one;
5-(2,4-Dichloro-phenoxymethyl)-4-isopropyl-1-methyl-2-phenyl-1,2-dihydro-pyrazol-3-one;
5-(4-Fluoro-phenoxymethyl)-4-isopropyl-1-methyl-2-phenyl-1,2-dihydro-pyrazol-3-one;
5-(2-Chloro-phenoxymethyl)-4-isopropyl-1-methyl-2-phenyl-1,2-dihydro-pyrazol-3-one;
Isopropoxymethyl-4-isopropyl-1-methyl-2-phenyl-1,2-dihydro-pyrazol-3-one;
Ethyl-2-phenyl-1,2,4,5,6,7-hexahydro-indazol-3-one;
Methyl-2-phenyl-1,4,5,6,7,8-hexahydro-2H-cycloheptapyrazol-3-one;
Methyl-2-(1,7,7-trimethyl-bicyclo[2.2.1]hept-2-yl)-1,2,4,5,6,7-hexahydro-indazol-3-one;
2-(2,4-Dichloro-phenyl)-1-methyl-1,2,4,5,6,7-hexahydro-indazol-3-one;
Methyl-2-(2-trifluoromethyl-phenyl)-1,4,5,6,7,8-hexahydro-2H-cycloheptapyrazol-3-one;
4-tert-Butyl-1,5-dimethyl-2-phenyl-1,2-dihydro-pyrazol-3-one;
4-tert-Butyl-2,5-dimethyl-1-phenyl-1,2-dihydro-pyrazol-3-one;
4-Adamantan-1-yl-5-methyl-1,2-dihydro-pyrazol-3-one;
Adamantan-1-yl-3-methyl-6,7-dihydro-5H-pyrazolo[1,2-a]pyrazol-1-one;
Adamantan-1-yl-3-methyl-5,6,7,8-tetrahydro-pyrazolo[1,2-a]pyridazin-1-one;
Adamantan-1-yl-3-methyl-6,7,8,9-tetrahydro-5H-pyrazolo[1,2-a][1,2]diazepin-1-one;
Adamantan-1-yl-3-cyclopropyl-6,7-dihydro-5H-pyrazolo[1,2-a]pyrazol-1-one;
Adamantan-1-yl-1,2,5-trimethyl-1,2-dihydro-pyrazol-3-one;
Adamantan-1-yl-1-benzyl-2,5-dimethyl-1,2-dihydro-pyrazol-3-one;
Adamantan-1-yl-1-isopropyl-5-methyl-1,2-dihydro-pyrazol-3-one;
Adamantan-1-yl-5-methyl-2-phenyl-1,2-dihydro-pyrazol-3-one;
4-Adamantan-1-yl-1,5-dimethyl-2-phenyl-1,2-dihydro-pyrazol-3-one;
4-Adamantan-1-yl-2,5-dimethyl-1-phenyl-1,2-dihydro-pyrazol-3-one;
4-Adamantan-1-yl-5-methyl-1-phenyl-1,2-dihydro-pyrazol-3-one;
4-Adamantan-1-yl-1-phenyl-1,2-dihydro-pyrazol-3-one;
4-Adamantan-1-yl-2-methyl-1-phenyl-1,2-dihydro-pyrazol-3-one;
4-Adamantan-1-yl-5-methyl-1-pyridin-2-yl-1,2-dihydro-pyrazol-3-one;
4-Adamantan-1-yl-2,5-dimethyl-1-pyridin-2-yl-1,2-dihydro-pyrazol-3-one;

4-Adamantan-1-yl-1-(4-fluoro-phenyl)-2,5-dimethyl-1,2-dihydro-pyrazol-3-one;
4-Adamantan-1-yl-2-ethyl-5-methyl-1-phenyl-1,2-dihydro-pyrazol-3-one;
Adamantan-1-yl-5,6,7,8-tetrahydro-4H-pyrazolo[1,5-a]azepin-2-one;
Adamantan-1-yl-1-methyl-5,6,7,8-tetrahydro-4H-pyrazolo[1,5-a]azepin-2-one;
Adamantan-1-yl-1-methyl-4,5,6,7-tetrahydro-pyrazolo[1,5-a]pyridin-2-one;
Adamantan-1-yl-1-ethyl-4,5,6,7-tetrahydro-pyrazolo[1,5-a]pyridin-2-one;
1,5-Dimethyl-4-(4-methyl-bicyclo[2.2.2]oct-1-yl)-2-phenyl-1,2-dihydro-pyrazol-3-one;
2,5-Dimethyl-4-(4-methyl-bicyclo[2.2.2]oct-1-yl)-1-phenyl-1,2-dihydro-pyrazol-3-one.

Examples of particularly preferred compounds of formula (I) are:
4,5-Dicyclopropyl-2-(2-fluoro-phenyl)-1-methyl-1,2-dihydro-pyrazol-3-one;
2-(2-Chloro-phenyl)-4,5-dicyclopropyl-1-methyl-1,2-dihydro-pyrazol-3-one;
4,5-Dicyclopropyl-1-methyl-2-(2-trifluoromethyl-phenyl)-1,2-dihydro-pyrazol-3-one;
Cyclobutyl-4-cyclopropyl-1-methyl-2-(2-trifluoromethyl-phenyl)-1,2-dihydro-pyrazol-3-one;
Cyclopropyl-1-methyl-5-(1-methyl-cyclopropyl)-2-(2-trifluoromethyl-phenyl)-1,2-dihydro-pyrazol-3-one;
tert-Butyl-4-cyclopropyl-1-methyl-2-(2-trifluoromethyl-phenyl)-1,2-dihydro-pyrazol-3-one;
Cyclopropyl-5-(2,2-dimethyl-cyclopropyl)-1-methyl-2-(2-trifluoromethyl-phenyl)-1,2-dihydro-pyrazol-3-one;
4-Cyclopropyl-5-(4-fluoro-phenoxymethyl)-2-(2-fluoro-phenyl)-1-methyl-1,2-dihydro-pyrazol-3-one;
2-Adamantan-1-yl-3-methyl-6,7-dihydro-5H-pyrazolo[1,2-a]pyrazol-1-one;
4-Adamantan-1-yl-2,5-dimethyl-1-phenyl-1,2-dihydro-pyrazol-3-one; and
3-Adamantan-1-yl-1-methyl-4,5,6,7-tetrahydro-pyrazolo[1,5-a]pyridin-2-one.

Examples of further preferred compounds of formula (I) are:
4,5-Dicyclopropyl-2-(2,3-dichloro-phenyl)-1-methyl-1,2-dihydro-pyrazol-3-one;
Benzyl-4,5-dicyclopropyl-2-(2,4-difluoro-phenyl)-1,2-dihydro-pyrazol-3-one;
4,5-Dicyclopropyl-2-(2,4-difluoro-phenyl)-1-(2-fluoro-benzyl)-1,2-dihydro-pyrazol-3-one;
4,5-Dicyclopropyl-2-(2,4-difluoro-phenyl)-1-(4-fluoro-benzyl)-1,2-dihydro-pyrazol-3-one;
4,5-Dicyclopropyl-2-(3-fluoro-2-trifluoromethyl-phenyl)-1-methyl-1,2-dihydro-pyrazol-3-one;
Benzyl-4,5-dicyclopropyl-2-(2,5-difluoro-phenyl)-1,2-dihydro-pyrazol-3-one;
4,5-Dicyclopropyl-2-(2,5-difluoro-phenyl)-1-methyl-1,2-dihydro-pyrazol-3-one;
4,5-Dicyclopropyl-2-(2-methanesulfonyl-phenyl)-1-methyl-1,2-dihydro-pyrazol-3-one;
4,5-Dicyclopropyl-1-methyl-2-(2-trifluoromethoxy-phenyl)-1,2-dihydro-pyrazol-3-one;
4,5-Dicyclopropyl-1-(2,4-difluoro-benzyl)-2-(2,5-difluoro-phenyl)-1,2-dihydro-pyrazol-3-one;
4,5-Dicyclopropyl-2-(2,4-difluoro-phenyl)-1-(3,3,3-trifluoro-propyl)-1,2-dihydro-pyrazol-3-one;
4,5-Dicyclopropyl-2-(2,4-difluoro-phenyl)-1-pyridin-2-ylmethyl-1,2-dihydro-pyrazol-3-one;
4,5-Dicyclopropyl-1-methyl-2-o-tolyl-1,2-dihydro-pyrazol-3-one;
Benzothiazol-2-yl-4,5-dicyclopropyl-1-methyl-1,2-dihydro-pyrazol-3-one;
4,5-Dicyclopropyl-2-(2,3-dimethyl-phenyl)-1-methyl-1,2-dihydro-pyrazol-3-one;
4,5-Dicyclopropyl-2-(2-ethyl-phenyl)-1-methyl-1,2-dihydro-pyrazol-3-one;
4,5-Dicyclopropyl-2-(2,5-dichloro-phenyl)-1-methyl-1,2-dihydro-pyrazol-3-one;
4,5-Dicyclopropyl-2-(2-fluoro-3-methyl-6-trifluoromethyl-phenyl)-1-methyl-1,2-dihydro-pyrazol-3-one;
Cyclopropyl-1-methyl-5-trifluoromethyl-2-(2-trifluoromethyl-phenyl)-1,2-dihydro-pyrazol-3-one;
Cyclopropyl-5-(2,2-difluoro-cyclopropyl)-1-methyl-2-(2-trifluoromethyl-phenyl)-1,2-dihydro-pyrazol-3-one;
Cyclopropyl-5-(3,3-difluoro-cyclobutyl)-1-methyl-2-(2-trifluoromethyl-phenyl)-1,2-dihydro-pyrazol-3-one;
4,5-Dicyclopropyl-2-(2,4-difluoro-phenyl)-1-(2,2,2-trifluoro-ethyl)-1,2-dihydro-pyrazol-3-one; and
4,5-Dicyclopropyl-2-(2,2-dimethyl-propyl)-1-methyl-1,2-dihydro-pyrazol-3-one.

Processes for the manufacture of compounds of formula I are an embodiment of the invention.

The preparation of compounds of formula I of the present invention may be carried out in sequential or convergent synthetic routes. Syntheses of the invention are shown in the following Schemes. The skills required for carrying out the reaction and purification of the resulting products are known to those persons skilled in the art. The substituents and indices used in the following description of the processes have the significance given above unless indicated to the contrary.

Compounds of formula I are readily accessible by reaction of compounds of formula II in the following manner: For compounds of formula Ia where $R^3$ means cyclopropyl or arylcyclopropyl, compound II is first brominated with N-bromosuccinimide and then reacted with the appropriate cyclopropylboronic acid or ester or arylcyclopropylboronic acid or ester in the presence of a suitable palladium catalyst, phosphine ligand, such as tricyclohexylphosphine, and base (see also Marsden, S. P. et al. *Synlett* 1996, 893-894 and Wallace, D. J. et al. *Tetrahedron Lett.* 2002, 49, 6987-6990) (Scheme 1). The boronic acids or esters are either commercially available or prepared according to or in analogy to literature procedures known to those persons skilled in the art. R means e.g. hydrogen or both R substituents of compound III together form —(CH$_2$)$_2$— or —(CH$_2$)$_3$—.

Scheme 1

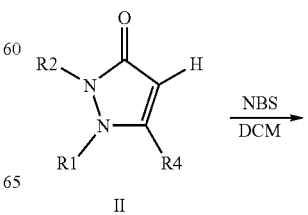

II

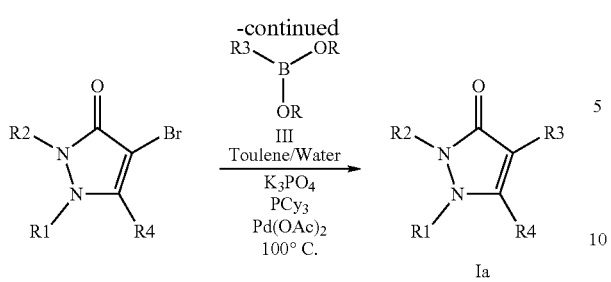

For compounds of formula Ib where $R^3$ means adamantanyl, bicyclo(2.2.2)octyl or tert.-butyl compound II is alkylated directly using a Lewis acid such as boron trifluoride diethyletherate or tin tetrachloride in a solvent such as pentane or dichloroethane and the corresponding tertiary alcohols of formula IV, as indicated in scheme 2. For compounds of formula Ic where $R^1$ and $R^2$ together with the nitrogen atoms to which they are attached form a heterocyclic ring (in particular pyrazolidine, hexahydro-pyridazine, (1,2)diazepane or 2,3,4,5, tetrahydro-1H-benzo(c)(1,2)diazepine, optionally substituted with alkyl groups), compound Ib (where $R^1$ and $R^2$=H) is alkylated in a one step procedure using a di-haloalkane of formula Br—Y—Br using thermal or microwave assisted conditions with one equivalent of base. Alternatively the annulation can be carried out using a compound of formula Br—Y—Br via a two step process by alkylation on either nitrogen atom 1 or nitrogen atom 2 followed by ring closure using basic conditions or palladium or copper-mediated coupling reactions.

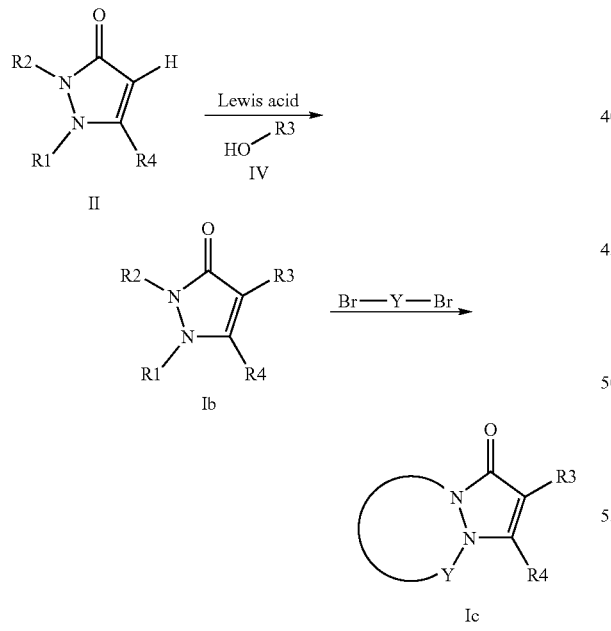

Compounds of formula Id where $R^3$ and $R^4$ together form —$(CH_2)_n$—, wherein n is 3, 4, 5 or 6, or where $R^3$ means isopropyl are derived from compounds of formula V in a two step process via condensation with the appropriately substituted hydrazine of formula VI in acetic acid at elevated temperature, followed by alkylation of the product with a suitable halide of formula VII under thermal or microwave assisted conditions in DMF, as indicated in scheme 3. Compounds of formula V employed in scheme 3 as starting materials are either commercially available or are known in the literature or are synthesized in analogy to literature procedures via an alkylation using a β-keto ester anion and corresponding $R^3$-halide electrophile as known to persons skilled in the art.

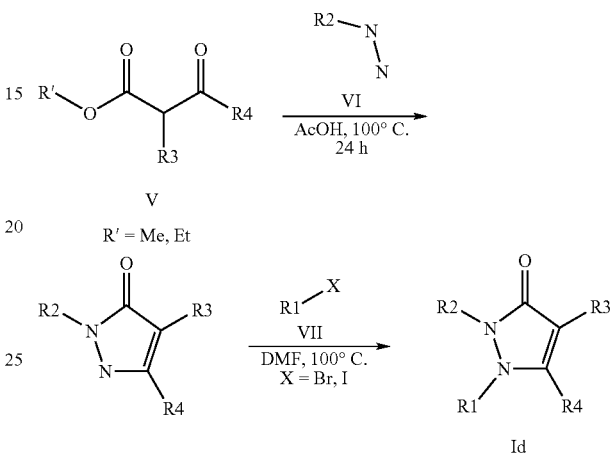

Compounds of formula Ie where $R^4$ means aryloxyalkyl, alkylcarbonylaminoaryloxyalkyl or alkyloxyalkyl are prepared from compounds of formula If where R4 means methyl via bromination using $Br_2$ in methylene chloride followed by displacement with the corresponding alcohol nucleophile (HO—Y) in the presence of cesium carbonate and potassium iodide in acetonitrile, as indicated in scheme 4.

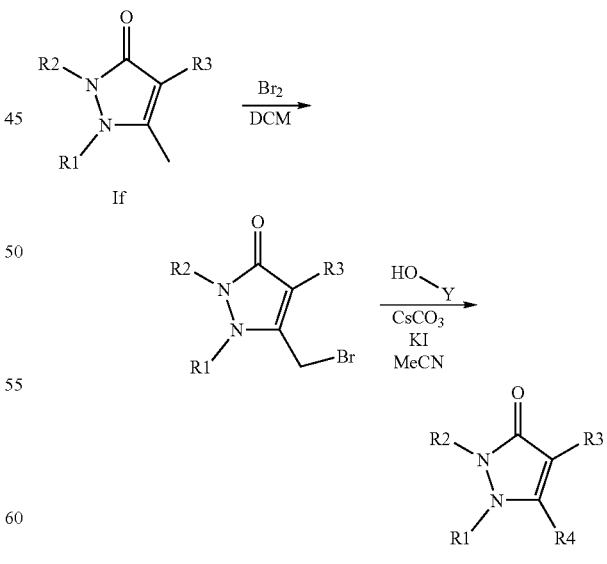

Compounds of formula II employed in scheme 1 and 2 as starting materials can be prepared according to the general methods as summarized in scheme 5 or are either commercially available or known in the literature. Method 1 involves the condensation of a β-keto ester with a substituted hydrazine of formula VI followed by the thermal or microwave assisted alkylation with compound formula VII in a sealed reaction vessel to afford compound of formula II. Method 2 involves the condensation of a β-keto ester with hydrazine hydrate to give compound IIa wherein $R^1$ and $R^2$ are H. Optionally compound IIa can be annulated using a di-haloalkane of formula Br—Y—Br using thermal or microwave assisted conditions with one equivalent of base or via a two step process by alkylation on either nitrogen atom 1 or nitrogen atom 2 followed by ring closure using basic conditions or palladium or copper-mediated coupling reactions analogous to known literature procedures or known to those skilled in the art. Method 3 involves the alkylation of a β-keto ester, via a di-anion formation with LDA, with a di-bromide and the resultant β-keto ester bromide was then reacted with a hydrazine of formula VI to give the annulated pyrazolone IIb. Method 4 involves the reaction of an alkynoic ester with an appropriately substituted hydrazine of formula VI under basic conditions in tert.-butanol (see also EP0680954) followed by alkylation of the product at nitrogen atom 2 under previously described conditions.

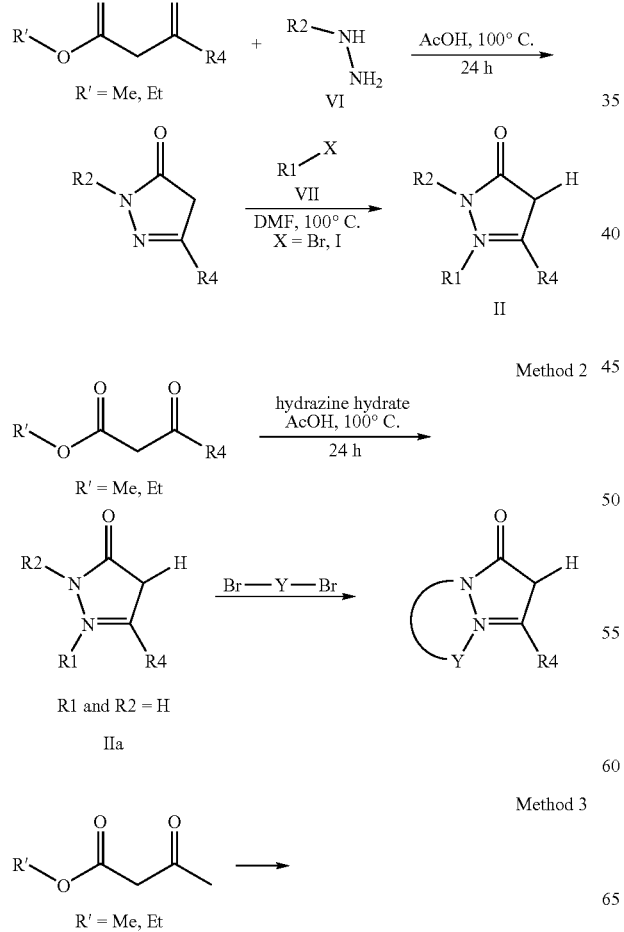

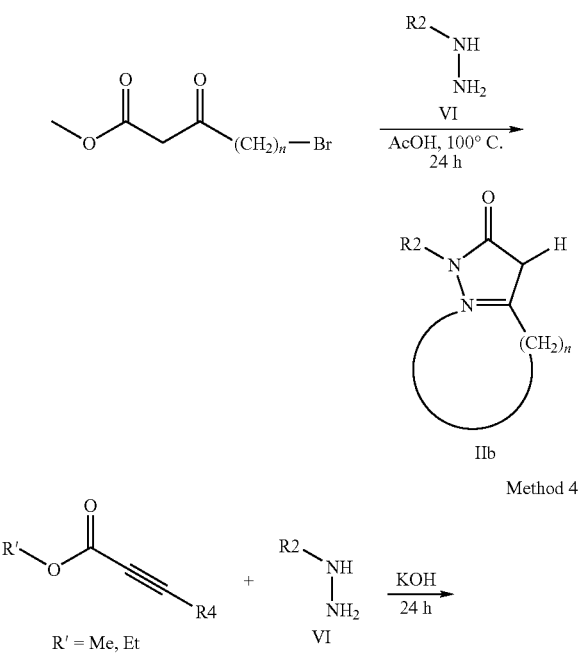

More elaborately substituted β-ketoesters such as VII and VIII are prepared according to scheme 6 via the acylation of monoethyl malonate with an appropriate acid chloride derivative or via the reaction of a zinc enolate with an appropriate nitrile compound followed by hydrolysis.

-continued

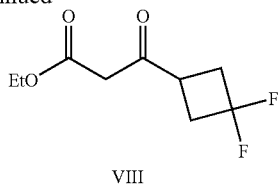

VIII

The corresponding substituted hydrazines of formula VI are either commercially available or are known in the literature or are synthesized in analogy to literature procedures (such as WO 2004/056324; *J. Org. Chem.* 1984, 49, 336-42; *J. Am. Chem. Soc.* 1986, 108, 7981-4 or *Bioorg. Med. Chem.* 2004, 12, 1357-1366). The corresponding β-keto ester starting materials exemplified in scheme 5 are either commercially available or are known in the literature or are synthesised according to or in analogy to literature procedures (e.g. *J. Am. Chem. Soc.* 1968, 90, 2882-2889) from starting materials commercially available or known.

A preferred process for the preparation of a compound of formula

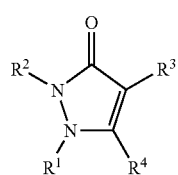 (I)

as described before comprises one of the following reactions, wherein $R^1$ to $R^4$ are defined as before and R' and R" are hydrogen or R' and R" form together —$(CH_2)_2$— or —$(CH_2)_3$—:

reaction of a compound according to formula

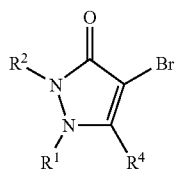

in the presence of a compound of formula

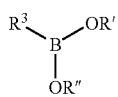 III in order to obtain a compound of formula I. Particularly preferred are those reactions according to a), wherein a palladium catalyst is present. Preferred is the above reaction wherein the palladium catalyst is formed by addition of palladium such as e.g. $Pd(OAc)_2$, phosphine ligand, such as e.g. tricyclohexylphosphine, and a base such as e.g. $K_3PO_4$.

reaction of a compound of formula

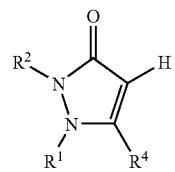 II in the presence of $R^3$—OH in order to obtain a compound of formula I. Particularly preferred are those reactions according to b), wherein a Lewis acid such as e.g. boron trifluoride diethyletherate or tin tetrachloride are present in particular in a solvent such as e.g. pentane or dichloroethane.

Preferred intermediates are:
Cyclopropyl-2-phenyl-2,4-dihydro-pyrazol-3-one;
Cyclopropyl-1-methyl-2-phenyl-1,2-dihydro-pyrazol-3-one;
4-Bromo-5-cyclopropyl-1-methyl-2-phenyl-1,2-dihydro-pyrazol-3-one;
Cyclopropyl-2-(2-fluoro-phenyl)-2,4-dihydro-pyrazol-3-one;
Cyclopropyl-2-(2-fluoro-phenyl)-1-methyl-1,2-dihydro-pyrazol-3-one;
4-Bromo-5-cyclopropyl-2-(2-fluoro-phenyl)-1-methyl-1,2-dihydro-pyrazol-3-one;
Cyclopropyl-2-(4-fluoro-phenyl)-2,4-dihydro-pyrazol-3-one;
5-Cyclopropyl-2-(4-fluoro-phenyl)-1-methyl-1,2-dihydro-pyrazol-3-one;
4-Bromo-5-cyclopropyl-2-(4-fluoro-phenyl)-1-methyl-1,2-dihydro-pyrazol-3-one;
5-Cyclopropyl-2-(2,4-difluoro-phenyl)-2,4-dihydro-pyrazol-3-one;
5-Cyclopropyl-2-(2,4-difluoro-phenyl)-1-methyl-1,2-dihydro-pyrazol-3-one;
4-Bromo-5-cyclopropyl-2-(2,4-difluoro-phenyl)-1-methyl-1,2-dihydro-pyrazol-3-one;
5-Cyclopropyl-2-(3-fluoro-phenyl)-2,4-dihydro-pyrazol-3-one;
5-Cyclopropyl-2-(3-fluoro-phenyl)-1-methyl-1,2-dihydro-pyrazol-3-one;
4-Bromo-5-cyclopropyl-2-(3-fluoro-phenyl)-1-methyl-1,2-dihydro-pyrazol-3-one;
2-(2-Chloro-phenyl)-5-cyclopropyl-2,4-dihydro-pyrazol-3-one;
2-(2-Chloro-phenyl)-5-cyclopropyl-1-methyl-1,2-dihydro-pyrazol-3-one;
4-Bromo-2-(2-chloro-phenyl)-5-cyclopropyl-1-methyl-1,2-dihydro-pyrazol-3-one;
2-(3-Chloro-phenyl)-5-cyclopropyl-2,4-dihydro-pyrazol-3-one;
2-(3-Chloro-phenyl)-5-cyclopropyl-1-methyl-1,2-dihydro-pyrazol-3-one;
4-Bromo-2-(3-chloro-phenyl)-5-cyclopropyl-1-methyl-1,2-dihydro-pyrazol-3-one;
5-Cyclopropyl-2-(2-trifluoromethyl-phenyl)-2,4-dihydro-pyrazol-3-one;
5-Cyclopropyl-1-methyl-2-(2-trifluoromethyl-phenyl)-1,2-dihydro-pyrazol-3-one;
4-Bromo-5-cyclopropyl-1-methyl-2-(2-trifluoromethyl-phenyl)-1,2-dihydro-pyrazol-3-one;
5-Cyclopropyl-2-(3-trifluoromethyl-phenyl)-2,4-dihydro-pyrazol-3-one;

5-Cyclopropyl-1-methyl-2-(3-trifluoromethyl-phenyl)-1,2-dihydro-pyrazol-3-one;
4-Bromo-5-cyclopropyl-1-methyl-2-(3-trifluoromethyl-phenyl)-1,2-dihydro-pyrazol-3-one;
5-Cyclopropyl-2-(4-fluoro-2-trifluoromethyl-phenyl)-2,4-dihydro-pyrazol-3-one;
5-Cyclopropyl-2-(4-fluoro-2-trifluoromethyl-phenyl)-1-methyl-1,2-dihydro-pyrazol-3-one;
4-Bromo-5-cyclopropyl-2-(4-fluoro-2-trifluoromethyl-phenyl)-1-methyl-1,2-dihydro-pyrazol-3-one;
5-Cyclopropyl-2-(2-methoxy-phenyl)-1-methyl-1,2-dihydro-pyrazol-3-one;
4-Bromo-5-cyclopropyl-2-(2-methoxy-phenyl)-1-methyl-1,2-dihydro-pyrazol-3-one;
5-Cyclopropyl-2-naphthalen-1-yl-2,4-dihydro-pyrazol-3-one;
5-Cyclopropyl-1-methyl-2-naphthalen-1-yl-1,2-dihydro-pyrazol-3-one;
4-Bromo-5-cyclopropyl-1-methyl-2-naphthalen-1-yl-1,2-dihydro-pyrazol-3-one;
5-Cyclopropyl-1-ethyl-2-(4-fluoro-phenyl)-1,2-dihydro-pyrazol-3-one;
4-Bromo-5-cyclopropyl-1-ethyl-2-(4-fluoro-phenyl)-1,2-dihydro-pyrazol-3-one;
5-Cyclopropyl-1-ethyl-2-(3-fluoro-phenyl)-1,2-dihydro-pyrazol-3-one;
4-Bromo-5-cyclopropyl-1-ethyl-2-(3-fluoro-phenyl)-1,2-dihydro-pyrazol-3-one;
2-(2-Chloro-phenyl)-5-cyclopropyl-1-ethyl-1,2-dihydro-pyrazol-3-one;
4-Bromo-2-(2-chloro-phenyl)-5-cyclopropyl-1-ethyl-1,2-dihydro-pyrazol-3-one;
2-(3-Chloro-phenyl)-5-cyclopropyl-1-ethyl-1,2-dihydro-pyrazol-3-one;
4-Bromo-2-(3-chloro-phenyl)-5-cyclopropyl-1-ethyl-1,2-dihydro-pyrazol-3-one;
5-Cyclopropyl-1-ethyl-2-(2-trifluoromethyl-phenyl)-1,2-dihydro-pyrazol-3-one;
4-Bromo-5-cyclopropyl-1-ethyl-2-(2-trifluoromethyl-phenyl)-1,2-dihydro-pyrazol-3-one;
Benzyl-5-cyclopropyl-2-(2-trifluoromethyl-phenyl)-1,2-dihydro-pyrazol-3-one;
Benzyl-4-bromo-5-cyclopropyl-2-(2-trifluoromethyl-phenyl)-1,2-dihydro-pyrazol-3-one;
5-Cyclopropyl-1-cyclopropylmethyl-2-(2-trifluoromethyl-phenyl)-1,2-dihydro-pyrazol-3-one;
4-Bromo-5-cyclopropyl-1-cyclopropylmethyl-2-(2-trifluoromethyl-phenyl)-1,2-dihydro-pyrazol-3-one;
Benzyl-5-cyclopropyl-2,4-dihydro-pyrazol-3-one;
Benzyl-5-cyclopropyl-1-methyl-1,2-dihydro-pyrazol-3-one;
Benzyl-4-bromo-5-cyclopropyl-1-methyl-1,2-dihydro-pyrazol-3-one;
Cyclopropyl-6,7,8,9-tetrahydro-5H-pyrazolo[1,2-a][1,2]diazepin-1-one;
Bromo-3-cyclopropyl-6,7,8,9-tetrahydro-5H-pyrazolo[1,2-a][1,2]diazepin-1-one;
Cyclobutyl-2-phenyl-2,4-dihydro-pyrazol-3-one;
Cyclobutyl-1-methyl-2-phenyl-1,2-dihydro-pyrazol-3-one;
Bromo-5-cyclobutyl-1-methyl-2-phenyl-1,2-dihydro-pyrazol-3-one;
Cyclobutyl-2-(2-trifluoromethyl-phenyl)-2,4-dihydro-pyrazol-3-one;
Cyclobutyl-1-methyl-2-(2-trifluoromethyl-phenyl)-1,2-dihydro-pyrazol-3-one;
Bromo-5-cyclobutyl-1-methyl-2-(2-trifluoromethyl-phenyl)-1,2-dihydro-pyrazol-3-one;
5-(1-Methyl-cyclopropyl)-2-(2-trifluoromethyl-phenyl)-2,4-dihydro-pyrazol-3-one;
Methyl-5-(1-methyl-cyclopropyl)-2-(2-trifluoromethyl-phenyl)-1,2-dihydro-pyrazol-3-one;
Bromo-1-methyl-5-(1-methyl-cyclopropyl)-2-(2-trifluoromethyl-phenyl)-1,2-dihydro-pyrazol-3-one;
tert-Butyl-2-(2-trifluoromethyl-phenyl)-2,4-dihydro-pyrazol-3-one;
tert-Butyl-1-methyl-2-(2-trifluoromethyl-phenyl)-1,2-dihydro-pyrazol-3-one;
4-Bromo-5-tert-butyl-1-methyl-2-(2-trifluoromethyl-phenyl)-1,2-dihydro-pyrazol-3-one;
3-(2,2-Dimethyl-cyclopropyl)-3-oxo-propionic acid ethyl ester;
5-(2,2-Dimethyl-cyclopropyl)-2-(2-trifluoromethyl-phenyl)-2,4-dihydro-pyrazol-3-one;
5-(2,2-Dimethyl-cyclopropyl)-1-methyl-2-(2-trifluoromethyl-phenyl)-1,2-dihydro-pyrazol-3-one;
4-Bromo-5-(2,2-dimethyl-cyclopropyl)-1-methyl-2-(2-trifluoromethyl-phenyl)-1,2-dihydro-pyrazol-3-one;
Phenyl-4,5,6,7-tetrahydro-pyrazolo[1,5-a]pyridin-2-one;
Bromo-1-phenyl-4,5,6,7-tetrahydro-pyrazolo[1,5-a]pyridin-2-one;
Cyclopropyl-1,5-dimethyl-2-phenyl-1,2-dihydro-pyrazol-3-one;
Bromomethyl-4-cyclopropyl-1-methyl-2-phenyl-1,2-dihydro-pyrazol-3-one;
2-(4-Fluoro-phenyl)-5-methyl-2,4-dihydro-pyrazol-3-one;
2-(4-Fluoro-phenyl)-1,5-dimethyl-1,2-dihydro-pyrazol-3-one;
Bromo-2-(4-fluoro-phenyl)-1,5-dimethyl-1,2-dihydro-pyrazol-3-one;
4-Cyclopropyl-2-(4-fluoro-phenyl)-1,5-dimethyl-1,2-dihydro-pyrazol-3-one;
Bromomethyl-4-cyclopropyl-2-(4-fluoro-phenyl)-1-methyl-1,2-dihydro-pyrazol-3-one;
2-(2-Fluoro-phenyl)-5-methyl-2,4-dihydro-pyrazol-3-one;
2-(2-Fluoro-phenyl)-1,5-dimethyl-1,2-dihydro-pyrazol-3-one;
4-Bromo-2-(2-fluoro-phenyl)-1,5-dimethyl-1,2-dihydro-pyrazol-3-one;
4-Cyclopropyl-2-(2-fluoro-phenyl)-1,5-dimethyl-1,2-dihydro-pyrazol-3-one;
Bromomethyl-4-cyclopropyl-2-(2-fluoro-phenyl)-1-methyl-1,2-dihydro-pyrazol-3-one;
5-(4-Fluoro-phenyl)-3-oxo-pentanoic acid methyl ester;
2-(4-Fluoro-phenyl)-5-[2-(4-fluoro-phenyl)-ethyl]-2,4-dihydro-pyrazol-3-one;
2-(4-Fluoro-phenyl)-5-[2-(4-fluoro-phenyl)-ethyl]-1-methyl-1,2-dihydro-pyrazol-3-one
4-Bromo-2-(4-fluoro-phenyl)-5-[2-(4-fluoro-phenyl)-ethyl]-1-methyl-1,2-dihydro-pyrazol-3-one;
2-(2-Fluoro-phenyl)-5-[2-(4-fluoro-phenyl)-ethyl]-2,4-dihydro-pyrazol-3-one;
2-(2-Fluoro-phenyl)-5-[2-(4-fluoro-phenyl)-ethyl]-1-methyl-1,2-dihydro-pyrazol-3-one;
4-Bromo-2-(2-fluoro-phenyl)-5-[2-(4-fluoro-phenyl)-ethyl]-1-methyl-1,2-dihydro-pyrazol-3-one;
Ethyl-2-(4-fluoro-phenyl)-5-methyl-1,2-dihydro-pyrazol-3-one
4-Bromo-1-ethyl-2-(4-fluoro-phenyl)-5-methyl-1,2-dihydro-pyrazol-3-one
4-Cyclopropyl-1-ethyl-2-(4-fluoro-phenyl)-5-methyl-1,2-dihydro-pyrazol-3-one
5-Bromomethyl-4-cyclopropyl-1-ethyl-2-(4-fluoro-phenyl)-1,2-dihydro-pyrazol-3-one 2-(1,7,7-Trimethyl-bicyclo[2.2.1]hept-2-yl)-1,2,4,5,6,7-hexahydro-indazol-3-one;
2-(2,4-Dichloro-phenyl)-1,2,4,5,6,7-hexahydro-indazol-3-one;
2-(2-Trifluoromethyl-phenyl)-1,4,5,6,7,8-hexahydro-2H-cycloheptapyrazol-3-one;
4-Adamantan-1-yl-5-cyclopropyl-1,2-dihydro-pyrazol-3-one;
Benzyl-2,5-dimethyl-1,2-dihydro-pyrazol-3-one;
5-Methyl-1-pyridin-2-yl-1,2-dihydro-pyrazol-3-one;
5,6,7,8-Tetrahydro-4H-pyrazolo[1,5-a]azepin-2-one;
4,5,6,7-Tetrahydro-pyrazolo[1,5-a]pyridin-2-one; and
Adamantan-1-yl-5,6,7,8-tetrahydro-4H-pyrazolo[1,5-a]azepin-2-one.

The compounds of formula I as described above for use as therapeutically active substance are a further embodiment of the invention.

The compounds selected from 3-cyclopropyl-4-isopropyl-2-methyl-1-phenyl-3-pyrazolin-5-one; 1,2-dihydro-5-methyl-4-tricyclo(3.3.1.13,7)dec-1-yl-3H-pyrazol-3-one; 1,2,3,4,6,7,8,9-octahydro-10H,12H-indazolo(1,2-a)indazole-10,12-dione; 1,2,4,5,6,7-hexahydro-1-methyl-2-phenyl-3H-indazol-3-one; 1,4,5,6-tetrahydro-1-methyl-2-phenyl-3(2H)-cyclopentapyrazolone; 1,4,5,6-tetrahydro-1-benzyl-2-phenyl-3(2H)-cyclopentapyrazolone; 1,4,5,6-tetrahydro-1-ethyl-2-(4-methyl)-phenyl-3(2H)-cyclopentapyrazolone; 1,4,5,6-tetrahydro-1-ethyl-2-phenyl-3(2H)-cyclopentapyrazolone; or 1,4,5,6,7,8-hexahydro-1-methyl-2-phenyl-3(2H)-cycloheptapyrazolone for use as therapeutically active substance are also an embodiment of the present invention.

Also an embodiment of the present invention are compounds as described above for the preparation of medicaments for the prophylaxis and therapy of illnesses which are caused by disorders associated with the enzyme 11beta-hydroxysteroid dehydrogenase 1 (11bHSD1).

A further embodiment of the present invention are the compounds selected from 3-cyclopropyl-4-isopropyl-2-methyl-1-phenyl-3-pyrazolin-5-one; 1,2-dihydro-5-methyl-4-tricyclo(3.3.1.13,7)dec-1-yl-3H-pyrazol-3-one; 1,2,3,4,6,7,8,9-octahydro-10H,12H-indazolo(1,2-a)indazole-10,12-dione; 1,2,4,5,6,7-hexahydro-1-methyl-2-phenyl-3H-indazol-3-one; 1,4,5,6-tetrahydro-1-methyl-2-phenyl-3(2H)-cyclopentapyrazolone; 1,4,5,6-tetrahydro-1-benzyl-2-phenyl-3(2H)-cyclopentapyrazolone; 1,4,5,6-tetrahydro-1-ethyl-2-(4-methyl)-phenyl-3(2H)-cyclopentapyrazolone; 1,4,5,6-tetrahydro-1-ethyl-2-phenyl-3(2H)-cyclopentapyrazolone; or 1,4,5,6,7,8-hexahydro-1-methyl-2-phenyl-3(2H)-cycloheptapyrazolone for the preparation of medicaments for the prophylaxis and therapy of illnesses which are caused by disorders associated with the enzyme 11beta-hydroxysteroid dehydrogenase 1 (11bHSD1).

Likewise an embodiment of the invention are pharmaceutical compositions comprising a compound of the formula I as described above and a therapeutically inert carrier.

Moreover, an embodiment of the invention are pharmaceutical compositions comprising a compound selected from 3-cyclopropyl-4-isopropyl-2-methyl-1-phenyl-3-pyrazolin-5-one; 1,2-dihydro-5-methyl-4-tricyclo(3.3.1.13,7)dec-1-yl-3H-pyrazol-3-one; 1,2,3,4,6,7,8,9-octahydro-10H,12H-indazolo(1,2-a)indazole-10,12-dione; 1,2,4,5,6,7-hexahydro-1-methyl-2-phenyl-3H-indazol-3-one; 1,4,5,6-tetrahydro-1-methyl-2-phenyl-3(2H)-cyclopentapyrazolone; 1,4,5,6-tetrahydro-1-benzyl-2-phenyl-3(2H)-cyclopentapyrazolone; 1,4,5,6-tetrahydro-1-ethyl-2-(4-methyl)-phenyl-3(2H)-cyclopentapyrazolone; 1,4,5,6-tetrahydro-1-ethyl-2-phenyl-3(2H)-cyclopentapyrazolone; or 1,4,5,6,7,8-hexahydro-1-methyl-2-phenyl-3(2H)-cycloheptapyrazolone and a therapeutically inert carrier.

A further preferred embodiment of the present invention is the use of a compound of the formula I as described above for the preparation of medicaments for the treatment and prophylaxis of diabetes, obesity, eating disorders, dyslipidemiae and hypertension.

An other preferred embodiment of the present invention is the use of a compound selected from 3-cyclopropyl-4-isopropyl-2-methyl-1-phenyl-3-pyrazolin-5-one; 1,2-dihydro-5-methyl-4-tricyclo(3.3.1.13,7)dec-1-yl-3H-pyrazol-3-one; 1,2,3,4,6,7,8,9-octahydro-10H,12H-indazolo(1,2-a)indazole-10,12-dione; 1,2,4,5,6,7-hexahydro-1-methyl-2-phenyl-3H-indazol-3-one; 1,4,5,6-tetrahydro-1-methyl-2-phenyl-3(2H)-cyclopentapyrazolone; 1,4,5,6-tetrahydro-1-benzyl-2-phenyl-3(2H)-cyclopentapyrazolone; 1,4,5,6-tetrahydro-1-ethyl-2-(4-methyl)-phenyl-3(2H)-cyclopentapyrazolone; 1,4,5,6-tetrahydro-1-ethyl-2-phenyl-3(2H)-cyclopentapyrazolone; or 1,4,5,6,7,8-hexahydro-1-methyl-2-phenyl-3(2H)-cycloheptapyrazolone for the preparation of medicaments for the treatment and prophylaxis of diabetes, obesity, eating disorders, dyslipidemiae and hypertension.

Particularly preferred is the use of a compound according to formula I as described above for the preparation of medicaments for the treatment and prophylaxis of diabetes Type II.

Preferred is the use of a compound selected from 3-cyclopropyl-4-isopropyl-2-methyl-1-phenyl-3-pyrazolin-5-one; 1,2-dihydro-5-methyl-4-tricyclo(3.3.1.13,7)dec-1-yl-3H-pyrazol-3-one; 1,2,3,4,6,7,8,9-octahydro-10H,12H-indazolo(1,2-a)indazole-10,12-dione; 1,2,4,5,6,7-hexahydro-1-methyl-2-phenyl-3H-indazol-3-one; 1,4,5,6-tetrahydro-1-methyl-2-phenyl-3(2H)-cyclopentapyrazolone; 1,4,5,6-tetrahydro-1-benzyl-2-phenyl-3(2H)-cyclopentapyrazolone; 1,4,5,6-tetrahydro-1-ethyl-2-(4-methyl)-phenyl-3(2H)-cyclopentapyrazolone; 1,4,5,6-tetrahydro-1-ethyl-2-phenyl-3(2H)-cyclopentapyrazolone; or 1,4,5,6,7,8-hexahydro-1-methyl-2-phenyl-3(2H)-cycloheptapyrazolone for the preparation of medicaments for the treatment and prophylaxis of diabetes Type II.

A further embodiment of the present invention comprises a compound according to formula I as described above, when manufactured according to any one of the described processes.

Also an embodiment of the invention is a method for the treatment and prophylaxis of diabetes, obesity, eating disorders, dyslipidemiae and hypertension, which method comprises administering an effective amount of a compound of formula I as described above.

Also an embodiment of the invention is a method for the treatment and prophylaxis of diabetes, obesity, eating disorders, dyslipidemiae and hypertension, which method comprises administering an effective amount of a compound selected from 3-cyclopropyl-4-isopropyl-2-methyl-1-phenyl-3-pyrazolin-5-one; 1,2-dihydro-5-methyl-4-tricyclo(3.3.1.13,7)dec-1-yl-3H-pyrazol-3-one; 1,2,3,4,6,7,8,9-octahydro-10H,12H-indazolo(1,2-a)indazole-10,12-dione; 1,2,4,5,6,7-hexahydro-1-methyl-2-phenyl-3H-indazol-3-one; 1,4,5,6-tetrahydro-1-methyl-2-phenyl-3(2H)-cyclopentapyrazolone; 1,4,5,6-tetrahydro-1-benzyl-2-phenyl-3(2H)-cyclopentapyrazolone; 1,4,5,6-tetrahydro-1-ethyl-2-(4-methyl)-phenyl-3(2H)-cyclopentapyrazolone; 1,4,5,6-tetrahydro-1-ethyl-2-phenyl-3(2H)-cyclopentapyrazolone; or 1,4,5,6,7,8-hexahydro-1-methyl-2-phenyl-3(2H)-cycloheptapyrazolone.

Particularly preferred is a method for the treatment and prophylaxis of diabetes Type II, which method comprises administering an effective amount of a compound according to formula I as described above.

Further preferred is a method for the treatment and prophylaxis of diabetes Type II, which method comprises administering an effective amount of a compound selected from 3-cyclopropyl-4-isopropyl-2-methyl-1-phenyl-3-pyrazolin-5-one; 1,2-dihydro-5-methyl-4-tricyclo(3.3.1.13,7)dec-1-yl-3H-pyrazol-3-one; 1,2,3,4,6,7,8,9-octahydro-10H,12H-indazolo(1,2-a)indazole-10,12-dione; 1,2,4,5,6,7-hexahydro-1-methyl-2-phenyl-3H-indazol-3-one; 1,4,5,6-tetrahydro-1-methyl-2-phenyl-3(2H)-cyclopentapyrazolone; 1,4,5,6-tetrahydro-1-benzyl-2-phenyl-3 (2H)-cyclopentapyrazolone; 1,4,5,6-tetrahydro-1-ethyl-2-(4-methyl)-phenyl-3(2H)-cyclopentapyrazolone; 1,4,5,6-tetrahydro-1-ethyl-2-phenyl-3(2H)-cyclopentapyrazolone; or 1,4,5,6,7,8-hexahydro-1-methyl-2-phenyl-3(2H)-cycloheptapyrazolone.

Assay Procedures

Transient Expression and Partial Purification:

The cDNA encoding the human 11beta-HSD1 protein was cloned into the expression vector pcDNA3 (Stratagene). This construct (for details see Alex Odermatt et al.; J Biol Chem., 1999, Vol. 274, Issue 40, 28762-28770) was used to transiently express the protein in HEK293 cells (ATCC number: CRL-1573, described in Graham, F. L., Smiley, J., Russell, W. C., Nairn, R.; (1977)) using lipofectamine. 48 h after transfection cells were washed twice with ice-cold PBS (Phosphate buffered Saline). To 1 volume of cell suspension in PBS 2 volumes of ice-cold lysis buffer (50 mM Tris; pH7.5; 1 mM EDTA; 100 mM NaCl) were added. The cells were lysed by Potter-homogenization (20 strokes). The resulting homogenate was sonicated wit a tip sonicator (10% output; 2×30 sec.) and cleared by a low speed centrifugation (10 min×9000 g; 4° C.). The microsomal fraction was collected by a high speed centrifugation (60 min×110'000 g). The resulting pellet was resuspended in storage buffer (20 mM Tris pH 7.5; 1 mM EDTA; 10% Glycerol) and the centrifugation was repeated. The resulting pellet containing the microsomal fraction was again taken up into storage buffer and aliquots were kept frozen in liquid Nitrogen until use.

Generation of Stable Cell Lines Expressing 11beta-HSD1:

The same construct used for transient expression of human 11beta-HSD1 was also used to establish cell lines stably expressing the protein. Briefly, (HEK293) cells were transfected with 11beta-HSD1 construct using the lipofectamine reagent (Gibco BRL) according to the manufacturer's instruction. Two days after transfection, geneticin selection (0.8 mg/ml) was initiated and several stable clones were isolated. One clone was further used for pharmacological characterization.

Microsome Assay

Microsomes isolated from HEK293 cells transiently expressing human 11beta-HSD1 (for details see above) were incubated in assay buffer (100 mM NaCl; 1 mM EDTA; 1 mM EGTA; 1 mM MgCl; 250 mM Sucrose; 20 mM Tris pH 7.4; Cortisone 50-200 nM and NADPH 1 mM) together with different concentrations of test substances. After 60 min. of incubation at 37° C. the assay was stopped by heating to 80° C. (5 min.) and by addition of the inhibitor Carbenoxolone (1 uM). The amount of Cortisol produced in this assay was determined using a commercially available, ELISA-based Cortisol-detection kit (Distributed by Assay Design, Inc.). Inhibitors were characterized by there IC50 values, e.g. the concentration at which the production of cortisol was 50% reduced.

In this test preferred compounds as described above have IC50 values below 1000 nM; more preferred compounds have IC50 values below 100 nM. Most preferred compounds have IC50 values below 10 nM.

Cellular Assay

To measure the effect of inhibitors in intact cells HEK293 cells stably expressing human 11beta-HSD1 (see above) were cultivated in 96 well plates in DMEM. First inhibitors and 60 min later Cortisone was added to the cells. After 60 min of incubation at 37° C. in a 5% CO2 atmosphere part of the medium was removed and the conversion from Cortisone to Cortisol was measured using a commercially available ELISA kit (Distributed by Assay Design, Inc.).

Results obtained in the microsome assay using representative compounds of the invention as the test compounds are shown in the following table:

| Compound | h 11-beta-HSD 1 $IC_{50}$ (nM) |
| --- | --- |
| Example 1 | 21 |
| Example 51 | 133 |

Compounds as described above have $IC_{50}$ values below 1000 nM; preferred compounds have $IC_{50}$ values below 100 nM. More preferred compounds have $IC_{50}$ values below 10 nM. These results have been obtained by using the foregoing test.

The compounds of formula I and their pharmaceutically acceptable salts and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula I and their pharmaceutically acceptable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutically acceptable salts can be used for the prophylaxis and treatment of arthritis, cardiovascular diseases, diabetes, renal failure and particularly eating disorders and obesity. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

EXAMPLES

Example 1

4,5-Dicyclopropyl-1-methyl-2-phenyl-1,2-dihydro-pyrazol-3-one

Step A] 5-Cyclopropyl-2-phenyl-2,4-dihydro-pyrazol-3-one

To a solution of methyl-3-cyclopropyl-3-oxopropionate (17 g) in acetic acid (40 mL) in a round bottom flask under argon was added phenylhydrazine (12.93 g). The mixture was immersed into an oil bath and heated to 120° C. overnight. The reaction vessel was then cooled and the acetic acid was evaporated in vacuo and the remaining solid was dissolved in EtOAc and water. The phases were separated and the aqueous phase was extracted with further EtOAc. The combined organic phases were washed with brine, dried over sodium sulfate, filtered and evaporated in vacuo and azeotroped with toluene (2×). The crude residue was then purified via trituration with a 1:1 mixture of ether/pentane to afford the desired 5-cyclopropyl-2-phenyl-2,4-dihydro-pyrazol-3-one (20.8 g) as a light brown solid. MS (ESI$^+$): 201.3 ([M+H]$^+$).

Step B] 5-Cyclopropyl-1-methyl-2-phenyl-1,2-dihydro-pyrazol-3-one

To a solution of 5-cyclopropyl-2-phenyl-2,4-dihydro-pyrazol-3-one (5 g) in DMF (25 mL) was added iodomethane (1.56 mL) and the mixture was placed into a pressure bomb and sealed. The reaction vessel was then heated in an oil bath to 100° C. over two days. The reaction vessel was then cooled and the DMF was evaporated in vacuo. The residue was dissolved in EtOAc and saturated and washed with saturated sodium bicarbonate solution. The phases were separated and the aqueous solution was extracted with EtOAc another two times at neutral pH. The combined organic phases were washed with brine, dried over sodium sulfate, filtered and evaporated in vacuo to afford a crude residue. Flash column chromatography over silica gel using ISCO combiflash chromatography and eluting with EtOAc/heptane and 3% AcOH afforded the desired 5-cyclopropyl-1-methyl-2-phenyl-1,2-dihydro-pyrazol-3-one (3.35 g) as a light brown solid. MS (ESI$^+$): 215.3 ([M+H]$^+$).

Step C] 4-Bromo-5-cyclopropyl-1-methyl-2-phenyl-1,2-dihydro-pyrazol-3-one

To a solution of 5-cyclopropyl-1-methyl-2-phenyl-1,2-dihydro-pyrazol-3-one (3.35 g) in methylene chloride (80 mL) was added N-bromosuccinimide (2.78 g). The reaction vessel was wrapped in aluminium foil and stirred for 24 hours. The solvent was evaporated in vacuo and the residue was dissolved in EtOAc and water. The phases were separated and the aqueous phase was extracted with more EtOAc. The combined organic phases were washed with brine, dried over sodium sulfate, filtered and reduced in vacuo to give a crude residue. Flash column chromatography over silica gel using ISCO combiflash chromatography and eluting with EtOAc/heptane afforded the desired 4-bromo-5-cyclopropyl-1-methyl-2-phenyl-1,2-dihydro-pyrazol-3-one (3.89 g) as a light brown solid. MS (ESI$^+$): 293.1 ([M+H]$^+$).

Step D] 4,5-Dicyclopropyl-1-methyl-2-phenyl-1,2-dihydro-pyrazol-3-one

Into a sealable tube under argon was added 4-bromo-5-cyclopropyl-1-methyl-2-phenyl-1,2-dihydro-pyrazol-3-one (2.59 g), cyclopropylboronic acid (1.23 g), potassium phosphate (8.18 g), tricyclohexyl phosphine (0.30 g), toluene (50 mL) and water (3.2 mL). To this was added palladium acetate (0.11 g) and the tube was sealed and stirred at 100° C. for 4 days. The reaction vessel was then cooled and then diluted with water/EtOAc. The phases were separated and the aqueous phase was extracted with further EtOAc. The combined organic phases were washed with brine, dried over sodium sulfate and evaporated in vacuo to afford a crude residue. Flash column chromatography over silica gel using ISCO combiflash chromatography and eluting with EtOAc/heptane afforded the desired 4,5-dicyclopropyl-1-methyl-2-phenyl-1,2-dihydro-pyrazol-3-one which was further purified by crystallization from EtOAc/pentante to give 1.12 g of the desired title compound as a white crystalline solid. MS (ESI$^+$): 255.3 ([M+H]$^+$).

Example 2

4,5-Dicyclopropyl-2-(2-fluoro-phenyl)-1-methyl-1,2-dihydro-pyrazol-3-one

This material was obtained in analogy to example 1 using 2-fluorophenylhydrazine hydrochloride (step A) via the following intermediates:

Step A] 5-Cyclopropyl-2-(2-fluoro-phenyl)-2,4-dihydro-pyrazol-3-one

Step B] 5-Cyclopropyl-2-(2-fluoro-phenyl)-1-methyl-1,2-dihydro-pyrazol-3-one

Step C] 4-Bromo-5-cyclopropyl-2-(2-fluoro-phenyl)-1-methyl-1,2-dihydro-pyrazol-3-one After step D the title compound 4,5-dicyclopropyl-2-(2-fluoro-phenyl)-1-methyl-1,2-dihydro-pyrazol-3-one was obtained as a light brown solid. MS (ESI$^+$): 273.3 ([M+H]$^+$).

Example 3

4,5-Dicyclopropyl-2-(4-fluoro-phenyl)-1-methyl-1,2-dihydro-pyrazol-3-one

This material was obtained in analogy to example 1 using 4-fluorophenylhydrazine hydrochloride (step A) via the following intermediates:

Step A] 5-Cyclopropyl-2-(4-fluoro-phenyl)-2,4-dihydro-pyrazol-3-one

Step B] 5-Cyclopropyl-2-(4-fluoro-phenyl)-1-methyl-1,2-dihydro-pyrazol-3-one

Step C] 4-Bromo-5-cyclopropyl-2-(4-fluoro-phenyl)-1-methyl-1,2-dihydro-pyrazol-3-one After step D the title compound 4,5-dicyclopropyl-2-(4-fluoro-phenyl)-1-methyl-1,2-dihydro-pyrazol-3-one was obtained as a light yellow solid. MS (ESI$^+$): 273.1 ([M+H]$^+$).

Example 4

4,5-Dicyclopropyl-2-(2,4-difluoro-phenyl)-1-methyl-1,2-dihydro-pyrazol-3-one This material was obtained in analogy to example 1 using 4-fluorophenylhydrazine hydrochloride (step A) via the following intermediates:
Step A] 5-Cyclopropyl-2-(2,4-difluoro-phenyl)-2,4-dihydro-pyrazol-3-one
Step B] 5-Cyclopropyl-2-(2,4-difluoro-phenyl)-1-methyl-1,2-dihydro-pyrazol-3-one
Step C] 4-Bromo-5-cyclopropyl-2-(2,4-difluoro-phenyl)-1-methyl-1,2-dihydro-pyrazol-3-one After step D the title compound 4,5-dicyclopropyl-2-(2,4-difluoro-phenyl)-1-methyl-1,2-dihydro-pyrazol-3-one was obtained as a light brown solid. (ESI$^+$): 291.1 ([M+H]$^+$).

Example 5

4,5-Dicyclopropyl-2-(3-fluoro-phenyl)-1-methyl-1,2-dihydro-pyrazol-3-one

This material was obtained in analogy to example 1 using 3-fluorophenylhydrazine (step A) via the following intermediates:
Step A] 5-Cyclopropyl-2-(3-fluoro-phenyl)-2,4-dihydro-pyrazol-3-one
Step B] 5-Cyclopropyl-2-(3-fluoro-phenyl)-1-methyl-1,2-dihydro-pyrazol-3-one
Step C] 4-Bromo-5-cyclopropyl-2-(3-fluoro-phenyl)-1-methyl-1,2-dihydro-pyrazol-3-one After step D the title compound 4,5-dicyclopropyl-2-(3-fluoro-phenyl)-1-methyl-1,2-dihydro-pyrazol-3-one was obtained as an off white solid. MS (ESI$^+$): 273.0 ([M+H]$^+$).

Example 6

2-(2-Chloro-phenyl)-4,5-dicyclopropyl-1-methyl-1,2-dihydro-pyrazol-3-one

This material was obtained in analogy to example 1 using 2-chlorophenylhydrazine (step A) via the following intermediates:
Step A] 2-(2-Chloro-phenyl)-5-cyclopropyl-2,4-dihydro-pyrazol-3-one
Step B] 2-(2-Chloro-phenyl)-5-cyclopropyl-1-methyl-1,2-dihydro-pyrazol-3-one
Step C] 4-Bromo-2-(2-chloro-phenyl)-5-cyclopropyl-1-methyl-1,2-dihydro-pyrazol-3-one After step D the title compound 2-(2-chloro-phenyl)-4,5-dicyclopropyl-1-methyl-1,2-dihydro-pyrazol-3-one was obtained as a white solid. MS (ESI$^+$): 289.0 ([M+H]$^+$).

Example 7

2-(3-Chloro-phenyl)-4,5-dicyclopropyl-1-methyl-1,2-dihydro-pyrazol-3-one

This material was obtained in analogy to example 1 using 3-chlorophenylhydrazine (step A) via the following intermediates:
Step A] 2-(3-Chloro-phenyl)-5-cyclopropyl-2,4-dihydro-pyrazol-3-one
Step B] 2-(3-Chloro-phenyl)-5-cyclopropyl-1-methyl-1,2-dihydro-pyrazol-3-one
Step C] 4-Bromo-2-(3-chloro-phenyl)-5-cyclopropyl-1-methyl-1,2-dihydro-pyrazol-3-one After step D the tide compound 2-(3-chloro-phenyl)-4,5-dicyclopropyl-1-methyl-1,2-dihydro-pyrazol-3-one was obtained as a light yellow solid. MS (ESI$^+$): 289.1 ([M+H]$^+$).

Example 8

4,5-Dicyclopropyl-1-methyl-2-(2-trifluoromethyl-phenyl)-1,2-dihydro-pyrazol-3-one This material was obtained in analogy to example 1 using 2-trifluoromethylphenylhydrazine (step A) via the following intermediates:
Step A] 5-Cyclopropyl-2-(2-trifluoromethyl-phenyl)-2,4-dihydro-pyrazol-3-one
Step B] 5-Cyclopropyl-1-methyl-2-(2-trifluoromethyl-phenyl)-1,2-dihydro-pyrazol-3-one
Step C] 4-Bromo-5-cyclopropyl-1-methyl-2-(2-trifluoromethyl-phenyl)-1,2-dihydro-pyrazol-3-one After step D the title compound 4,5-dicyclopropyl-1-methyl-2-(2-trifluoromethyl-phenyl)-1,2-dihydro-pyrazol-3-one was obtained as an off-white solid. MS (ESI$^+$): 323.5 ([M+H]$^+$).

Example 9

4,5-Dicyclopropyl-1-methyl-2-(3-trifluoromethyl-phenyl)-1,2-dihydro-pyrazol-3-one This material was obtained in analogy to example 1 using 3-trifluoromethylphenylhydrazine (step A) via the following intermediates:
Step A] 5-Cyclopropyl-2-(3-trifluoromethyl-phenyl)-2,4-dihydro-pyrazol-3-one
Step B] 5-Cyclopropyl-1-methyl-2-(3-trifluoromethyl-phenyl)-1,2-dihydro-pyrazol-3-one
Step C] 4-Bromo-5-cyclopropyl-1-methyl-2-(3-trifluoromethyl-phenyl)-1,2-dihydro-pyrazol-3-one After step D the title compound 4,5-dicyclopropyl-1-methyl-2-(3-trifluoromethyl-phenyl)-1,2-dihydro-pyrazol-3-one was obtained as a light yellow solid. MS (ESI$^+$): 323.5 ([M+H]$^+$).

Example 10

4,5-Dicyclopropyl-2-(4-fluoro-2-trifluoromethyl-phenyl)-1-methyl-1,2-dihydro-pyrazol-3-one This material was obtained in analogy to example 1 using 4-fluoro-3-trifluoromethylphenylhydrazine (prepared in analogy to WO 2004/056324 from 4-fluoro-2-trifluoromethyl-phenylamine) (step A) via the following intermediates:
Step A] 5-Cyclopropyl-2-(4-fluoro-2-trifluoromethyl-phenyl)-2,4-dihydro-pyrazol-3-one
Step B] 5-Cyclopropyl-2-(4-fluoro-2-trifluoromethyl-phenyl)-1-methyl-1,2-dihydro-pyrazol-3-one
Step C] 4-Bromo-5-cyclopropyl-2-(4-fluoro-2-trifluoromethyl-phenyl)-1-methyl-1,2-dihydro-pyrazol-3-one After step D the title compound 4,5-dicyclopropyl-2-(4-fluoro-2-trifluoromethyl-phenyl)-1-methyl-1,2-dihydro-pyrazol-3-one was obtained as a white solid. MS (ESI$^+$): 341.2 ([M+H]$^+$).

Example 11

4,5-Dicyclopropyl-2-(2-methoxy-phenyl)-1-methyl-1,2-dihydro-pyrazol-3-one

This material was obtained in analogy to example 1 using 2-methoxylphenylhydrazine (step A) via the following intermediates:
Step A] 5-Cyclopropyl-2-(2-methoxy-phenyl)-2,4-dihydro-pyrazol-3-one
Step B] 5-Cyclopropyl-2-(2-methoxy-phenyl)-1-methyl-1,2-dihydro-pyrazol-3-one
Step C] 4-Bromo-5-cyclopropyl-2-(2-methoxy-phenyl)-1-methyl-1,2-dihydro-pyrazol-3-one After step D the title compound 4,5-dicyclopropyl-2-(2-methoxy-phenyl)-1-methyl-1,2-dihydro-pyrazol-3-one was obtained as a light orange solid. MS (ESI$^+$): 285.1 ([M+H]$^+$).

Example 12

4,5-Dicyclopropyl-1-methyl-2-naphthalen-1-yl-1,2-dihydro-pyrazol-3-one

This material was obtained in analogy to example 1 using naphthalen-1-yl-hydrazine (step A) via the following intermediates:
Step A] 5-Cyclopropyl-2-naphthalen-1-yl-2,4-dihydro-pyrazol-3-one
Step B] 5-Cyclopropyl-1-methyl-2-naphthalen-1-yl-1,2-dihydro-pyrazol-3-one
Step C] 4-Bromo-5-cyclopropyl-1-methyl-2-naphthalen-1-yl-1,2-dihydro-pyrazol-3-one After step D the title compound 4,5-dicyclopropyl-1-methyl-2-naphthalen-1-yl-1,2-dihydro-pyrazol-3-one was obtained as a beige solid. MS (ESI$^+$): 305.4 ([M+H]$^+$).

Example 13

4,5-Dicyclopropyl-1-ethyl-2-(4-fluoro-phenyl)-1,2-dihydro-pyrazol-3-one

This material was obtained in analogy to example 1 using 4-fluorophenylhydrazine (step A) and iodoethane (step B) via the following intermediates:
Step A] 5-Cyclopropyl-2-(4-fluoro-phenyl)-2,4-dihydro-pyrazol-3-one
Step B] 5-Cyclopropyl-1-ethyl-2-(4-fluoro-phenyl)-1,2-dihydro-pyrazol-3-one
Step C] 4-Bromo-5-cyclopropyl-1-ethyl-2-(4-fluoro-phenyl)-1,2-dihydro-pyrazol-3-one After step D the title compound 4,5-dicyclopropyl-1-ethyl-2-(4-fluoro-phenyl)-1,2-dihydro-pyrazol-3-one was obtained as a light yellow solid. MS (ESI$^+$): 287.1 ([M+H]$^+$).

Example 14

4,5-Dicyclopropyl-1-ethyl-2-(3-fluoro-phenyl)-1,2-dihydro-pyrazol-3-one

This material was obtained in analogy to example 1 using 3-fluorophenylhydrazine (step A) and iodoethane (step B) via the following intermediates:
Step A] 5-Cyclopropyl-2-(3-fluoro-phenyl)-2,4-dihydro-pyrazol-3-one
Step B] 5-Cyclopropyl-1-ethyl-2-(3-fluoro-phenyl)-1,2-dihydro-pyrazol-3-one
Step C] 4-Bromo-5-cyclopropyl-1-ethyl-2-(3-fluoro-phenyl)-1,2-dihydro-pyrazol-3-one After step D the title compound 4,5-dicyclopropyl-1-ethyl-2-(3-fluoro-phenyl)-1,2-dihydro-pyrazol-3-one was obtained as a light yellow solid. MS (ESI$^+$): 287.0 ([M+H]$^+$).

Example 15

2-(2-Chloro-phenyl)-4,5-dicyclopropyl-1-ethyl-1,2-dihydro-pyrazol-3-one

This material was obtained in analogy to example 1 using 2-chlorophenylhydrazine (step A) and iodoethane (step B) via the following intermediates:
Step A] 2-(2-Chloro-phenyl)-5-cyclopropyl-2,4-dihydro-pyrazol-3-one
Step B] 2-(2-Chloro-phenyl)-5-cyclopropyl-1-ethyl-1,2-dihydro-pyrazol-3-one
Step C] 4-Bromo-2-(2-chloro-phenyl)-5-cyclopropyl-1-ethyl-1,2-dihydro-pyrazol-3-one After step D the title compound 2-(2-chloro-phenyl)-4,5-dicyclopropyl-1-ethyl-1,2-dihydro-pyrazol-3-one was obtained as a white solid. MS (ESI$^+$): 303.1 ([M+H]$^+$).

Example 16

2-(3-Chloro-phenyl)-4,5-dicyclopropyl-1-ethyl-1,2-dihydro-pyrazol-3-one

This material was obtained in analogy to example 1 using 3-chlorophenylhydrazine (step A) and iodoethane (step B) via the following intermediates:
Step A] 2-(3-Chloro-phenyl)-5-cyclopropyl-2,4-dihydro-pyrazol-3-one
Step B] 2-(3-Chloro-phenyl)-5-cyclopropyl-1-ethyl-1,2-dihydro-pyrazol-3-one
Step C] 4-Bromo-2-(3-chloro-phenyl)-5-cyclopropyl-1-ethyl-1,2-dihydro-pyrazol-3-one After step D the title compound 2-(3-chloro-phenyl)-4,5-dicyclopropyl-1-ethyl-1,2-dihydro-pyrazol-3-one was obtained as a white solid. MS (ESI$^+$): 303.1 ([M+H]$^+$).

Example 17

4,5-Dicyclopropyl-1-ethyl-2-(2-trifluoromethyl-phenyl)-1,2-dihydro-pyrazol-3-one

This material was obtained in analogy to example 1 using 3-trifluoromethylphenylhydrazine (step A) and iodoethane (step B) via the following intermediates:
Step A] 5-Cyclopropyl-2-(2-trifluoromethyl-phenyl)-2,4-dihydro-pyrazol-3-one
Step B] 5-Cyclopropyl-1-ethyl-2-(2-trifluoromethyl-phenyl)-1,2-dihydro-pyrazol-3-one
Step C] 4-Bromo-5-cyclopropyl-1-ethyl-2-(2-trifluoromethyl-phenyl)-1,2-dihydro-pyrazol-3-one After step D the title compound 4,5-dicyclopropyl-1-ethyl-2-(2-trifluoromethyl-phenyl)-1,2-dihydro-pyrazol-3-one was obtained as a light yellow solid. MS (ESI$^+$): 337.4 ([M+H]$^+$).

Example 18

Benzyl-4,5-dicyclopropyl-2-(2-trifluoromethyl-phenyl)-1,2-dihydro-pyrazol-3-one

This material was obtained in analogy to example 1 using 3-trifluoromethylphenylhydrazine (step A) and benzylbromide (step B) via the following intermediates:
Step A] 5-Cyclopropyl-2-(2-trifluoromethyl-phenyl)-2,4-dihydro-pyrazol-3-one
Step B] 1-Benzyl-5-cyclopropyl-2-(2-trifluoromethyl-phenyl)-1,2-dihydro-pyrazol-3-one
Step C] 1-Benzyl-4-bromo-5-cyclopropyl-2-(2-trifluoromethyl-phenyl)-1,2-dihydro-pyrazol-3-one After step D the title compound 1-benzyl-4,5-dicyclopropyl-2-(2-trifluoromethyl-phenyl)-1,2-dihydro-pyrazol-3-one was obtained as a light yellow solid. MS (ESI$^+$): 399.1 ([M+H]$^+$).

Example 19

4,5-Dicyclopropyl-1-cyclopropylmethyl-2-(2-trifluoromethyl-phenyl)-1,2-dihydro-pyrazol-3-one This material was obtained in analogy to example 1 using 3-trifluoromethylphenylhydrazine (step A) and bromomethyl-cyclopropane (step B) via the following intermediates:
Step A] 5-Cyclopropyl-2-(2-trifluoromethyl-phenyl)-2,4-dihydro-pyrazol-3-one
Step B] 5-Cyclopropyl-1-cyclopropylmethyl-2-(2-trifluoromethyl-phenyl)-1,2-dihydro-pyrazol-3-one
Step C] 4-Bromo-5-cyclopropyl-1-cyclopropylmethyl-2-(2-trifluoromethyl-phenyl)-1,2-dihydro-pyrazol-3-one After step D the title compound 4,5-dicyclopropyl-1-cyclopropylmethyl-2-(2-trifluoromethyl-phenyl)-1,2-dihydro-pyrazol-3-one was obtained as a light brown solid. MS (ESI$^+$): 363.3 ([M+H]$^+$).

Example 20

Benzyl-4,5-dicyclopropyl-1-methyl-1,2-dihydro-pyrazol-3-one

This material was obtained in analogy to example 1 using benzylhydrazine (step A) and iodomethane (step B) via the following intermediates:
Step A] 2-Benzyl-5-cyclopropyl-2,4-dihydro-pyrazol-3-one
Step B] 2-Benzyl-5-cyclopropyl-1-methyl-1,2-dihydro-pyrazol-3-one
Step C] 2-Benzyl-4-bromo-5-cyclopropyl-1-methyl-1,2-dihydro-pyrazol-3-one After step D the title compound 2-benzyl-4,5-dicyclopropyl-1-methyl-1,2-dihydro-pyrazol-3-one was obtained as a light yellow solid. MS (ESI$^+$): 269.5 ([M+H]$^+$).

Example 21

2,3-Dicyclopropyl-6,7,8,9-tetrahydro-5H-pyrazolo[1,2-a][1,2]diazepin-1-one

Step A] 3-Cyclopropyl-6,7,8,9-tetrahydro-5H-pyrazolo[1,2-a][1,2]diazepin-1-one
This material was obtained in analogy to example 49 using 5-cyclopropyl-1,2-dihydro-pyrazol-3-one (see Example 52, step A) and 1,5-dibromopentane to give 3-cyclopropyl-6,7,8,9-tetrahydro-5H-pyrazolo[1,2-a][1,2]diazepin-1-one as a white solid. MS (ESI$^+$): 193.5 [M+H]$^+$).

Step B] 2-Bromo-3-cyclopropyl-6,7,8,9-tetrahydro-5H-pyrazolo[1,2-a][1,2]diazepin-1-one
This material was obtained in analogy to example 1, step C, using 3-cyclopropyl-6,7,8,9-tetrahydro-5H-pyrazolo[1,2-a][1,2]diazepin-1-one to give 2-bromo-3-cyclopropyl-6,7,8,9-tetrahydro-5H-pyrazolo[1,2-a][1,2]diazepin-1-one as a light brown solid. MS (ESI$^+$): 271.3 [M+H]$^+$).
Step C] 2,3-Dicyclopropyl-6,7,8,9-tetrahydro-5H-pyrazolo[1,2-a][1,2]diazepin-1-one
This material was obtained in analogy to example 1, step D, using 2-bromo-3-cyclopropyl-6,7,8,9-tetrahydro-5H-pyrazolo[1,2-a][1,2]diazepin-1-one to give 2,3-dicyclopropyl-6,7,8,9-tetrahydro-5H-pyrazolo[1,2-a][1,2]diazepin-1-one as a light brown solid. MS (ESI$^+$): 233.2 [M+H]$^+$).

Example 22

5-Cyclobutyl-4-cyclopropyl-1-methyl-2-phenyl-1,2-dihydro-pyrazol-3-one

This material was obtained in analogy to example 1 using 3-cyclobutyl-3-oxo-propionic acid methyl ester (step A) via the following intermediates:
Step A] 5-Cyclobutyl-2-phenyl-2,4-dihydro-pyrazol-3-one
Step B] 5-Cyclobutyl-1-methyl-2-phenyl-1,2-dihydro-pyrazol-3-one
Step C] 4-Bromo-5-cyclobutyl-1-methyl-2-phenyl-1,2-dihydro-pyrazol-3-one After step D the title compound 5-cyclobutyl-4-cyclopropyl-1-methyl-2-phenyl-1,2-dihydro-pyrazol-3-one was obtained as a light yellow solid. MS (ESI$^+$): 269.5 ([M+H]$^+$).

Example 23

5-Cyclobutyl-4-cyclopropyl-1-methyl-2-(2-trifluoromethyl-phenyl)-1,2-dihydro-pyrazol-3-one This material was obtained in analogy to example 1 using 3-cyclobutyl-3-oxo-propionic acid methyl ester and 2-trifluoromethylphenylhydrazine (step A) via the following intermediates:
Step A] 5-Cyclobutyl-2-(2-trifluoromethyl-phenyl)-2,4-dihydro-pyrazol-3-one
Step B] 5-Cyclobutyl-1-methyl-2-(2-trifluoromethyl-phenyl)-1,2-dihydro-pyrazol-3-one
Step C] 4-Bromo-5-cyclobutyl-1-methyl-2-(2-trifluoromethyl-phenyl)-1,2-dihydro-pyrazol-3-one After step D the title compound 5-cyclobutyl-4-cyclopropyl-1-methyl-2-(2-trifluoromethyl-phenyl)-1,2-dihydro-pyrazol-3-one was obtained as a light yellow solid. MS (ESI$^+$): 337.4 ([M+H]$^+$).

Example 24

Cyclopropyl-1-methyl-5-(1-methyl-cyclopropyl)-2-(2-trifluoromethyl-phenyl)-1,2-dihydro-pyrazol-3-one This material was obtained in analogy to example 1 using 3-(1-methyl-cyclopropyl)-3-oxo-propionic acid methyl ester (obtained according to *J. Am. Chem. Soc.* 1968, 90, 2882-2889) and 2-trifluoromethylphenylhydrazine (step A) via the following intermediates:
Step A] 5-(1-Methyl-cyclopropyl)-2-(2-trifluoromethyl-phenyl)-2,4-dihydro-pyrazol-3-one
Step B] 1-Methyl-5-(1-methyl-cyclopropyl)-2-(2-trifluoromethyl-phenyl)-1,2-dihydro-pyrazol-3-one Step C] 4-Bromo-1-methyl-5-(1-methyl-cyclopropyl)-2-(2-trifluoromethyl-phenyl)-1,2-dihydro-pyrazol-3-one After step D the title compound 4-cyclopropyl-1-methyl-5-(1-methyl-cyclopropyl)-2-(2-trifluoromethyl-phenyl)-1,2-dihydro-pyrazol-3-one was obtained as a light yellow solid. MS (ESI$^+$): 337.3 ([M+H]$^+$).

Example 25 tert-Butyl-4-cyclopropyl-1-methyl-2-(2-trifluoromethyl-phenyl)-1,2-dihydro-pyrazol-3-one This material was obtained in analogy to example 1 using 4,4-dimethyl-3-oxo-pentanoic acid methyl ester and 2-trifluoromethylphenylhydrazine (step A) via the following intermediates:
Step A] 5-tert-Butyl-2-(2-trifluoromethyl-phenyl)-2,4-dihydro-pyrazol-3-one
Step B] 5-tert-Butyl-1-methyl-2-(2-trifluoromethyl-phenyl)-1,2-dihydro-pyrazol-3-one
Step C] 4-Bromo-5-tert-butyl-1-methyl-2-(2-trifluoromethyl-phenyl)-1,2-dihydro-pyrazol-3-one After step D the title compound 5-tert-butyl-4-cyclopropyl-1-methyl-2-(2-trifluoromethyl-phenyl)-1,2-dihydro-pyrazol-3-one was obtained as a light yellow solid. MS (ESI$^+$): 339.2 ([M+H]$^+$).

Example 26

Cyclopropyl-5-(2,2-dimethyl-cyclopropyl)-1-methyl-2-(2-trifluoromethyl-phenyl)-1,2-dihydro-pyrazol-3-one Step A] 3-(2,2-Dimethyl-cyclopropyl)-3-oxo-propionic acid ethyl ester This compound was prepared in analogy to *J. Am. Chem. Soc.* 1968, 90, 2882-2889 using 1-(2,2-dimethyl-cyclopropyl)-ethanone (obtained according to *J. Org. Chem.* 1970, 35, 374-379) to give a racemic mixture of 3-(2,2-dimethyl-cyclopropyl)-3-oxo-propionic acid ethyl ester as a pale yellow oil.
Step B] 4-Cyclopropyl-5-(2,2-dimethyl-cyclopropyl)-1-methyl-2-(2-trifluoromethyl-phenyl)-1,2-dihydro-pyrazol-3-one This material was obtained in analogy to example 1 using 3-(2,2-dimethyl-cyclopropyl)-3-oxo-propionic acid methyl ester and 2-trifluoromethylphenylhydrazine (step A) via the following intermediates:
Step A] 5-(2,2-Dimethyl-cyclopropyl)-2-(2-trifluoromethyl-phenyl)-2,4-dihydro-pyrazol-3-one
Step B] 5-(2,2-Dimethyl-cyclopropyl)-1-methyl-2-(2-trifluoromethyl-phenyl)-1,2-dihydro-pyrazol-3-one
Step C] 4-Bromo-5-(2,2-dimethyl-cyclopropyl)-1-methyl-2-(2-trifluoromethyl-phenyl)-1,2-dihydro-pyrazol-3-one After step D the title compound 4-cyclopropyl-5-(2,2-dimethyl-cyclopropyl)-1-methyl-2-(2-trifluoromethyl-phenyl)-1,2-dihydro-pyrazol-3-one was obtained as a yellow solid. MS (ESI$^+$): 351.4 ([M+H]$^+$).

Example 27

Cyclopropyl-1-phenyl-4,5,6,7-tetrahydro-pyrazolo[1,5-a]pyridin-2-one

Step A] 7-Bromo-3-oxo-heptanoic acid methyl ester

A round bottom flask equipped with a magnetic stir bar was flushed with argon and charged with THF (40 mL) and LDA solution (17.2 mL of a 2M solution in THF) at −78° C. To this was added 3-oxo-butyric acid methyl ester (2 g) dissolved in THF (5 mL) dropwise. The solution is then warmed to 0° C. and 1,3-dibromopropane (3.47 g) was added via syringe dissolved in THF (5 mL). The reaction was stirred for 1 hour and then quenched with 10 mL of 2N aqueous HCl solution and extracted with ether, and the combined organic phases were washed with water, aqueous sodium bicarbonate solution and brine. Drying over sodium sulfate, filtration and evaporation of the volatiles in vacuo afforded a crude oil. Flash column chromatography via ISCO Combiflash chromatography (EtOAc/heptane) afforded the desired 7-bromo-3-oxo-heptanoic acid methyl ester (0.9 g) as a yellow oil. MS (ESI+): 251.1 [M+H]$^+$).
Step B] 1-Phenyl-4,5,6,7-tetrahydro-pyrazolo[1,5-a]pyridin-2-one To a solution of 7-bromo-3-oxo-heptanoic acid methyl ester (0.35 g) in ethanol (80 mL) in a round bottom flask under argon was added phenylhydrazine (0.16 g). The mixture was immersed into an oil bath and heated to 120° C. overnight. The reaction vessel was then cooled and the acetic acid was evaporated in vacuo and the remaining solid was dissolved in EtOAc and water. The phases were separated and the aqueous phase was extracted with further EtOAc. The combined organic phases were washed with brine, dried over sodium sulfate, filtered and evaporated in vacuo and azeotroped with toluene (2×). The crude residue was then purified via trituration with a 1:1 mixture of ether/pentane to afford the desired 1-phenyl-4,5,6,7-tetrahydro-pyrazolo[1,5-a]pyridin-2-one (0.21 g) as a light brown solid. MS (ESI$^+$): 215.4 ([M+H]$^+$).
Step C] 3-Bromo-1-phenyl-4,5,6,7-tetrahydro-pyrazolo[1,5-a]pyridin-2-one To a solution of 1-phenyl-4,5,6,7-tetrahydro-pyrazolo[1,5-a]pyridin-2-one (0.21 g) in methylene chloride (4 mL) was added N-bromosuccinimide (0.18 g). The reaction vessel was wrapped in aluminium foil and stirred for 24 hours. The solvent was evaporated in vacuo and the residue was dissolved in EtOAc and water. The phases were separated and the aqueous phase was extracted with more EtOAc. The combined organic phases were washed with brine, dried over sodium sulfate, filtered and reduced in vacuo to give a crude residue. Flash column chromatography over silica gel using ISCO combiflash chromatography and eluting with EtOAc/heptane afforded the desired 3-bromo-1-phenyl-4,5,6,7-tetrahydro-pyrazolo[1,5-a]pyridin-2-one (0.15 g) as a light brown solid. MS (ESI$^+$): 295.2 ([M+H]$^+$).
Step D] 3-Cyclopropyl-1-phenyl-4,5,6,7-tetrahydro-pyrazolo[1,5-a]pyridin-2-one Into a sealable tube under argon was added 3-bromo-1-phenyl-4,5,6,7-tetrahydro-pyrazolo[1,5-a]pyridin-2-one (0.11 g), cyclopropylboronic acid (0.064 g), potassium phosphate (0.43 g), tricyclohexyl phosphine (0.016 g) and toluene (1 mL) and water (0.1 mL). To this was added palladium acetate (0.006 g) and the tube was sealed and stirred at 100° C. for 2 days. The reaction vessel was then cooled and the diluted with water/EtOAc. The phases were separated and the aqueous phase was extracted with further EtOAc. The combined organic phases were washed with brine, dried over sodium sulfate and evaporated in vacuo to afford a crude residue. Flash column chromatography over silica gel using ISCO combiflash chromatography and eluting with EtOAc/heptane afforded the desired 3-cyclopropyl-1-phenyl-4,5,6,7-tetrahydro-pyrazolo[1,5-a]pyridin-2-one as a light yellow solid. MS (ESI+): 255.4 ([M+H]+).

Example 28

Cyclopropyl-5-(4-fluoro-phenoxymethyl)-1-methyl-2-phenyl-1,2-dihydro-pyrazol-3-one Step A] 4-Cyclopropyl-1,5-dimethyl-2-phenyl-1,2-dihydro-pyrazol-3-one This compound was obtained in analogy to example 29 (step A and B) using 3-oxo-butyric acid methyl ester and phenylhydrazine (step A) to give 4-cyclopropyl-1,5-dimethyl-2-phenyl-1,2-dihydro-pyrazol-3-one as a light yellow solid. MS (ESI+): 229.5 ([M+H]+).

Step B] 5-Bromomethyl-4-cyclopropyl-1-methyl-2-phenyl-1,2-dihydro-pyrazol-3-one

To 4-cyclopropyl-1,5-dimethyl-2-phenyl-1,2-dihydro-pyrazol-3-one (0.081 g) in a round bottom flask under argon in dioxane (1.5 mL) was added bromine (0.057 g). The reaction was stirred at ambient temperature for 2 days. The reaction was diluted with water and EtOAc and the phases were separated. The aqueous phase was extracted with more EtOAc and the combined organic phases were washed with brine, dried over sodium sulfate, filtered and evaporated in vacuo. The crude material was purified via ISCO combiflash chromatography (EtOAc/heptane) to afford the desired 5-Bromomethyl-4-cyclopropyl-1-methyl-2-phenyl-1,2-dihydro-pyrazol-3-one as a light brown solid. MS (ESI+): 307.1 ([M+H]+).

Step C] 4-Cyclopropyl-5-(4-fluoro-phenoxymethyl)-1-methyl-2-phenyl-1,2-dihydro-pyrazol-3-one To a solution of 5-bromomethyl-4-cyclopropyl-1-methyl-2-phenyl-1,2-dihydro-pyrazol-3-one (0.094 g) in acetonitrile (5 mL), was added 4-fluorophenol (0.034 g), caesium carbonate (0.1 g) and potassium iodide (3 crystals). The reaction was stirred overnight at ambient temperature and was then diluted with water and EtOAc. The phases were separated and the aqueous was extracted with further EtOAc. The combined organic phases were washed with further HCl solution, brine and dried with sodium sulfate. Filtration and evaporation of the volatiles in vacuo afforded the desired 4-cyclopropyl-5-(4-fluoro-phenoxymethyl)-1-methyl-2-phenyl-1,2-dihydro-pyrazol-3-one (0.023 g) as a light beige solid. MS (ESI+): 339.1 ([M+H]+).

Example 29

Cyclopropyl-5-(4-fluoro-phenoxymethyl)-2-(4-fluoro-phenyl)-1-methyl-1,2-dihydro-pyrazol-3-one Step A] 2-(4-Fluoro-phenyl)-5-methyl-2,4-dihydro-pyrazol-3-one To a solution of 3-oxo-butyric acid methyl ester (2.8 g) in acetic acid (6.5 mL) in a round bottom flask under argon was added 4-fluorophenylhydrazine (3.05 g). The mixture was immersed into an oil bath and heated to 120° C. overnight. The reaction vessel was then cooled and the acetic acid was evaporated in vacuo and the remaining solid was dissolved in EtOAc and water. The phases were separated and the aqueous phase was extracted with further EtOAc. The combined organic phases were washed with brine, dried over sodium sulfate, filtered and evaporated in vacuo and azeotroped with toluene (2×). The crude residue was then purified via ISCO Combiflash chromatography using EtOAc/heptane as eluent to afford the desired 2-(4-fluoro-phenyl)-5-methyl-2,4-dihydro-pyrazol-3-one (3.2 g) as a beige solid. MS (ESI+): 193.3 ([M+H]+).

Step B] 2-(4-Fluoro-phenyl)-1,5-dimethyl-1,2-dihydro-pyrazol-3-one

To a solution of 2-(4-fluoro-phenyl)-5-methyl-2,4-dihydro-pyrazol-3-one (1 g) in DMF (5 mL) was added iodomethane (0.33 mL) and the mixture was placed into a pressure bomb and sealed. The reaction vessel was then heated in an oil bath to 100° C. over two days. The reaction vessel was then cooled and the DMF was evaporated in vacuo. The residue was dissolved in EtOAc and saturated and washed with saturated sodium bicarbonate solution. The phases were separated and the aqueous solution was extracted with EtOAc another two times at neutral pH. The combined organic phases were washed with brine, dried over sodium sulfate, filtered and evaporated in vacuo to afford a crude residue. Flash column chromatography over silica gel using ISCO combiflash chromatography and eluting with EtOAc/heptane and 3% AcOH afforded the desired 2-(4-fluoro-phenyl)-1,5-dimethyl-1,2-dihydro-pyrazol-3-one (0.5 g) as a light brown solid. MS (ESI+): 207.1 ([M+H]+).

Step C] 4-Bromo-2-(4-fluoro-phenyl)-1,5-dimethyl-1,2-dihydro-pyrazol-3-one

To a solution of 2-(4-fluoro-phenyl)-1,5-dimethyl-1,2-dihydro-pyrazol-3-one (0.5 g) in methylene chloride (10 mL) was added N-bromosuccinimide (0.43 g). The reaction vessel was wrapped in aluminium foil and stirred for 24 hours. The solvent was evaporated in vacuo and the residue was dissolved in EtOAc and water. The phases were separated and the aqueous phase was extracted with more EtOAc. The combined organic phases were washed with brine, dried over sodium sulfate, filtered and reduced in vacuo to give a crude residue. Flash column chromatography over silica gel using ISCO combiflash chromatography and eluting with EtOAc/heptane afforded the desired 4-bromo-2-(4-fluoro-phenyl)-1,5-dimethyl-1,2-dihydro-pyrazol-3-one (0.43 g) as an off-white solid. MS (ESI+): 287.0 ([M+H]+).

Step D] 4-Cyclopropyl-2-(4-fluoro-phenyl)-1,5-dimethyl-1,2-dihydro-pyrazol-3-one Into a sealable tube under argon was added 4-bromo-2-(4-fluoro-phenyl)-1,5-dimethyl-1,2-dihydro-pyrazol-3-one (0.439 g), cyclopropylboronic acid (0.265 g), potassium phosphate (1.75 g), tricyclohexyl phosphine (0.065 g), toluene (3 mL) and water (0.35 mL). To this was added palladium acetate (0.024 g) and the tube was sealed and stirred at 100° C. for 2 days. The reaction vessel was then cooled and then diluted with water/EtOAc. The phases were separated and the aqueous phase was extracted with further EtOAc. The combined organic phases were washed with brine, dried over sodium sulfate and evaporated in vacuo to afford a crude residue. Flash column chromatography over silica gel using ISCO combiflash chromatography and eluting with EtOAc/heptane afforded the desired 4-cyclopropyl-2-(4-fluoro-phenyl)-1,5-dimethyl-1,2-dihydro-pyrazol-3-one as a beige solid. MS (ESI+): 247.1 ([M+H]+).

Step E] 5-Bromomethyl-4-cyclopropyl-2-(4-fluoro-phenyl)-1-methyl-1,2-dihydro-pyrazol-3-one To 4-cyclopropyl-2-(4-fluoro-phenyl)-1,5-dimethyl-1,2-dihydro-pyrazol-3-one (0.32 g) in a round bottom flask under argon in dioxane (5 mL) was added bromine (0.20 g). The reaction was stirred at ambient temperature for 2 days. The reaction was diluted with water and EtOAc and the phases were separated. The aqueous phase was extracted with more EtOAc and the combined organic phases were washed with brine, dried over sodium sulfate, filtered and evaporated in vacuo. The crude material was purified via ISCO combiflash chromatography (EtOAc/heptane) to afford the desired 5-bromomethyl-4-cyclopropyl-2-(4-fluoro-phenyl)-1-methyl-1,2-dihydro-pyrazol-3-one as a light brown solid. MS (ESI$^+$): 327.1 ([M+H]$^+$).

Step F] 4-cyclopropyl-5-(4-fluoro-phenoxymethyl)-2-(4-fluoro-phenyl)-1-methyl-1,2-dihydro-pyrazol-3-one To a solution of 5-bromomethyl-4-cyclopropyl-2-(4-fluoro-phenyl)-1-methyl-1,2-dihydro-pyrazol-3-one (0.130 g) in acetonitrile (5 mL), was added 4-fluorophenol (0.045 g), caesium carbonate (0.13 g) and potassium iodide (3 crystals). The reaction was stirred overnight at ambient temperature and was then diluted with water and EtOAc. The phases were separated and the aqueous was extracted with further EtOAc. The combined organic phases were washed with further HCl solution, brine and dried with sodium sulfate. Filtration and evaporation of the volatiles in vacuo and purification of the residue via ISCO Combiflash chromatography (using EtOAc/heptane) afforded the desired 4-cyclopropyl-5-(4-fluoro-phenoxymethyl)-2-(4-fluoro-phenyl)-1-methyl-1,2-dihydro-pyrazol-3-one (0.023 g) as a light beige solid. MS (ESI$^+$): 357.0 ([M+H]$^+$).

Example 30

N-{4-[4-Cyclopropyl-1-(4-fluoro-phenyl)-2-methyl-5-oxo-2,5-dihydro-1H-pyrazol-3-ylmethoxy]-phenyl}-acetamide This material was obtained in analogy to example 29 using N-(4-hydroxy-phenyl)-acetamide (step F) to afford N-{4-[4-cyclopropyl-1-(4-fluoro-phenyl)-2-methyl-5-oxo-2,5-dihydro-1H-pyrazol-3-ylmethoxy]-phenyl}-acetamide as a beige solid. MS (ESI$^+$): 396.3 [M+H]$^+$).

Example 31

N-{4-[4-Cyclopropyl-1-(2-fluoro-phenyl)-2-methyl-5-oxo-2,5-dihydro-1H-pyrazol-3-ylmethoxy]-phenyl}-acetamide This material was obtained in analogy to example 29 using 2-fluorophenylhydrazine (step A) and N-(4-hydroxy-phenyl)-acetamide (step F) via the following intermediates:
Step A] 2-(2-Fluoro-phenyl)-5-methyl-2,4-dihydro-pyrazol-3-one
Step B] 2-(2-Fluoro-phenyl)-1,5-dimethyl-1,2-dihydro-pyrazol-3-one
Step C] 4-Bromo-2-(2-fluoro-phenyl)-1,5-dimethyl-1,2-dihydro-pyrazol-3-one
Step D] 4-Cyclopropyl-2-(2-fluoro-phenyl)-1,5-dimethyl-1,2-dihydro-pyrazol-3-one
Step E] 5-Bromomethyl-4-cyclopropyl-2-(2-fluoro-phenyl)-1-methyl-1,2-dihydro-pyrazol-3-one After step F the title compound N-{4-[4-cyclopropyl-1-(2-fluoro-phenyl)-2-methyl-5-oxo-2,5-dihydro-1H-pyrazol-3-ylmethoxy]-phenyl}-acetamide was obtained as a beige solid. MS (ESI$^+$): 396.3 [M+H]$^+$).

Example 32

4-Cyclopropyl-5-(4-fluoro-phenoxymethyl)-2-(2-fluoro-phenyl)-1-methyl-1,2-dihydro-pyrazol-3-one This material was obtained in analogy to example 29 using 2-fluorophenylhydrazine (step A) to give 4-cyclopropyl-5-(4-fluoro-phenoxymethyl)-2-(2-fluoro-phenyl)-1-methyl-1,2-dihydro-pyrazol-3-one was obtained as a beige solid. MS (ESI$^+$): 357.1 [M+H]$^+$).

Example 33

4-Cyclopropyl-2-(4-fluoro-phenyl)-5-[2-(4-fluoro-phenyl)-ethyl]-1-methyl-1,2-dihydro-pyrazol-3-one Step A] 5-(4-Fluoro-phenyl)-3-oxo-pentanoic acid methyl ester To a solution of lithium diisopropyl amide solution (17.2 mL of a 2 M solution in THF/hexane/ethylbenzene) in THF (50 mL) in a dry round bottom flask flushed with argon was added at −78° C. 3-oxo-butyric acid methyl ester (2.0 g) dissolved in THF (5 mL) dropwise. The solution was then warmed to 0° C. and a solution of 4-fluorobenzylbromide was added in THF (5 mL) rapidly via syringe. The reaction was allowed to stir a further 1 hour at 0° C. and was then quenched with 1N aqueous HCl solution. The mixture was extracted with EtOAc (3x) and the combined organic phases were washed with water, saturated sodium bicarbonate solution and brine and dried over sodium sulfate. Filtration and evaporation of the volatiles in vacuo afforded a crude residue which was purified via ISCO combiflash chromatography to afford the desired 5-(4-fluoro-phenyl)-3-oxo-pentanoic acid methyl ester (0.87 g) as a pale yellow oil. MS (ESI$^+$): 225.3 [M+H]$^+$).
Step B] 2-(4-Fluoro-phenyl)-5-[2-(4-fluoro-phenyl)-ethyl]-2,4-dihydro-pyrazol-3-one To a solution of 5-(4-fluoro-phenyl)-3-oxo-pentanoic acid methyl ester (0.43 g) in acetic acid (5 mL) in a sealable tube was added 4-fluorophenylhydrazine.HCl (0.31 g). The reaction vessel was sealed and immersed into an oil bath at 100° C. for 18 hours. The reaction vessel was cooled to ambient temperature, opened and the contents were poured onto a mixture of EtOAc and water. The aqueous phase was extracted with EtOAc and the combined organic phases were washed with water and dried over sodium sulfate. Filtration and evaporation of the volatiles in vacuo afforded a crude crystalline material. The crude product was washed with ether to afford the desired 2-(4-fluoro-phenyl)-5-[2-(4-fluoro-phenyl)-ethyl]-2,4-dihydro-pyrazol-3-one (0.37 g) as a beige crystalline solid. MS (ESI$^+$): 301.1 [M+H]$^+$).
Step C] 2-(4-Fluoro-phenyl)-5-[2-(4-fluoro-phenyl)-ethyl]-1-methyl-1,2-dihydro-pyrazol-3-one To a solution of 2-(4-fluoro-phenyl)-5-[2-(4-fluoro-phenyl)-ethyl]-2,4-dihydro-pyrazol-3-one (0.34 g) in DMF (2 mL) was added iodomethane (0.07 mL) and the mixture was placed into a pressure bomb and sealed. The reaction vessel was then heated in an oil bath to 100° C. over two days. The reaction vessel was then cooled and the DMF was evaporated in vacuo. The residue was dissolved in EtOAc and saturated and washed with saturated sodium bicarbonate solution. The phases were separated and the aqueous solution was extracted with EtOAc another two times at neutral pH. The combined organic phases were washed with brine, dried over sodium sulfate, filtered and evaporated in vacuo to afford a crude residue. Flash column chromatography over silica gel using ISCO combiflash chromatography and eluting with EtOAc/heptane afforded the desired 2-(4-fluoro-phenyl)-5-[2-(4-fluoro-phenyl)-ethyl]-1-methyl-1,2-dihydro-pyrazol-3-one (0.296 g) as a light brown solid. MS (ESI$^+$): 315.1 ([M+H]$^+$).
Step D] 4-Bromo-2-(4-fluoro-phenyl)-5-[2-(4-fluoro-phenyl)-ethyl]-1-methyl-1,2-dihydro-pyrazol-3-one To a solution of 2-(4-fluoro-phenyl)-5-[2-(4-fluoro-phenyl)-ethyl]-1-methyl-1,2-dihydro-pyrazol-3-one (0.296 g) in methylene chloride (5 mL) was added N-bromosuccinimide (0.168 g). The reaction vessel was wrapped in aluminium foil and stirred for 24 hours. The solvent was evaporated in vacuo and the residue was dissolved in EtOAc and water. The phases were separated and the aqueous phase was extracted with more EtOAc. The combined organic phases were washed with brine, dried over sodium sulfate, filtered and reduced in vacuo to give a crude residue. Flash column chromatography over silica gel using ISCO combiflash chromatography and eluting with EtOAc/heptane afforded the desired 4-bromo-2-(4-fluoro-phenyl)-5-[2-(4-fluoro-phenyl)-ethyl]-1-methyl-1,2-dihydro-pyrazol-3-one (0.312 g) as a white solid. MS (ESI$^+$): 395.0 ([M+H]$^+$).

Step E] 4-Cyclopropyl-2-(4-fluoro-phenyl)-5-[2-(4-fluoro-phenyl)-ethyl]-1-methyl-1,2-dihydro-pyrazol-3-one Into a sealable tube under argon was added 4-bromo-2-(4-fluoro-phenyl)-5-[2-(4-fluoro-phenyl)-ethyl]-1-methyl-1,2-dihydro-pyrazol-3-one (0.312 g), cyclopropylboronic acid (0.139 g), potassium phosphate (0.924 g), tricyclohexyl phosphine (0.034 g) and toluene (3.0 mL). To this was added palladium acetate (0.013 g) and the tube was sealed and stirred at 100° C. for 20 hours. The reaction vessel was then cooled and the diluted with water/EtOAc. The phases were separated and the aqueous phase was extracted with further EtOAc. The combined organic phases were washed with brine, dried over sodium sulfate and evaporated in vacuo to afford a crude residue. Flash column chromatography over silica gel using ISCO combiflash chromatography and eluting with EtOAc/heptane afforded the desired 4-cyclopropyl-2-(4-fluoro-phenyl)-5-[2-(4-fluoro-phenyl)-ethyl]-1-methyl-1,2-dihydro-pyrazol-3-one (0.055 g) as a white crystalline solid. MS (ESI$^+$): 315.1 ([M+H]$^+$).

Example 34

4-Cyclopropyl-2-(2-fluoro-phenyl)-5-[2-(4-fluoro-phenyl)-ethyl]-1-methyl-1,2-dihydro-pyrazol-3-one This material was obtained in analogy to example 33 using 2-fluorophenylhydrazine (step B) via the following intermediates:
Step B] 2-(2-Fluoro-phenyl)-5-[2-(4-fluoro-phenyl)-ethyl]-2,4-dihydro-pyrazol-3-one
Step C] 2-(2-Fluoro-phenyl)-5-[2-(4-fluoro-phenyl)-ethyl]-1-methyl-1,2-dihydro-pyrazol-3-one
Step D] 4-Bromo-2-(2-fluoro-phenyl)-5-[2-(4-fluoro-phenyl)-ethyl]-1-methyl-1,2-dihydro-pyrazol-3-one After step E the title compound 4-cyclopropyl-2-(2-fluoro-phenyl)-5-[2-(4-fluoro-phenyl)-ethyl]-1-methyl-1,2-dihydro-pyrazol-3-one was obtained as an off-white solid. MS (ESI$^+$): 355.1 [M+H]$^+$).

Example 35

4-Cyclopropyl-1-ethyl-5-(4-fluoro-phenoxymethyl)-2-(4-fluoro-phenyl)-1,2-dihydro-pyrazol-3-one This material was obtained in analogy to example 29 using iodoethane (step B) via the following intermediates:
Step B] 1-Ethyl-2-(4-fluoro-phenyl)-5-methyl-1,2-dihydro-pyrazol-3-one
Step C] 4-Bromo-1-ethyl-2-(4-fluoro-phenyl)-5-methyl-1,2-dihydro-pyrazol-3-one
Step D] 4-Cyclopropyl-1-ethyl-2-(4-fluoro-phenyl)-5-methyl-1,2-dihydro-pyrazol-3-one
Step E] 5-Bromomethyl-4-cyclopropyl-1-ethyl-2-(4-fluoro-phenyl)-1,2-dihydro-pyrazol-3-one After step F the title compound 4-cyclopropyl-1-ethyl-5-(4-fluoro-phenoxymethyl)-2-(4-fluoro-phenyl)-1,2-dihydro-pyrazol-3-one was obtained as beige solid. MS (ESI$^+$): 371.4 [M+H]$^+$).

Example 36

5-(4-Chloro-phenoxymethyl)-4-isopropyl-1-methyl-2-phenyl-1,2-dihydro-pyrazol-3-one Step A] 5-Bromomethyl-4-isopropyl-1-methyl-2-phenyl-1,2-dihydro-pyrazol-3-one To 4-isopropyl-1,5-dimethyl-2-phenyl-1,2-dihydro-pyrazol-3-one (0.8 g) in a round bottom flask under argon in dioxane (15 mL) was added bromine (0.55 g). The reaction was stirred at ambient temperature for 5 hours. The reaction was diluted with water and EtOAc and the phases were separated. The aqueous phase was extracted with more EtOAc and the combined organic phases were washed with brine, dried over sodium sulfate, filtered and evaporated in vacuo. The crude material was purified via ISCO combiflash chromatography (EtOAc/heptane) to afford the desired 5-bromomethyl-4-isopropyl-1-methyl-2-phenyl-1,2-dihydro-pyrazol-3-one as a light brown solid. MS (ESI$^+$): 309.3 ([M+H]$^+$).

Step B] 5-(4-Chloro-phenoxymethyl)-4-isopropyl-1-methyl-2-phenyl-1,2-dihydro-pyrazol-3-one To a suspension of sodium hydride (0.023 g of a 50% dispersion in mineral oil) in DMF (2 mL) at 0° C. was added 4-chlorophenol (0.042 g). To this was added a solution of 5-bromomethyl-4-isopropyl-1-methyl-2-phenyl-1,2-dihydro-pyrazol-3-one (0.10 g) in DMF (1 mL) and the reaction mixture was allowed to stir at ambient temperature for 18 hours. The reaction was then diluted with water and EtOAc. The phases were separated and the aqueous was extracted with further EtOAc. The combined organic phases were washed with further brine and dried with sodium sulfate. Filtration and evaporation of the volatiles in vacuo and purification of the residue via ISCO Combiflash chromatography (using EtOAc/heptane) afforded the 5-(4-chloro-phenoxymethyl)-4-isopropyl-1-methyl-2-phenyl-1,2-dihydro-pyrazol-3-one (0.020 g) as a light yellow solid. MS (ESI$^+$): 357.1 [M+H]$^+$).

Example 37

5-(2,4-Dichloro-phenoxymethyl)-4-isopropyl-1-methyl-2-phenyl-1,2-dihydro-pyrazol-3-one This compound was obtained in analogy to example 36, using 2,4-dichlorophenol (step B) to give 5-(2,4-dichloro-phenoxymethyl)-4-isopropyl-1-methyl-2-phenyl-1,2-dihydro-pyrazol-3-one as a white solid. MS (ESI$^+$): 392.0 [M+H]$^+$).

Example 38

5-(4-Fluoro-phenoxymethyl)-4-isopropyl-1-methyl-2-phenyl-1,2-dihydro-pyrazol-3-one This compound was obtained in analogy to example 36, using 4-flourophenol (step B) to give 5-(4-fluoro-phenoxymethyl)-4-isopropyl-1-methyl-2-phenyl-1,2-dihydro-pyrazol-3-one as a white solid. MS (ESI$^+$): 341.3 [M+H]$^+$).

Example 39

5-(2-Chloro-phenoxymethyl)-4-isopropyl-1-methyl-2-phenyl-1,2-dihydro-pyrazol-3-one This compound was obtained in analogy to example 36, using 2-chlorophenol (step B) to give 5-(2-chloro-phenoxymethyl)-4-isopropyl-1-methyl-2-phenyl-1,2-dihydro-pyrazol-3-one as a light brown solid. MS (ESI$^+$): 357.0 [M+H]$^+$).

Example 40

Isopropoxymethyl-4-isopropyl-1-methyl-2-phenyl-1,2-dihydro-pyrazol-3-one

This compound was obtained in analogy to example 36, using propan-2-ol (step B) to give 5-isopropoxymethyl-4-isopropyl-1-methyl-2-phenyl-1,2-dihydro-pyrazol-3-one as a light brown solid. MS (ESI$^+$): 289.2 [M+H]$^+$).

Example 41

Ethyl-2-phenyl-1,2,4,5,6,7-hexahydro-indazol-3-one

Step A] 2-Phenyl-1,2,4,5,6,7-hexahydro-indazol-3-one

To a solution of cyclohexanone-2-carboxylic acid ethyl-ester (0.6 g) in acetic acid (1 mL) in a round bottom flask under argon was added phenylhydrazine (0.38 g). The mixture was immersed into an oil bath and heated to 120° C. overnight. The reaction vessel was then cooled and the acetic acid was evaporated in vacuo and the remaining solid was dissolved in EtOAc and water. The phases were separated and the aqueous phase was extracted with further EtOAc. The combined organic phases were washed with brine, dried over sodium sulfate, filtered and evaporated in vacuo and azeotroped with toluene (2×). The crude residue was then purified via ISCO Combiflash chromatography (eluting with EtOAc/heptane) to afford the desired 2-phenyl-1,2,4,5,6,7-hexahydro-indazol-3-one (0.56 g) as a light brown solid. MS (ESI$^+$): 215.4 ([M+H]$^+$).

Step B] 1-Ethyl-2-phenyl-1,2,4,5,6,7-hexahydro-indazol-3-one

To a solution of 2-phenyl-1,2,4,5,6,7-hexahydro-indazol-3-one (0.1 g) in DMF (1 mL) was added iodoethane (0.073 mL) and the mixture was placed into a pressure bomb and sealed. The reaction vessel was then heated in an oil bath to 100° C. over three days. The reaction vessel was then cooled and the DMF was evaporated in vacuo. The residue was dissolved in EtOAc and saturated and washed with saturated sodium bicarbonate solution. The phases were separated and the aqueous solution was extracted with EtOAc another two times at neutral pH. The combined organic phases were washed with brine, dried over sodium sulfate, filtered and evaporated in vacuo to afford a crude residue. Flash column chromatography over silica gel using ISCO combiflash chromatography and eluting with EtOAc/heptane and 3% AcOH afforded the desired 1-ethyl-2-phenyl-1,2,4,5,6,7-hexahydro-indazol-3-one (0.084 g) as a light brown solid. MS (ESI$^+$): MS (ESI$^+$): 243.4 [M+H]$^+$).

Example 42

Methyl-2-phenyl-1,4,5,6,7,8-hexahydro-2H-cyclo-heptapyrazol-3-one

This material was obtained in analogy to example 41 using 2-oxo-cycloheptanecarboxylic acid methyl ester (step A) and iodomethane (step B) via the following intermediate:
Step A] 2-Phenyl-1,4,5,6,7,8-hexahydro-2H-cycloheptapyrazol-3-one
After step B the title compound 1-methyl-2-phenyl-1,4,5,6,7,8-hexahydro-2H-cycloheptapyrazol-3-one was obtained as a light brown solid. MS (ESI$^+$): 243.4 [M+H]$^+$).

Example 43

Methyl-2-(1,7,7-trimethyl-bicyclo[2.2.1]hept-2-yl)-1,2,4,5,6,7-hexahydro-indazol-3-one This material was obtained in analogy to example 41 using 2-oxo-cyclohexanecarboxylic acid methyl ester (step A) and iodomethane (step B) via the following intermediate:
Step A] 2-(1,7,7-Trimethyl-bicyclo[2.2.1]hept-2-yl)-1,2,4,5,6,7-hexahydro-indazol-3-one
After step B the title compound 1-methyl-2-(1,7,7-trimethyl-bicyclo[2.2.1]hept-2-yl)-1,2,4,5,6,7-hexahydro-indazol-3-one was obtained as a beige solid. MS (ESI$^+$): 289.4 [M+H]$^+$).

Example 44

2-(2,4-Dichloro-phenyl)-1-methyl-1,2,4,5,6,7-hexahydro-indazol-3-one

This material was obtained in analogy to example 41 using 2-oxo-cyclohexanecarboxylic acid methyl ester and 2,4-dichlorophenylhydrazine (step A) and iodomethane (step B) via the following intermediate:
Step A] 2-(2,4-Dichloro-phenyl)-1,2,4,5,6,7-hexahydro-indazol-3-one
After step B the title compound 2-(2,4-dichloro-phenyl)-1-methyl-1,2,4,5,6,7-hexahydro-indazol-3-one was obtained as a light brown solid. MS (ESI$^+$): 297.4 [M+H]$^+$).

Example 45

Methyl-2-(2-trifluoromethyl-phenyl)-1,4,5,6,7,8-hexahydro-2H-cycloheptapyrazol-3-one This material was obtained in analogy to example 41 using 2-oxo-cycloheptanecarboxylic acid methyl ester and 2-trifluoromethylphenylhydrazine (step A) and iodomethane (step B) via the following intermediate:
Step A] 2-(2-Trifluoromethyl-phenyl)-1,4,5,6,7,8-hexahydro-2H-cycloheptapyrazol-3-one
After step B the title compound 1-methyl-2-(2-trifluoromethyl-phenyl)-1,4,5,6,7,8-hexahydro-2H-cycloheptapyrazol-3-one was obtained as an off-white solid. MS (ESI$^+$): 311.3 [M+H]$^+$).

Example 46

4-tert-Butyl-1,5-dimethyl-2-phenyl-1,2-dihydro-pyrazol-3-one

To a solution tert-butanol (800 μL) and 1,5-dimethyl-2-phenyl-1,2-dihydro-pyrazol-3-one (0.150 g) in dichloroethane (1 mL) was added boron trifluoride diethyletherate (400 µL). The reaction was heated to 40° C. over seven days. The reaction mixture was then cooled and poured onto an ice/water mixture, was basified to pH 10 using sodium hydroxide solution and was extracted with EtOAc. The solution was acidified with AcOH to pH=4 and further extracted with EtOAc. The combined organic phases were washed with brine and dried over sodium sulfate. Filtration and evaporation of the volatiles in vacuo afforded a crude residue which was purified via flash column chromatography to afford 4-tert-butyl-1,5-dimethyl-2-phenyl-1,2-dihydro-pyrazol-3-one (0.025 mg) as a white solid. MS (ESI$^+$): 245.4 [M+H]$^+$).

Example 47

4-tert-Butyl-2,5-dimethyl-1-phenyl-1,2-dihydro-pyrazol-3-one

Step A] 2,5-Dimethyl-1-phenyl-1,2-dihydro-pyrazol-3-one

This compound was obtained in analogy to example 61 using 5-methyl-1-phenyl-1,2-dihydro-pyrazol-3-one (*Synthesis* 1979, 4, 283-287) to give 2,5-dimethyl-1-phenyl-1,2-dihydro-pyrazol-3-one as a white solid. MS (ESI+): 189.4 [M+H]$^+$).
Step B] 4-tert-Butyl-2,5-dimethyl-1-phenyl-1,2-dihydro-pyrazol-3-one This compound was obtained in analogy to example 46 using 2,5-dimethyl-1-phenyl-1,2-dihydro-pyrazol-3-one to give 4-tert-butyl-2,5-dimethyl-1-phenyl-1,2-dihydro-pyrazol-3-one as a light brown solid. MS (ESI$^+$): 245.4 [M+H]$^+$).

Example 48

4-Adamantan-1-yl-5-methyl-1,2-dihydro-pyrazol-3-one

A suspension of 5-methyl-1,2-dihydro-pyrazol-3-one (4.0 g) and adamantan-1-ol (5.6 g) in a round bottom flask was cooled to 0° C. with an ice/water bath. To the cooled suspension was added borontrifluoride ethyl etherate (9.2 mL) over 10 minutes. The reaction mixture was then allowed to warm up to ambient temperature and stirred for 24 hours. The suspension was then re-cooled to 0° C. and quenched with 50% KOH solution. The mixture was then acidified with 2 N aqueous HCl solution and diluted with EtOAc. The resultant white precipitate was then collected by filtration and the solid was washed with ether. The white solid was dried in a dessicator to give the desired 4-adamantan-1-yl-5-methyl-1,2-dihydro-pyrazol-3-one (9.2 g) as a white solid. MS (ESI$^+$): 233.3 [M+H]$^+$).

Example 49

Adamantan-1-yl-3-methyl-6,7-dihydro-5H-pyrazolo[1,2-a]pyrazol-1-one

Into a sealable pressure vessel was placed 4-adamantan-1-yl-5-methyl-1,2-dihydro-pyrazol-3-one (3.5 g) (as described in example 48) along with 1,3-dibromopropane (6.1 g) and DMF (40 mL) and one equivalent of solid potassium carbonate. The reaction vessel was sealed and the solution was heated to 100° C. for 20 hours. The reaction was then allowed to cool and diluted with EtOAc and saturated sodium bicarbonate solution. The phases were separated and the aqueous phase was extracted with further EtOAc. The combined organic phases were washed with brine, dried over sodium sulfate, filtered and evaporated in vacuo. The obtained residue was purified via ISCO Combiflash chromatography (over silica column, eluting with EtOAc/heptane) to afford 2-adamantan-1-yl-3-methyl-6,7-dihydro-5H-pyrazolo[1,2-a]pyrazol-1-one (0.821 g) as a white solid. MS (ESI$^+$): 273.0 [M+H]$^+$).

Example 50

Adamantan-1-yl-3-methyl-5,6,7,8-tetrahydro-pyrazolo[1,2-a]pyridazin-1-one

This compound was obtained in analogy to example 49 using 1,4-dibromo-butane to give 2-adamantan-1-yl-3-methyl-5,6,7,8-tetrahydro-pyrazolo[1,2-a]pyridazin-1-one as an off-white solid. MS (ESI$^+$): 287.3 [M+H]$^+$).

Example 51

Adamantan-1-yl-3-methyl-6,7,8,9-tetrahydro-5H-pyrazolo[1,2-a][1,2]diazepin-1-one This compound was obtained in analogy to example 49 using 1,4-dibromo-pentane to give 2-adamantan-1-yl-3-methyl-6,7,8,9-tetrahydro-5H-pyrazolo[1,2-a][1,2]diazepin-1-one as an off-white solid. MS (ESI$^+$): 301.3 [M+H]$^+$).

Example 52

Adamantan-1-yl-3-cyclopropyl-6,7-dihydro-5H-pyrazolo[1,2-a]pyrazol-1-one

Step A] 5-Cyclopropyl-2,4-dihydro-pyrazol-3-one

To a solution of methyl-3-cyclopropyl-3-oxopropionate (10 g) and acetic acid (28 mL) in a round bottom flask under argon was added hydrazine hydrate (2.25 g). The mixture was immersed into an oil bath and heated to 100° C. overnight. The reaction vessel was then cooled and the acetic acid was evaporated in vacuo and the remaining solid was added to 1 N aqueous sodium hydroxide solution. The resulting precipitate was collected by filtration and washed with water and cold ether to afford the desired 5-cyclopropyl-2,4-dihydro-pyrazol-3-one (8.2 g) as a beige solid.
Step B] 4-Adamantan-1-yl-5-cyclopropyl-1,2-dihydro-pyrazol-3-one This compound was obtained in analogy to example 48 using 5-cyclopropyl-2,4-dihydro-pyrazol-3-one to give 4-adamantan-1-yl-5-cyclopropyl-1,2-dihydro-pyrazol-3-one as a white solid. MS (ESI$^-$): 259.1 [M–H]$^-$).

Part C] 2-Adamantan-1-yl-3-cyclopropyl-6,7-dihydro-5H-pyrazolo[1,2-a]pyrazol-1-one This compound was obtained in analogy to example 49 using 4-adamantan-1-yl-5-cyclopropyl-1,2-dihydro-pyrazol-3-one to give 2-adamantan-1-yl-3-cyclopropyl-6,7-dihydro-5H-pyrazolo[1,2-a]pyrazol-1-one as an off-white solid. MS (ESI+$^+$): 299.3 [M+H]$^+$).

Example 53

Adamantan-1-yl-1,2,5-trimethyl-1,2-dihydro-pyrazol-3-one

This compound was obtained in analogy to example 48 using 1,2,5-trimethyl-1,2-dihydro-pyrazol-3-one (prepared as described by v. Auwers and Niemeyer in *J. Prakt. Chem.*

1925, 110, 179) to give 4-adamantan-1-yl-1,2,5-trimethyl-1, 2-dihydro-pyrazol-3-one as an off white solid. MS (ESI+): 261.4 [M+H]$^+$).

Example 54

Adamantan-1-yl-1-benzyl-2,5-dimethyl-1,2-dihydro-pyrazol-3-one

Step A] 1-Benzyl-2,5-dimethyl-1,2-dihydro-pyrazol-3-one

This material was obtained in analogy to example 55 using 2,5-dimethyl-2,4-dihydro-pyrazol-3-one and benzylbromide to give 1-benzyl-2,5-dimethyl-1,2-dihydro-pyrazol-3-one as an off-white solid.

Step B] 4-Adamantan-1-yl-1-benzyl-2,5-dimethyl-1,2-dihydro-pyrazol-3-one

This material was obtained in analogy to example 48 using 1-benzyl-2,5-dimethyl-1,2-dihydro-pyrazol-3-one to give the desired 4-adamantan-1-yl-1-benzyl-2,5-dimethyl-1,2-dihydro-pyrazol-3-one as an off-white solid. MS (ESI+): 337.4 [M+H]$^+$).

Example 55

Adamantan-1-yl-1-isopropyl-5-methyl-1,2-dihydro-pyrazol-3-one

A sealable tube was charged with 4-adamantan-1-yl-5-methyl-1,2-dihydro-pyrazol-3-one (0.05 g), 2-bromopropane (0.026 g) and DMF and purged with argon and sealed. The reaction vessel was immersed into a heated oil bath at 110 degrees C. for 48 hours. The reaction vessel was then cooled and opened carefully. The reaction mixture was diluted with EtOAc and aq. NaHCO3 solution and the phases were separated. The aqueous layer was extracted with further EtOAc and the combined organic layers were washed with sodium thiosulfate. The phases were then dried over sodium sulfate, filtered and reduced in vacuo. The crude gum was chromatographed by adsorption onto silica gel and subjection to Isco Combiflash chromatography. Evaporation of the desired fractions afforded the desired product 4-adamantan-1-yl-1-isopropyl-5-methyl-1,2-dihydro-pyrazol-3-one (0.01 g) as an off white material. MS (ESI+): 275.3 [M+H]$^+$).

Example 56

Adamantan-1-yl-5-methyl-2-phenyl-1,2-dihydro-pyrazol-3-one

This compound was obtained in analogy to example 48 using 5-methyl-2-phenyl-2,4-dihydro-pyrazol-3-one to give 4-adamantan-1-yl-5-methyl-2-phenyl-1,2-dihydro-pyrazol-3-one as a light yellow solid. MS (ESI+): 309.3 [M+H]$^+$).

Example 57

4-Adamantan-1-yl-1,5-dimethyl-2-phenyl-1,2-dihydro-pyrazol-3-one

This compound was obtained in analogy to example 48 using 1,5-dimethyl-2-phenyl-1,2-dihydro-pyrazol-3-one to give 4-adamantan-1-yl-1,5-dimethyl-2-phenyl-1,2-dihydro-pyrazol-3-one as a white solid. MS (ESI+): 323.1 [M+H]$^+$).

Example 58

4-Adamantan-1-yl-2,5-dimethyl-1-phenyl-1,2-dihydro-pyrazol-3-one

This compound was obtained in analogy to example 61 using 4-adamantan-1-yl-5-methyl-1-phenyl-1,2-dihydro-pyrazol-3-one (see example 59) to give 4-adamantan-1-yl-2,5-dimethyl-1-phenyl-1,2-dihydro-pyrazol-3-one as an off-white solid. MS (ESI+): 323.3 [M+H]$^+$).

Example 59

4-Adamantan-1-yl-5-methyl-1-phenyl-1,2-dihydro-pyrazol-3-one

This compound was obtained in analogy to example 48 using 5-methyl-1-phenyl-1,2-dihydro-pyrazol-3-one (*Synthesis* 1979, 4, 283-287) as a white solid. MS (ESI+): 309.4 [M+H]$^+$).

Example 60

4-Adamantan-1-yl-1-phenyl-1,2-dihydro-pyrazol-3-one

This compound was obtained in analogy to example 48 using 1-phenyl-1,2-dihydro-pyrazol-3-one to give 4-adamantan-1-yl-1-phenyl-1,2-dihydro-pyrazol-3-one as a white solid. MS (ESI+): 295.3 [M+H]$^+$).

Example 61

4-Adamantan-1-yl-2-methyl-1-phenyl-1,2-dihydro-pyrazol-3-one

A sealable tube was charged with 4-adamantan-1-yl-1-phenyl-1,2-dihydro-pyrazol-3-one (0.05 g), iodomethane (0.036 g) and DMF (1 mL) and purged with argon and sealed. The reaction vessel was immersed into a heated oil bath at 110 degrees C. for 16 hours. The reaction vessel was then cooled and opened carefully. The reaction mixture was diluted with EtOAc and aqueous sodium bicarbonate solution and the phases were separated. The aqueous layer was extracted with further EtOAc and the combined organic layers were washed with sodium thiosulfate. The phases were then dried over sodium sulfate, filtered and reduced in vacuo. The crude gum was chromatographed by adsorption onto silica gel and subjection to Isco Combiflash chromatography. Evaporation of the desired fractions afforded the desired product 4-adamantan-1-yl-2-methyl-1-phenyl-1,2-dihydro-pyrazol-3-one (0.035 mg) as a white solid. MS (ESI$^+$): 309.4 [M+H]$^+$).

Example 62

4-Adamantan-1-yl-5-methyl-1-pyridin-2-yl-1,2-dihydro-pyrazol-3-one

Step A] 5-Methyl-1-pyridin-2-yl-1,2-dihydro-pyrazol-3-one

To a solution of pyridin-2-yl-hydrazine (1 g) in tert-butanol (15 mL) at 30° C. was added but-2-ynoic acid methyl ester (1 g). The reaction vessel was then cooled in an ice bath was treated with potassium tert butoxide (2 g) portionwise. The resulting suspension was stirred at ambient temperature for 16 hours. The tert-butanol was reduced in vacuo and the residue was taken up in water. The aqueous layer was extracted once with DCM. The aqueous layer was then acidified with AcOH to pH=3 and the resulting precipitate was collected by filtration and washed with water. The solid was collected and dried over P₂O₅ in a dessicator to give 5-methyl-1-pyridin-2-yl-1,2-dihydro-pyrazol-3-one (0.3 g) as a white solid. MS (ESI+): 176.3 [M+H]⁺).

Step B] 4-Adamantan-1-yl-5-methyl-1-pyridin-2-yl-1,2-dihydro-pyrazol-3-one

This compound was obtained in analogy to example 48 using 5-methyl-1-pyridin-2-yl-1,2-dihydro-pyrazol-3-one to give 4-adamantan-1-yl-5-methyl-1-pyridin-2-yl-1,2-dihydro-pyrazol-3-one as a white solid. MS (ESI+): 310.3 [M+H]⁺).

Example 63

4-Adamantan-1-yl-2,5-dimethyl-1-pyridin-2-yl-1,2-dihydro-pyrazol-3-one

This compound was obtained in analogy to example 61 using 4-adamantan-1-yl-5-methyl-1-pyridin-2-yl-1,2-dihydro-pyrazol-3-one to give 4-adamantan-1-yl-2,5-dimethyl-1-pyridin-2-yl-1,2-dihydro-pyrazol-3-one as an off-white solid. MS (ESI+): 324.5 [M+H]⁺).

Example 64

4-Adamantan-1-yl-1-(4-fluoro-phenyl)-2,5-dimethyl-1,2-dihydro-pyrazol-3-one

This compound was obtained in two steps in analogy to example 62 and 61 using 4-fluorophenylhydrazine (example 62) and using iodomethane and 4-adamantan-1-yl-1-(4-fluoro-phenyl)-5-methyl-1,2-dihydro-pyrazol-3-one (example 61) to give 4-adamantan-1-yl-1-(4-fluoro-phenyl)-2,5-dimethyl-1,2-dihydro-pyrazol-3-one as a yellow solid. MS (ESI+): 341.3 [M+H]⁺).

Example 65

4-Adamantan-1-yl-2-ethyl-5-methyl-1-phenyl-1,2-dihydro-pyrazol-3-one

This compound was obtained in two steps in analogy to example 61 using 4-adamantan-1-yl-5-methyl-1-phenyl-1,2-dihydro-pyrazol-3-one (example 59) and iodoethane to give 4-adamantan-1-yl-2-ethyl-5-methyl-1-phenyl-1,2-dihydro-pyrazol-3-one as a light brown solid. MS (ESI+): 337.5 [M+H]⁺).

Example 66

Adamantan-1-yl-5,6,7,8-tetrahydro-4H-pyrazolo[1,5-a]azepin-2-one

Step A] 8-Bromo-3-oxo-octanoic acid methyl ester

A round bottom flask equipped with a magnetic stir bar was flushed with argon and charged with THF (35 mL) and LDA solution (17.2 mL of a 2M solution in THF) at −78° C. To this was added 3-oxo-butyric acid methyl ester (2 g) dissolved in THF (5 mL) dropwise. The solution is then warmed to 0° C. and 1,4-dibromobutane (3.72) was added via syringe dissolved in THF (5 mL). The reaction was stirred for 1 hour and then quenched with 10 mL of 2N aqueous HCl solution and extracted with ether, and the combined organic phases were washed with water, aqueous sodium bicarbonate solution and brine. Drying over sodium sulfate, filtration and evaporation of the volatiles in vacuo afforded a crude oil. Flash column chromatography via ISCO Combiflash chromatography (EtOAc/heptane) afforded the desired 8-bromo-3-oxo-octanoic acid methyl ester (1.5 g) as a yellow oil. MS (ESI+): 251.1 [M+H]⁺).

Step B] 5,6,7,8-Tetrahydro-4H-pyrazolo[1,5-a]azepin-2-one

To a solution of 8-bromo-3-oxo-octanoic acid methyl ester (0.05 g) in ethanol (2 mL) in a round bottom flask under argon was added hydrazine hydrate (0.01 mL). The mixture was immersed into an oil bath and heated to 110° C. overnight. The reaction vessel was then cooled and the ethanol was evaporated in vacuo and the remaining solid was dissolved in EtOAc and aqueous sodium sulfate solution. The phases were separated and the aqueous phase was extracted with further EtOAc. The combined organic phases were washed with brine, dried over sodium sulfate, filtered and evaporated in vacuo. The crude residue was then purified via trituration with a 1:1 mixture of ether/pentane to afford the desired 5,6,7,8-tetrahydro-4H-pyrazolo[1,5-a]azepin-2-one (0.02 g) as a white solid. MS (ESI−): 153.1 ([M−H]−).

Step C] 3-Adamantan-1-yl-5,6,7,8-tetrahydro-4H-pyrazolo[1,5-a]azepin-2-one

This compound was obtained in analogy to example 48 using 5,6,7,8-tetrahydro-4H-pyrazolo[1,5-a]azepin-2-one to give 3-adamantan-1-yl-5,6,7,8-tetrahydro-4H-pyrazolo[1,5-a]azepin-2-one as a light yellow solid. MS (ESI+): 287.3 [M+H]⁺).

Example 67

Adamantan-1-yl-1-methyl-5,6,7,8-tetrahydro-4H-pyrazolo[1,5-a]azepin-2-one

This compound was obtained in analogy to example 61 using 3-adamantan-1-yl-5,6,7,8-tetrahydro-4H-pyrazolo[1,5-a]azepin-2-one to give 3-adamantan-1-yl-1-methyl-5,6,7,8-tetrahydro-4H-pyrazolo[1,5-a]azepin-2-one as a light yellow solid. MS (ESI+): 301.5 [M+H]⁺).

Example 68

Adamantan-1-yl-1-methyl-4,5,6,7-tetrahydro-pyrazolo[1,5-a]pyridin-2-one

Step A] 7-Bromo-3-oxo-heptanoic acid methyl ester

This compound is described in example 27, step A.

Step B] 4,5,6,7-Tetrahydro-pyrazolo[1,5-a]pyridin-2-one

This compound was obtained in analogy to example 66 step B using 7-bromo-3-oxo-heptanoic acid methyl ester to give 4,5,6,7-tetrahydro-pyrazolo[1,5-a]pyridin-2-one as a light brown solid.

Step C] 3-Adamantan-1-yl-5,6,7,8-tetrahydro-4H-pyrazolo[1,5-a]azepin-2-one

This compound was obtained in analogy to example 66 step C using 4,5,6,7-tetrahydro-pyrazolo[1,5-a]pyridin-2-one to give 3-adamantan-1-yl-5,6,7,8-tetrahydro-4H-pyrazolo[1,5-a]azepin-2-one as a light brown solid. MS (ESI+): 273.5 [M+H]⁺).

Step D] 3-Adamantan-1-yl-1-methyl-4,5,6,7-pyrazolo[1,5-a]pyridin-2-one

This compound was obtained in analogy to example 61 using 3-adamantan-1-yl-5,6,7,8-tetrahydro-4H-pyrazolo[1,5-a]azepin-2-one to give 3-adamantan-1-yl-1-methyl-4,5,6, 7-tetrahydro-pyrazolo[1,5-a]pyridin-2-one as a light brown solid. MS (ESI+): 287.3 [M+H]$^+$).

Example 69

Adamantan-1-yl-1-ethyl-4,5,6,7-tetrahydro-pyrazolo[1,5-a]pyridin-2-one

This compound was obtained in analogy to example 61 using 3-adamantan-1-yl-5,6,7,8-tetrahydro-4H-pyrazolo[1,5-a]azepin-2-one and iodoethane to give 3-adamantan-1-yl-1-ethyl-4,5,6,7-tetrahydro-pyrazolo[1,5-a]pyridin-2-one as a light brown solid. MS (ESI+): 301.5 [M+H]$^+$).

Example 70

1,5-Dimethyl-4-(4-methyl-bicyclo[2.2.2]oct-1-yl)-2-phenyl-1,2-dihydro-pyrazol-3-one This compound was obtained in analogy to example 71 step B using 1,5-dimethyl-2-phenyl-1,2-dihydro-pyrazol-3-one to give 1,5-dimethyl-4-(4-methyl-bicyclo[2.2.2]oct-1-yl)-2-phenyl-1,2-dihydro-pyrazol-3-one as a white solid. MS (ESI+): 311.3 [M+H]$^+$).

Example 71

2,5-Dimethyl-4-(4-methyl-bicyclo[2.2.2]oct-1-yl)-1-phenyl-1,2-dihydro-pyrazol-3-one Step A] 2,5-Dimethyl-1-phenyl-1,2-dihydro-pyrazol-3-one This compound was obtained in analogy to example 61 using 5-methyl-1-phenyl-1,2-dihydro-pyrazol-3-one (*Synthesis* 1979, 4, 283-287) as a white solid. MS (ESI+): 189.4 [M+H]$^+$).

Step B] 2,5-Dimethyl-4-(4-methyl-bicyclo[2.2.2]oct-1-yl)-1-phenyl-1,2-dihydro-pyrazol-3-one A suspension of 2,5-dimethyl-1-phenyl-1,2-dihydro-pyrazol-3-one (0.15 g) and adamantan-1-ol (0.1 g) in a round bottom flask was cooled to 0° C. with an ice/water bath. To the cooled suspension was added borontrifluoride ethyl etherate (0.18 mL) over 10 minutes. The reaction mixture was then allowed to warm up to ambient temperature and stirred for 20 days. The suspension was then re-cooled to 0° C. and quenched with 50% KOH solution. The mixture was then acidified to pH 6 and diluted with EtOAc. The phases were separated and the aqueous phase was extracted with further EtOAc. The combined organic phases were washed with brine and dried over sodium sulfate. Filtration and removal of the volatiles in vacuo afforded a crude residue that was purified via ISCO combiflash chromatography (EtOAc/heptane) to afford the desired 2,5-dimethyl-4-(4-methyl-bicyclo[2.2.2]oct-1-yl)-1-phenyl-1,2-dihydro-pyrazol-3-one (0.032 g) as a white solid. MS (ESI$^+$): 311.4 [M+H]$^+$).

Example 72

4,5-Dicyclopropyl-2-(2,3-dichloro-phenyl)-1-methyl-1,2-dihydro-pyrazol-3-one

This material was obtained in analogy to example 1 using (2,3-dichloro-phenyl)-hydrazine (step A) via the following intermediates:
Step A] 5-Cyclopropyl-2-(2,3-dichloro-phenyl)-2,4-dihydro-pyrazol-3-one
Step B] 5-Cyclopropyl-2-(2,3-dichloro-phenyl)-1-methyl-1,2-dihydro-pyrazol-3-one
Step C] 4-Bromo-5-cyclopropyl-2-(2,3-dichloro-phenyl)-1-methyl-1,2-dihydro-pyrazol-3-one After step D the title compound 4,5-dicyclopropyl-2-(2,3-dichloro-phenyl)-1-methyl-1,2-dihydro-pyrazol-3-one was obtained as an off-white solid. MS (ESI$^+$): 323.3 ([M+H]$^+$).

Example 73

Benzyl-4,5-dicyclopropyl-2-(2,4-difluoro-phenyl)-1,2-dihydro-pyrazol-3-one

This material was obtained in analogy to example 1 using (2,4-difluoro-phenyl)-hydrazine (step A) and benzyl bromide (step B) via the following intermediates:
Step A] 5-Cyclopropyl-2-(2,4-difluoro-phenyl)-2,4-dihydro-pyrazol-3-one
Step B] 1-Benzyl-5-cyclopropyl-2-(2,4-difluoro-phenyl)-1,2-dihydro-pyrazol-3-one
Step C] 1-Benzyl-4-bromo-5-cyclopropyl-2-(2,4-difluoro-phenyl)-1,2-dihydro-pyrazol-3-one After step D the title compound 1-Benzyl-4,5-dicyclopropyl-2-(2,4-difluoro-phenyl)-1,2-dihydro-pyrazol-3-one was obtained as an off-white solid. MS (ESI$^+$): 367.1 ([M+H]$^+$).

Example 74

4,5-Dicyclopropyl-2-(2,4-difluoro-phenyl)-1-(2-fluoro-benzyl)-1,2-dihydro-pyrazol-3-one This material was obtained in analogy to example 1 using (2,4-difluoro-phenyl)-hydrazine (step A) and 1-bromomethyl-2-fluoro-benzene (step B) via the following intermediates:
Step A] 5-Cyclopropyl-2-(2,4-difluoro-phenyl)-2,4-dihydro-pyrazol-3-one
Step B] 5-Cyclopropyl-2-(2,4-difluoro-phenyl)-1-(2-fluoro-benzyl)-1,2-dihydro-pyrazol-3-one
Step C] 4-Bromo-5-cyclopropyl-2-(2,4-difluoro-phenyl)-1-(2-fluoro-benzyl)-1,2-dihydro-pyrazol-3-one After step D the title compound 4,5-dicyclopropyl-2-(2,4-difluoro-phenyl)-1-(2-fluoro-benzyl)-1,2-dihydro-pyrazol-3-one was obtained as an off-white solid. MS (ESI$^+$): 385.1 ([M+H]$^+$).

Example 75

4,5-Dicyclopropyl-2-(2,4-difluoro-phenyl)-1-(4-fluoro-benzyl)-1,2-dihydro-pyrazol-3-one This material was obtained in analogy to example 1 using (2,4-difluoro-phenyl)-hydrazine (step A) and 1-bromomethyl-4-fluoro-benzene (step B) via the following intermediates:
Step A] 5-Cyclopropyl-2-(2,4-difluoro-phenyl)-2,4-dihydro-pyrazol-3-one
Step B] 5-Cyclopropyl-2-(2,4-difluoro-phenyl)-1-(4-fluoro-benzyl)-1,2-dihydro-pyrazol-3-one
Step C] 4-Bromo-5-cyclopropyl-2-(2,4-difluoro-phenyl)-1-(4-fluoro-benzyl)-1,2-dihydro-pyrazol-3-one After step D the title compound 4,5-dicyclopropyl-2-(2,4-difluoro-phenyl)-1-(4-fluoro-benzyl)-1,2-dihydro-pyrazol-3-one was obtained as an off-white solid. MS (ESI$^+$): 385.3 ([M+H]$^+$).

Example 76

4,5-Dicyclopropyl-2-(3-fluoro-2-trifluoromethyl-phenyl)-1-methyl-1,2-dihydro-pyrazol-3-one This material was obtained in analogy to example 1 using (3-fluoro-2-trifluoromethyl-phenyl)-hydrazine (step A) via the following intermediates:
Step A] 5-Cyclopropyl-2-(3-fluoro-2-trifluoromethyl-phenyl)-2,4-dihydro-pyrazol-3-one
Step B] 5-Cyclopropyl-2-(3-fluoro-2-trifluoromethyl-phenyl)-1-methyl-1,2-dihydro-pyrazol-3-one
Step C] 4-Bromo-5-cyclopropyl-2-(3-fluoro-2-trifluoromethyl-phenyl)-1-methyl-1,2-dihydro-pyrazol-3-one
After step D the title compound 4,5-dicyclopropyl-2-(3-fluoro-2-trifluoromethyl-phenyl)-1-methyl-1,2-dihydro-pyrazol-3-one was obtained as a white solid. MS (ESI$^+$): 341.1 ([M+H]$^+$).

Example 77

Benzyl-4,5-dicyclopropyl-2-(2,5-difluoro-phenyl)-1,2-dihydro-pyrazol-3-one

This material was obtained in analogy to example 1 using (2,5-difluoro-phenyl)-hydrazine (step A) and benzylbromide (step B) via the following intermediates:
Step A] 5-Cyclopropyl-2-(2,5-difluoro-phenyl)-2,4-dihydro-pyrazol-3-one
Step B] 1-Benzyl-5-cyclopropyl-2-(2,5-difluoro-phenyl)-1,2-dihydro-pyrazol-3-one
Step C] 1-Benzyl-4-bromo-5-cyclopropyl-2-(2,5-difluoro-phenyl)-1,2-dihydro-pyrazol-3-one
After step D the title compound 1-benzyl-4,5-dicyclopropyl-2-(2,5-difluoro-phenyl)-1,2-dihydro-pyrazol-3-one was obtained as an off-white solid. MS (ESI$^+$): 367.1 ([M+H]$^+$).

Example 78

4,5-Dicyclopropyl-2-(2,5-difluoro-phenyl)-1-methyl-1,2-dihydro-pyrazol-3-one This material was obtained in analogy to example 1 using (2,5-difluoro-phenyl)-hydrazine (step A) via the following intermediates:
Step A] 5-Cyclopropyl-2-(2,5-difluoro-phenyl)-2,4-dihydro-pyrazol-3-one
Step B] 5-Cyclopropyl-2-(2,5-difluoro-phenyl)-1-methyl-1,2-dihydro-pyrazol-3-one
Step C] 4-Bromo-5-cyclopropyl-2-(2,5-difluoro-phenyl)-1-methyl-1,2-dihydro-pyrazol-3-one
After step D the title compound 4,5-dicyclopropyl-2-(2,5-difluoro-phenyl)-1-methyl-1,2-dihydro-pyrazol-3-one was obtained as a white solid. MS (ESI$^+$): 291.1 ([M+H]$^+$).

Example 79

4,5-Dicyclopropyl-2-(2-methanesulfonyl-phenyl)-1-methyl-1,2-dihydro-pyrazol-3-one This material was obtained in analogy to example 1 using (2-methanesulfonyl-phenyl)-hydrazine (step A) via the following intermediates:
Step A] 5-Cyclopropyl-2-(2-methanesulfonyl-phenyl)-2,4-dihydro-pyrazol-3-one
Step B] 5-Cyclopropyl-2-(2-methanesulfonyl-phenyl)-1-methyl-1,2-dihydro-pyrazol-3-one
Step C] 4-Bromo-5-cyclopropyl-2-(2-methanesulfonyl-phenyl)-1-methyl-1,2-dihydro-pyrazol-3-one
After step D the title compound 4,5-dicyclopropyl-2-(2-methanesulfonyl-phenyl)-1-methyl-1,2-dihydro-pyrazol-3-one was obtained as a white solid. MS (ESI$^+$): 333.3 ([M+H]$^+$).

Example 80

4,5-Dicyclopropyl-1-methyl-2-(2-trifluoromethoxy-phenyl)-1,2-dihydro-pyrazol-3-one This material was obtained in analogy to example 1 using (2-trifluoromethoxy-phenyl)-hydrazine (step A) via the following intermediates:
Step A] 5-Cyclopropyl-2-(2-trifluoromethoxy-phenyl)-2,4-dihydro-pyrazol-3-one
Step B] 5-Cyclopropyl-1-methyl-2-(2-trifluoromethoxy-phenyl)-1,2-dihydro-pyrazol-3-one
Step C] 4-Bromo-5-cyclopropyl-1-methyl-2-(2-trifluoromethoxy-phenyl)-1,2-dihydro-pyrazol-3-one
After step D the title compound 4,5-dicyclopropyl-1-methyl-2-(2-trifluoromethoxy-phenyl)-1,2-dihydro-pyrazol-3-one was obtained as a white solid. MS (ESI$^+$): 339.1 ([M+H]$^+$).

Example 81

4,5-Dicyclopropyl-1-(2,4-difluoro-benzyl)-2-(2,5-difluoro-phenyl)-1,2-dihydro-pyrazol-3-one This material was obtained in analogy to example 1 using (2,5-difluoro-phenyl)-hydrazine (step A) and 1-bromomethyl-2,4-difluoro-benzene (step B) via the following intermediates:
Step A] 5-Cyclopropyl-2-(2,5-difluoro-phenyl)-2,4-dihydro-pyrazol-3-one
Step B] 5-Cyclopropyl-1-(2,4-difluoro-benzyl)-2-(2,5-difluoro-phenyl)-1,2-dihydro-pyrazol-3-one
Step C] 4-Bromo-5-cyclopropyl-1-(2,4-difluoro-benzyl)-2-(2,5-difluoro-phenyl)-1,2-dihydro-pyrazol-3-one
After step D the title compound 4,5-dicyclopropyl-1-(2,4-difluoro-benzyl)-2-(2,5-difluoro-phenyl)-1,2-dihydro-pyrazol-3-one was obtained as a white solid. MS (ESI$^+$): 403.4 ([M+H]$^+$).

Example 82

4,5-Dicyclopropyl-2-(2,4-difluoro-phenyl)-1-(3,3,3-trifluoro-propyl)-1,2-dihydro-pyrazol-3-one This material was obtained in analogy to example 1 using (2,4-difluoro-phenyl)-hydrazine (step A) and 3-bromo-1,1,1-trifluoro-propane (step B) via the following intermediates:
Step A] 5-Cyclopropyl-2-(2,4-difluoro-phenyl)-2,4-dihydro-pyrazol-3-one
Step B] 5-Cyclopropyl-2-(2,4-difluoro-phenyl) 1-(3,3,3-trifluoro-propyl)-1,2-dihydro-pyrazol-3-one
Step C] 4-Bromo-5-cyclopropyl-2-(2,4-difluoro-phenyl)-1-(3,3,3-trifluoro-propyl)-1,2-dihydro-pyrazol-3-one
After step D the title compound 4,5-dicyclopropyl-2-(2,4-difluoro-phenyl)-1-(3,3,3-trifluoro-propyl)-1,2-dihydro-pyrazol-3-one was obtained as a light brown solid. MS (ESI$^+$): 373.1 ([M+H]$^+$).

Example 83

4,5-Dicyclopropyl-2-(2,4-difluoro-phenyl)-1-pyridin-2-ylmethyl-1,2-dihydro-pyrazol-3-one This material was obtained in analogy to example 1 using (2,4-difluoro-phenyl)-hydrazine (step A) and 2-bromomethyl-pyridine (step B) via the following intermediates:
Step A] 5-Cyclopropyl-2-(2,4-difluoro-phenyl)-2,4-dihydro-pyrazol-3-one
Step B] 5-Cyclopropyl-2-(2,4-difluoro-phenyl)-1-pyridin-2-ylmethyl-1,2-dihydro-pyrazol-3-one
Step C] 4-Bromo-5-cyclopropyl-2-(2,4-difluoro-phenyl)-1-pyridin-2-ylmethyl-1,2-dihydro-pyrazol-3-one After step D the title compound 4,5-dicyclopropyl-2-(2,4-difluoro-phenyl)-1-pyridin-2-ylmethyl-1,2-dihydro-pyrazol-3-one was obtained as a light brown solid. MS (ESI$^+$): 368.1 ([M+H]$^+$).

Example 84

4,5-Dicyclopropyl-1-methyl-2-o-tolyl-1,2-dihydro-pyrazol-3-one

This material was obtained in analogy to example 1 using o-tolyl-hydrazine (step A) via the following intermediates:
Step A] 5-Cyclopropyl-2-o-tolyl-2,4-dihydro-pyrazol-3-one
Step B] 5-Cyclopropyl-1-methyl-2-o-tolyl-1,2-dihydro-pyrazol-3-one
Step C] 4-Bromo-5-cyclopropyl-1-methyl-2-o-tolyl-1,2-dihydro-pyrazol-3-one After step D the title compound 4,5-dicyclopropyl-1-methyl-2-o-tolyl-1,2-dihydro-pyrazol-3-one was obtained as an off-white solid. MS (ESI$^+$): 269.5 ([M+H]$^+$).

Example 85

Benzothiazol-2-yl-4,5-dicyclopropyl-1-methyl-1,2-dihydro-pyrazol-3-one

This material was obtained in analogy to example 1 using benzothiazol-2-yl-hydrazine (step A) via the following intermediates:
Step A] 2-Benzothiazol-2-yl-5-cyclopropyl-2,4-dihydro-pyrazol-3-one
Step B] 2-Benzothiazol-2-yl-5-cyclopropyl-1-methyl-1,2-dihydro-pyrazol-3-one
Step C] 2-Benzothiazol-2-yl-4-bromo-5-cyclopropyl-1-methyl-1,2-dihydro-pyrazol-3-one After step D the title compound 2-benzothiazol-2-yl-4,5-dicyclopropyl-1-methyl-1,2-dihydro-pyrazol-3-one was obtained as an off-white solid. MS (ESI$^+$): 312.4 ([M+H]$^+$).

Example 86

4,5-Dicyclopropyl-2-(2,3-dimethyl-phenyl)-1-methyl-1,2-dihydro-pyrazol-3-one

This material was obtained in analogy to example 1 using (2,3-dimethyl-phenyl)-hydrazine (step A) via the following intermediates:
Step A] 5-Cyclopropyl-2-(2,3-dimethyl-phenyl)-2,4-dihydro-pyrazol-3-one
Step B] 5-Cyclopropyl-2-(2,3-dimethyl-phenyl)-1-methyl-1,2-dihydro-pyrazol-3-one
Step C] 4-Bromo-5-cyclopropyl-2-(2,3-dimethyl-phenyl)-1-methyl-1,2-dihydro-pyrazol-3-one After step D the title compound 4,5-dicyclopropyl-2-(2,3-dimethyl-phenyl)-1-methyl-1,2-dihydro-pyrazol-3-one was obtained as a white solid. MS (ESI$^+$): 283.4 ([M+H]$^+$).

Example 87

4,5-Dicyclopropyl-2-(2-ethyl-phenyl)-1-methyl-1,2-dihydro-pyrazol-3-one

This material was obtained in analogy to example 1 using (2-ethyl-phenyl)-hydrazine (step A) via the following intermediates:
Step A] 5-Cyclopropyl-2-(2-ethyl-phenyl)-2,4-dihydro-pyrazol-3-one
Step B] 5-Cyclopropyl-2-(2-ethyl-phenyl)-1-methyl-1,2-dihydro-pyrazol-3-one
Step C] 4-Bromo-5-cyclopropyl-2-(2-ethyl-phenyl)-1-methyl-1,2-dihydro-pyrazol-3-one After step D the title compound 4,5-dicyclopropyl-2-(2-ethyl-phenyl)-1-methyl-1,2-dihydro-pyrazol-3-one was obtained as a white solid. MS (ESI$^+$): 283.5 ([M+H]$^+$).

Example 88

4,5-Dicyclopropyl-2-(2,5-dichloro-phenyl)-1-methyl-1,2-dihydro-pyrazol-3-one

This material was obtained in analogy to example 1 using (2,5-dichloro-phenyl)-hydrazine (step A) via the following intermediates:
Step A] 5-Cyclopropyl-2-(2,5-dichloro-phenyl)-2,4-dihydro-pyrazol-3-one
Step B] 5-Cyclopropyl-2-(2,5-dichloro-phenyl)-1-methyl-1,2-dihydro-pyrazol-3-one
Step C] 4-Bromo-5-cyclopropyl-2-(2,5-dichloro-phenyl)-1-methyl-1,2-dihydro-pyrazol-3-one After step D the title compound 4,5-dicyclopropyl-2-(2,5-dichloro-phenyl)-1-methyl-1,2-dihydro-pyrazol-3-one was obtained as an off-white solid. MS (ESI$^+$): 323.4 ([M+H]$^+$).

Example 89

4,5-Dicyclopropyl-2-(2-fluoro-3-methyl-6-trifluoromethyl-phenyl)-1-methyl-1,2-dihydro-pyrazol-3-one This material was obtained in analogy to example 1 using (2-fluoro-3-methyl-6-trifluoromethyl-phenyl)-hydrazine (step A) via the following intermediates:
Step A] 5-Cyclopropyl-2-(2-fluoro-3-methyl-6-trifluoromethyl-phenyl)-2,4-dihydro-pyrazol-3-one
Step B] 5-Cyclopropyl-2-(2-fluoro-3-methyl-6-trifluoromethyl-phenyl)-1-methyl-1,2-dihydro-pyrazol-3-one
Step C] 4-Bromo-5-cyclopropyl-2-(2-fluoro-3-methyl-6-trifluoromethyl-phenyl)-1-methyl-1,2-dihydro-pyrazol-3-one After step D the title compound 4,5-dicyclopropyl-2-(2-fluoro-3-methyl-6-trifluoromethyl-phenyl)-1-methyl-1,2-dihydro-pyrazol-3-one was obtained as a white solid. MS (ESI$^+$): 355.3 ([M+H]$^+$).

Example 90

Cyclopropyl-1-methyl-5-trifluoromethyl-2-(2-trifluoromethyl-phenyl)-1,2-dihydro-pyrazol-3-one This material was obtained in analogy to example 1 (except step B) using (2-trifluoromethyl-phenyl)-hydrazine and 4,4,4-trifluoro-3-oxo-butyric acid ethyl ester (step A) via the following intermediates:

Step A] 5-Trifluoromethyl-2-(2-trifluoromethyl-phenyl)-1,2-dihydro-pyrazol-3-one Step B] 1-Methyl-5-trifluoromethyl-2-(2-trifluoromethyl-phenyl)-1,2-dihydro-pyrazol-3-one To 19.5 ml (50.7 mmol) of dimethyl sulphate was added to 1.5 g (5.1 mmol) of 1-Methyl-5-trifluoromethyl-2-(2-trifluoromethyl-phenyl)-1,2-dihydro-pyrazol-3-one in a reaction vessel and stirred, the reaction was then refluxed at 120° C. for 15 minutes. The reaction mixture was then worked up using (2×40 ml) water and (2×50 ml) ethyl acetate, the organic solution was separated from the aqueous layer, dried (Na2SO4) and concentrated. The combined organic components were separated and purified by column chromatography (AcOEt 95:5 heptane) to yield 1-methyl-5-trifluoromethyl-2-(2-trifluoromethyl-phenyl)-1,2-dihydro-pyrazol-3-one (918 mg, 58% yield) as an off-white solid. MS (ESI$^+$): 311.0 ([M+H]$^+$).

Step C] 4-Bromo-1-methyl-5-trifluoromethyl-2-(2-trifluoromethyl-phenyl)-1,2-dihydro-pyrazol-3-one After step D the title compound 4-cyclopropyl-1-methyl-5-trifluoromethyl-2-(2-trifluoromethyl-phenyl)-1,2-dihydro-pyrazol-3-one was obtained as yellow gum. MS (ESI$^+$): 351.1 ([M+H]$^+$).

Example 91

Cyclopropyl-5-(2,2-difluoro-cyclopropyl)-1-methyl-2-(2-trifluoromethyl-phenyl)-1,2-dihydro-pyrazol-3-one Step A] 2,2-Difluoro-cyclopropanecarbonyl chloride To a solution of commercially available 2,2-difluoro cyclopropanic acid (1.0 g, 8.2 mmol) in DCM (27.3 ml) was added the 1 drop of DMF and the mixture was stirred under inert argon atmosphere and cooled to 0° C. in an ice bath. Oxalyl chloride (1 eq) was then injected and the bath was left to warm slowly to ambient temperature and the solution stirred for 18 hours. The solution was then evaporated under reduced in vacuo and the remaining residue was used in the next reaction without further purification.

Step B] 3-(2,2-Difluoro-cyclopropyl)-3-oxo-propionic acid ethyl ester

To monoethyl malonate (2.164 g, 16.4 mmol) in a round bottom flask under inert argon atmosphere was added 60 ml of THF and the vessel was cooled to −78° C. To this was added n-butyllithium solution (20.48 ml of 1.6 M in hexane, 32.8 mmol) and the temperature was raised gradually until it reached 0° C. for 15 minutes. The lithiated malonate solution was then cooled to −78° C. again and the crude 2,2-difluoro-cyclopropanecarbonyl chloride dissolved in THF (10 mL) was added drop wise over 20 minutes and the reaction mixture was warmed to 0° C. at which time the reaction was complete as shown by TLC (potasiumpermanganate stain). The reaction mixture was then worked up with (2×20 ml) saturated sodium hydrogen carbonate solution and (1×20 ml) saturated brine solution. This was then extracted with (2×20 ml) ethyl acetate and the organic portion of the reaction mixture was then reduced in-vacuo and subsequently adsorbed onto silica and chromatographed (AcOEt 10:90 heptane). Combination of the desired fractions and evaporation afforded 3-(2,2-difluoro-cyclopropyl)-3-oxo-propionic acid ethyl ester (678 mg, 43% yield) as a colourless liquid. MS (ESI$^+$): 193.3, 4 ([M+H]$^+$).

Step C] 5-(2,2-Difluoro-cyclopropyl)-2-(2-trifluoromethyl-phenyl)-2,4-dihydro-pyrazol-3-one This material was obtained in analogy to example 1 using 3-(2,2-difluoro-cyclopropyl)-3-oxo-propionic acid ethyl ester and (2-trifluoromethyl-phenyl)-hydrazine (step A). MS (ESI$^+$): 305.1 ([M+H]$^+$).

Step D] 5-(2,2-Difluoro-cyclopropyl)-1-methyl-2-(2-trifluoromethyl-phenyl)-1,2-dihydro-pyrazol-3-one This material was obtained in analogy to example 89 (step B) using 5-(2,2-difluoro-cyclopropyl)-2-(2-trifluoromethyl-phenyl)-2,4-dihydro-pyrazol-3-one and using 5 minutes reaction time. MS (ESI$^+$): 319.1 ([M+H]$^+$).

Step E] 4-Bromo-5-(2,2-difluoro-cyclopropyl)-1-methyl-2-(2-trifluoromethyl-phenyl)-1,2-dihydro-pyrazol-3-one This material was obtained in analogy to example 1 (step C) using 5-(2,2-difluoro-cyclopropyl)-1-methyl-2-(2-trifluoromethyl-phenyl)-1,2-dihydro-pyrazol-3-one.

Step F] 4-Cyclopropyl-5-(2,2-difluoro-cyclopropyl)-1-methyl-2-(2-trifluoromethyl-phenyl)-1,2-dihydro-pyrazol-3-one This material was obtained in analogy to example 1 (step D) using 4-bromo-5-(2,2-difluoro-cyclopropyl)-1-methyl-2-(2-trifluoromethyl-phenyl)-1,2-dihydro-pyrazol-3-one to afford the desired 4-cyclopropyl-5-(2,2-difluoro-cyclopropyl)-1-methyl-2-(2-trifluoromethyl-phenyl)-1,2-dihydro-pyrazol-3-one as an off-white solid. MS (ESI$^+$): 359.1 ([M+H]$^+$).

Example 92

Cyclopropyl-5-(3,3-difluoro-cyclobutyl)-1-methyl-2-(2-trifluoromethyl-phenyl)-1,2-dihydro-pyrazol-3-one Step A] 3-(3,3-Difluoro-cyclobutyl)-3-oxo-propionic acid ethyl ester Zinc metal (0.558 g, 10 micron dust, 8.5 mmol) was stirred in THF (2.5 ml) and methane sulphonic acid (0.04 mmol) was added and refluxed at 76° C. for 10 minutes. To this was added 3,3-difluoro-cyclobutanecarbonitrile (500 mg, 4.3 mmol, prepared according to Elend et al. *Synth Comm*, 2005, 35, 657) and the reaction mixture was heated for a further 10 minutes. Ethyl bromoacetate (0.751 ml, 6.8 mmol) dissolved in THF (0.5 mL) was then injected over a 2 hour period with the aid of a syringe pump and after the addition the mixture was stirred for a further 30 minutes. Aqueous HCl (3 ml of 3 M solution) was added drop-wise at 0° C. and the reaction mixture was then stirred for 17 hours between 0 and 20° C. The reaction mixture was analyzed by MS and TLC which showed the formation of the product and the consumption of the starting material and the reaction was worked up with (2×20 ml) water and (2×20 ml) ethyl acetate, the organic portion was then dried (Na2SO4) and reduced in vacuo. The product was isolated and purified using flash chromatography (AcOEt 7:93 heptane) and 3-(3,3-difluoro-cyclobutyl)-3-oxo-propionic acid ethyl ester (599 mg, 68% yield) was obtained as a colourless liquid. MS (ESI$^+$): 207.1 ([M+H]$^+$).

Step B] 5-(3,3-Difluoro-cyclobutyl)-2-(2-trifluoromethyl-phenyl)-2,4-dihydro-pyrazol-3-one This material was obtained in analogy to example 1, step A using 3-(3,3-difluoro-cyclobutyl)-3-oxo-propionic acid ethyl ester and (2-trifluoromethyl-phenyl)-hydrazine. MS (ESI$^+$): 319.0 ([M+H]$^+$).

Step C] 5-(3,3-Difluoro-cyclobutyl)-1-methyl-2-(2-trifluoromethyl-phenyl)-1,2-dihydro-pyrazol-3-one This material was obtained in analogy to example 1, step B using 5-(3,3-difluoro-cyclobutyl)-2-(2-trifluoromethyl-phenyl)-2,4-dihydro-pyrazol-3-one. MS (ESI$^+$): 333.1 ([M+H]$^+$).

Step D] 4-Bromo-5-(3,3-difluoro-cyclobutyl)-1-methyl-2-(2-trifluoromethyl-phenyl)-1,2-dihydro-pyrazol-3-one This material was obtained in analogy to example 1, step C using 5-(3,3-difluoro-cyclobutyl)-1-methyl-2-(2-trifluoromethyl-phenyl)-1,2-dihydro-pyrazol-3-one. MS (ESI$^+$): 410.9 ([M+H]$^+$).

Step E] 4-Cyclopropyl-5-(3,3-difluoro-cyclobutyl)-1-methyl-2-(2-trifluoromethyl-phenyl)-1,2-dihydro-pyrazol-3-one This material was obtained in analogy to example 1, step D using 4-bromo-5-(3,3-difluoro-cyclobutyl)-1-methyl-2-(2-trifluoromethyl-phenyl)-1,2-dihydro-pyrazol-3-one to give the desired 4-cyclopropyl-5-(3,3-difluoro-cyclobutyl)-1-methyl-2-(2-trifluoromethyl-phenyl)-1,2-dihydro-pyrazol-3-one as a yellow gum MS (ESI$^+$): 373.1 ([M+H]$^+$).

Example 93

4,5-Dicyclopropyl-2-(2,4-difluoro-phenyl)-1-(2,2,2-trifluoro-ethyl)-1,2-dihydro-pyrazol-3-one This material was obtained in analogy to example 1 using (2,4-difluoro-phenyl)-hydrazine (step A) and trifluoro-methanesulfonic acid 2,2,2-trifluoro-ethyl ester (step B) via the following intermediates:
Step A] 5-Cyclopropyl-2-(2,4-difluoro-phenyl)-2,4-dihydro-pyrazol-3-one
Step B] 5-Cyclopropyl-2-(2,4-difluoro-phenyl)-1-(2,2,2-trifluoro-ethyl)-1,2-dihydro-pyrazol-3-one
Step C] 4-Bromo-5-cyclopropyl-2-(2,4-difluoro-phenyl)-1-(2,2,2-trifluoro-ethyl)-1,2-dihydro-pyrazol-3-one After step D the title compound 4,5-dicyclopropyl-2-(2,4-difluoro-phenyl)-1-(2,2,2-trifluoro-ethyl)-1,2-dihydro-pyrazol-3-one was obtained as a yellow oil. MS (ESI$^+$): 359.0 ([M+H]$^+$).

Example 94

4,5-Dicyclopropyl-2-(2,2-dimethyl-propyl)-1-methyl-1,2-dihydro-pyrazol-3-one

This material was obtained in analogy to example 1 using (2,2-dimethyl-propyl)-hydrazine (step A) via the following intermediates:
Step A] 5-Cyclopropyl-2-(2,2-dimethyl-propyl)-2,4-dihydro-pyrazol-3-one
Step B] 5-Cyclopropyl-2-(2,2-dimethyl-propyl)-1-methyl-1,2-dihydro-pyrazol-3-one
Step C] 4-Bromo-5-cyclopropyl-2-(2,2-dimethyl-propyl)-1-methyl-1,2-dihydro-pyrazol-3-one After step D the title compound 4,5-dicyclopropyl-2-(2,2-dimethyl-propyl)-1-methyl-1,2-dihydro-pyrazol-3-one was obtained as an off-white solid. MS (ESI$^+$): 249.3 ([M+H]$^+$).

Example 95

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example 96

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

It is to be understood that the invention is not limited to the particular embodiments of the invention described above, as variations of the particular embodiments may be made and still fall within the scope of the appended claims.

What is claimed is:
1. A compound of the formula (I):

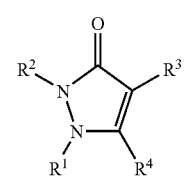

wherein
R$^1$ is hydrogen, alkyl, cycloalkyl, cycloalkylalkyl, aralkyl, haloalkyl, aryl, pyridinylmethyl or heterocyclyl; and with the proviso that in case R$^1$ is hydrogen then R$^3$ is adamantanyl or adamantanyl substituted with one to three substituents independently selected from alkyl, hydroxy, halogen and haloalkyl;
R$^2$ is hydrogen, alkyl, cycloalkyl, aryl, aralkyl, benzothiazolyl, bicyclo(2.2.1)heptyl or bicyclo(2.2.2)octyl, wherein bicyclo(2.2.1)heptyl and bicyclo(2.2.2)octyl are optionally substituted with one to three substituents independently selected from alkyl, hydroxy, halogen and haloalkyl;
or R$^1$ and R$^2$ together with the nitrogen atoms to which they are attached form pyrazolidine, hexahydro-pyridazine, (1,2) diazepane or 2,3,4,5, tetrahydro-1H- benzo(c)(1,2)diazepine, wherein pyrazolidine, hexahydro-pyridazine, (1,2)diazepane and 2,3,4,5, tetrahydro-1H-benzo(c)(1,2)diazepine are optionally substituted with one to three alkyl groups;

or $R^1$ and $R^4$ together form —$(CH_2)_m$—;

m is 3, 4, 5 or 6;

$R^3$ is cyclopropyl, arylcyclopropyl, isopropyl, tert.-butyl, adamantanyl or bicyclo(2.2.2)octyl, wherein adamantanyl and bicyclo(2.2.2)octyl are optionally substituted with one to three substituents independently selected from alkyl, hydroxy, halogen and haloalkyl;

$R^4$ is hydrogen, alkyl, cycloalkyl, aryloxyalkyl, alkylcarbonylaminoaryloxyalkyl, alkyloxyalkyl, aryl, aralkyl, haloalkyl or halocycloalkyl;

or $R^3$ and $R^4$ together form —$(CH_2)_n$—;

n is 3, 4, 5 or 6;

and pharmaceutically acceptable salts and esters thereof; with the proviso that in case $R^3$ and $R^4$ together form —$(CH_2)_n$— then $R^1$ is alkyl and $R^2$ is not hydrogen or alkyl; and with the proviso that in case $R^4$ is hydrogen or alkyl then $R^3$ is not isopropyl; and with the proviso that 3-cyclopropyl-4-isopropyl-2-methyl-1-phenyl-3-pyrazolin-5-one; 1,2-dihydro-5-methyl-4-tricyclo(3.3.1.13,7)dec-1-yl-3H-pyrazol-3-one; 1,2,3,4,6,7,8,9-octahydro-10H,12H-indazolo(1,2-a)indazole-10,12-dione; 1,2,4,5,6,7-hexahydro-1-methyl-2-phenyl-3H-indazol-3-one; 1,4,5,6-tetrahydro-1-methyl-2-phenyl-3(2H)-cyclopentapyrazolone; 1,4,5,6-tetrahydro-1-benzyl-2-phenyl-3(2H)-cyclopentapyrazolone; 1,4,5,6-tetrahydro-1-ethyl-2-(4-methyl)-phenyl-3(2H)-cyclopentapyrazolone; 1,4,5,6-tetrahydro-1-ethyl-2-phenyl-3(2H)-cyclopentapyrazolone; and 1,4,5,6,7,8-hexahydro-1-methyl-2-phenyl-3(2H)-cycloheptapyrazolone are excluded.

2. The compound according to claim 1, wherein $R^1$ is hydrogen, alkyl, cycloalkyl, cycloalkylalkyl, aralkyl, haloalkyl, aryl or heterocyclyl; and with the proviso that in case $R^1$ is hydrogen then $R^3$ is adamantanyl or adamantanyl substituted with one to three substituents independently selected from alkyl, hydroxy, halogen and haloalkyl;

$R^2$ is hydrogen, alkyl, cycloalkyl, aryl, aralkyl, bicyclo(2.2.1)heptyl or bicyclo(2.2.2)octyl, wherein bicyclo(2.2.1)heptyl and bicyclo(2.2.2)octyl are optionally substituted with one to three substituents independently selected from alkyl, hydroxy, halogen and haloalkyl;

or $R^1$ and $R^2$ together with the nitrogen atoms to which they are attached form pyrazolidine, hexahydro-pyridazine, (1,2)diazepane or 2,3,4,5, tetrahydro-1H-benzo(c)(1,2)diazepine, wherein pyrazolidine, hexahydro-pyridazine, (1,2)diazepane and 2,3,4,5, tetrahydro-1H-benzo(c)(1,2)diazepine are optionally substituted with one to three alkyl groups;

or $R^1$ and $R^4$ together form —$(CH_2)_m$—;

m is 3, 4, 5 or 6;

$R^4$ is hydrogen, alkyl, cycloalkyl, aryloxyalkyl, alkylcarbonylaminoaryloxyalkyl, alkyloxyalkyl, aryl, aralkyl or haloalkyl;

or $R^3$ and $R^4$ together form —$(CH_2)_n$—; and n is 3, 4, 5 or 6.

3. The compound according to claim 1, wherein $R^3$ is cyclopropyl, isopropyl, tert-butyl, adamantanyl or 4-methyl-bicyclo(2.2.2)octyl.

4. The compound according to claim 1, wherein $R^3$ is cyclopropyl or adamantanyl.

5. The compound according to claim 1, wherein $R^4$ is cyclopropyl, cyclobutyl, 1-methyl-cyclopropyl, tert-butyl, 2,2-dimethyl-cyclopropyl, fluoro-phenoxymethyl, fluoro-phenyl-ethyl, chloro-phenoxymethyl, dichloro-phenoxymethyl, isopropoxymethyl, methyl, hydrogen or trifluoromethyl.

6. The compound according to claim 1, wherein $R^4$ is cyclopropyl, cyclobutyl, 1-methyl-cyclopropyl, tert-butyl, 2,2-dimethyl-cyclopropyl or 4-fluoro-phenoxymethyl.

7. The compound according to claim 1, wherein $R^3$ is adamantanyl and $R^4$ is hydrogen, methyl or cyclopropyl.

8. The compound according to claim 1, wherein $R^1$ is hydrogen, methyl, ethyl, isopropyl, cyclopropyl, benzyl, cyclopropylmethyl, phenyl, pyridinyl or fluorophenyl.

9. The compound according to claim 1, wherein $R^1$ is methyl or phenyl.

10. The compound according to claim 1, wherein $R^1$ and $R^2$ together with the nitrogen atoms to which they are attached form pyrazolidine, hexahydro-pyridazine or (1,2)diazepane.

11. The compound according to claim 1, wherein $R^1$ and $R^4$ together form —$(CH_2)_m$—, wherein m is 4 or 5.

12. The compound according to claim 1, wherein $R^3$ and $R^4$ together form —$(CH_2)_n$—, wherein n is 4 or 5.

13. The compound according to claim 1, wherein $R^2$ is hydrogen, methyl, ethyl, 1,7,7-trimethyl-bicyclo(2.2.1)hept-2-yl, naphthyl, phenyl or substituted phenyl, wherein the substituted phenyl is phenyl substituted with one to three substituents independently selected from fluoro, chloro, trifluoromethyl and hydroxy.

14. The compound according to claim 1, wherein $R^2$ is methyl, fluoro-phenyl, chloro-phenyl or trifluoromethyl-phenyl.

15. The compound according to claim 1 selected from
4,5-Dicyclopropyl-1-methyl-2-phenyl-1,2-dihydro-pyrazol-3-one;
4,5-Dicyclopropyl-2-(2-fluoro-phenyl)-1-methyl-1,2-dihydro-pyrazol-3-one;
4,5-Dicyclopropyl-2-(4-fluoro-phenyl)-1-methyl-1,2-dihydro-pyrazol-3-one;
4,5-Dicyclopropyl-2-(2,4-difluoro-phenyl)-1-methyl-1,2-dihydro-pyrazol-3-one;
4,5-Dicyclopropyl-2-(3-fluoro-phenyl)-1-methyl-1,2-dihydro-pyrazol-3-one;
2-(2-Chloro-phenyl)-4,5-dicyclopropyl-1-methyl-1,2-dihydro-pyrazol-3-one;
2-(3-Chloro-phenyl)-4,5-dicyclopropyl-1-methyl-1,2-dihydro-pyrazol-3-one;
4,5-Dicyclopropyl-1-methyl-2-(2-trifluoromethyl-phenyl)-1,2-dihydro-pyrazol-3-one;
4,5-Dicyclopropyl-1-methyl-2-(3-trifluoromethyl-phenyl)-1,2-dihydro-pyrazol-3-one;
4,5-Dicyclopropyl-2-(4-fluoro-2-trifluoromethyl-phenyl)-1-methyl-1,2-dihydro-pyrazol-3-one;
4,5-Dicyclopropyl-2-(2-methoxy-phenyl)-1-methyl-1,2-dihydro-pyrazol-3-one,
4,5-Dicyclopropyl-1-methyl-2-naphthalen-1-yl-1,2-dihydro-pyrazol-3-one;
4,5-Dicyclopropyl-1-ethyl-2-(4-fluoro-phenyl)-1,2-dihydro-pyrazol-3-one;
4,5-Dicyclopropyl-1-ethyl-2-(3-fluoro-phenyl)-1,2-dihydro-pyrazol-3-one;
2-(2-Chloro-phenyl)-4,5-dicyclopropyl-1-ethyl-1,2-dihydro-pyrazol-3-one;
2-(3-Chloro-phenyl)-4,5-dicyclopropyl-1-ethyl-1,2-dihydro-pyrazol-3-one;
4,5-Dicyclopropyl-1-ethyl-2-(2-trifluoromethyl-phenyl)-1,2-dihydro-pyrazol-3-one;
1-Benzyl-4,5-dicyclopropyl-2-(2-trifluoromethyl-phenyl)-1,2-dihydro-pyrazol-3-one;

4,5-Dicyclopropyl-1-cyclopropylmethyl-2-(2-trifluoromethyl-phenyl)-1,2-dihydro-pyrazol-3-one;
2-Benzyl-4,5-dicyclopropyl-1-methyl-1,2-dihydro-pyrazol-3-one;
2,3-Dicyclopropyl-6,7,8,9-tetrahydro-5H-pyrazolo[1,2-a][1,2]diazepin-1-one;
5-Cyclobutyl-4-cyclopropyl-1-methyl-2-phenyl-1,2-dihydro-pyrazol-3-one;
5-Cyclobutyl-4-cyclopropyl-1-methyl-2-(2-trifluoromethyl-phenyl)-1,2-dihydro-pyrazol-3-one;
4-Cyclopropyl-1-methyl-5-(1-methyl-cyclopropyl)-2-(2-trifluoromethyl-phenyl)-1,2-dihydro-pyrazol-3-one;
5-tert-Butyl-4-cyclopropyl-1-methyl-2-(2-trifluoromethyl-phenyl)-1,2-dihydro-pyrazol-3-one;
4-Cyclopropyl-5-(2,2-dimethyl-cyclopropyl)-1-methyl-2-(2-trifluoromethyl-phenyl)-1,2-dihydro-pyrazol-3-one;
3-Cyclopropyl-1-phenyl-4,5,6,7-tetrahydro-pyrazolo[1,5-a]pyridin-2-one;
4-Cyclopropyl-5-(4-fluoro-phenoxymethyl)-1-methyl-2-phenyl-1,2-dihydro-pyrazol-3-one;
4-Cyclopropyl-5-(4-fluoro-phenoxymethyl)-2-(4-fluoro-phenyl)-1-methyl-1,2-dihydro-pyrazol-3-one;
N-{4-[4-Cyclopropyl-1-(4-fluoro-phenyl)-2-methyl-5-oxo-2,5-dihydro-1H-pyrazol-3-ylmethoxy]-phenyl}-acetamide;
N-{4-[4-Cyclopropyl-1-(2-fluoro-phenyl)-2-methyl-5-oxo-2,5-dihydro-1H-pyrazol-3-ylmethoxy]-phenyl}-acetamide;
4-Cyclopropyl-5-(4-fluoro-phenoxymethyl)-2-(2-fluoro-phenyl)-1-methyl-1,2-dihydro-pyrazol-3-one;
4-Cyclopropyl-2-(4-fluoro-phenyl)-5-[2-(4-fluoro-phenyl)-ethyl]-1-methyl-1,2-dihydro-pyrazol-3-one;
4-Cyclopropyl-2-(2-fluoro-phenyl)-5-[2-(4-fluoro-phenyl)-ethyl]-1-methyl-1,2-dihydro-pyrazol-3-one;
4-Cyclopropyl-1-ethyl-5-(4-fluoro-phenoxymethyl)-2-(4-fluoro-phenyl)-1,2-dihydro-pyrazol-3-one;
5-(4-Chloro-phenoxymethyl)-4-isopropyl-1-methyl-2-phenyl-1,2-dihydro-pyrazol-3-one;
5-(2,4-Dichloro-phenoxymethyl)-4-isopropyl-1-methyl-2-phenyl-1,2-dihydro-pyrazol-3-one;
5-(4-Fluoro-phenoxymethyl)-4-isopropyl-1-methyl-2-phenyl-1,2-dihydro-pyrazol-3-one;
5-(2-Chloro-phenoxymethyl)-4-isopropyl-1-methyl-2-phenyl-1,2-dihydro-pyrazol-3-one;
5-Isopropoxymethyl-4-isopropyl-1-methyl-2-phenyl-1,2-dihydro-pyrazol-3-one;
1-Ethyl-2-phenyl-1,2,4,5,6,7-hexahydro-indazol-3-one;
1-Methyl-2-phenyl-1,4,5,6,7,8-hexahydro-2H-cycloheptapyrazol-3-one;
1-Methyl-2-(1,7,7-trimethyl-bicyclo[2.2.1]hept-2-yl)-1,2,4,5,6,7-hexahydro-indazol-3-one;
2-(2,4-Dichloro-phenyl)-1-methyl-1,2,4,5,6,7-hexahydro-indazol-3-one;
1-Methyl-2-(2-trifluoromethyl-phenyl)-1,4,5,6,7,8-hexahydro-2H-cycloheptapyrazol-3-one;
4-tert-Butyl-1,5-dimethyl-2-phenyl-1,2-dihydro-pyrazol-3-one;
4-tert-Butyl-2,5-dimethyl-1-phenyl-1,2-dihydro-pyrazol-3-one;
4-Adamantan-1-yl-5-methyl-1,2-dihydro-pyrazol-3-one;
2-Adamantan-1-yl-3-methyl-6,7-dihydro-5H-pyrazolo[1,2-a]pyrazol-1-one;
2-Adamantan-1-yl-3-methyl-5,6,7,8-tetrahydro-pyrazolo[1,2-a]pyridazin-1-one;
2-Adamantan-1-yl-3-methyl-6,7,8,9-tetrahydro-5H-pyrazolo[1,2-a][1,2]diazepin-1-one;
2-Adamantan-1-yl-3-cyclopropyl-6,7-dihydro-5H-pyrazolo[1,2-a]pyrazol-1-one;
4-Adamantan-1-yl-1,2,5-trimethyl-1,2-dihydro-pyrazol-3-one;
4-Adamantan-1-yl-1-benzyl-2,5-dimethyl-1,2-dihydro-pyrazol-3-one;
4-Adamantan-1-yl-1-isopropyl-5-methyl-1,2-dihydro-pyrazol-3-one;
4-Adamantan-1-yl-5-methyl-2-phenyl-1,2-dihydro-pyrazol-3-one;
4-Adamantan-1-yl-1,5-dimethyl-2-phenyl-1,2-dihydro-pyrazol-3-one;
4-Adamantan-1-yl-2,5-dimethyl-1-phenyl-1,2-dihydro-pyrazol-3-one;
4-Adamantan-1-yl-5-methyl-1-phenyl-1,2-dihydro-pyrazol-3-one;
4-Adamantan-1-yl-1-phenyl-1,2-dihydro-pyrazol-3-one;
4-Adamantan-1-yl-2-methyl-1-phenyl-1,2-dihydro-pyrazol-3-one;
4-Adamantan-1-yl-5-methyl-1-pyridin-2-yl-1,2-dihydro-pyrazol-3-one;
4-Adamantan-1-yl-2,5-dimethyl-1-pyridin-2-yl-1,2-dihydro-pyrazol-3-one;
4-Adamantan-1-yl-1-(4-fluoro-phenyl)-2,5-dimethyl-1,2-dihydro-pyrazol-3-one;
4-Adamantan-1-yl-2-ethyl-5-methyl-1-phenyl-1,2-dihydro-pyrazol-3-one;
3-Adamantan-1-yl-5,6,7,8-tetrahydro-4H-pyrazolo[1,5-a]azepin-2-one;
3-Adamantan-1-yl-1-methyl-5,6,7,8-tetrahydro-4H-pyrazolo[1,5-a]azepin-2-one;
3-Adamantan-1-yl-1-methyl-4,5,6,7-tetrahydro-pyrazolo[1,5-a]pyridin-2-one;
3-Adamantan-1-yl-1-ethyl-4,5,6,7-tetrahydro-pyrazolo[1,5-a]pyridin-2-one;
1,5-Dimethyl-4-(4-methyl-bicyclo[2.2.2]oct-1-yl)-2-phenyl-1,2-dihydro-pyrazol-3-one; and
2,5-Dimethyl-4-(4-methyl-bicyclo[2.2.2]oct-1-yl)-1-phenyl-1,2-dihydro-pyrazol-3-one.

16. The compound according to claim 1 selected from
4,5-Dicyclopropyl-2-(2-fluoro-phenyl)-1-methyl-1,2-dihydro-pyrazol-3-one;
2-(2-Chloro-phenyl)-4,5-dicyclopropyl-1-methyl-1,2-dihydro-pyrazol-3-one;
4,5-Dicyclopropyl-1-methyl-2-(2-trifluoromethyl-phenyl)-1,2-dihydro-pyrazol-3-one;
5-Cyclobutyl-4-cyclopropyl-1-methyl-2-(2-trifluoromethyl-phenyl)-1,2-dihydro-pyrazol-3-one;
4-Cyclopropyl-1-methyl-5-(1-methyl-cyclopropyl)-2-(2-trifluoromethyl-phenyl)-1,2-dihydro-pyrazol-3-one;
5-tert-Butyl-4-cyclopropyl-1-methyl-2-(2-trifluoromethyl-phenyl)-1,2-dihydro-pyrazol-3-one;
4-Cyclopropyl-5-(2,2-dimethyl-cyclopropyl)-1-methyl-2-(2-trifluoromethyl-phenyl)-1,2-dihydro-pyrazol-3-one;
4-Cyclopropyl-5-(4-fluoro-phenoxymethyl)-2-(2-fluoro-phenyl)-1-methyl-1,2-dihydro-pyrazol-3-one;
2-Adamantan-1-yl-3-methyl-6,7-dihydro-5H-pyrazolo[1,2-a]pyrazol-1-one;
4-Adamantan-1-yl-2,5-dimethyl-1-phenyl-1,2-dihydro-pyrazol-3-one; and
3-Adamantan-1-yl-1-methyl-4,5,6,7-tetrahydro-pyrazolo[1,5-a]pyridin-2-one.

17. The compound according to claim 1 selected from
4,5-Dicyclopropyl-2-(2,3-dichloro-phenyl)-1-methyl-1,2-dihydro-pyrazol-3-one;
1-Benzyl-4,5-dicyclopropyl-2-(2,4-difluoro-phenyl)-1,2-dihydro-pyrazol-3-one;

4,5-Dicyclopropyl-2-(2,4-difluoro-phenyl)-1-(2-fluoro-benzyl)-1,2-dihydro-pyrazol-3-one;

4,5-Dicyclopropyl-2-(2,4-difluoro-phenyl)-1-(4-fluoro-benzyl)-1,2-dihydro-pyrazol-3-one;

4,5-Dicyclopropyl-2-(3-fluoro-2-trifluoromethyl-phenyl)-1-methyl-1,2-dihydro-pyrazol-3-one;

1-Benzyl-4,5-dicyclopropyl-2-(2,5-difluoro-phenyl)-1,2-dihydro-pyrazol-3-one;

4,5-Dicyclopropyl-2-(2,5-difluoro-phenyl)-1-methyl-1,2-dihydro-pyrazol-3-one;

4,5-Dicyclopropyl-2-(2-methanesulfonyl-phenyl)-1-methyl-1,2-dihydro-pyrazol-3-one;

4,5-Dicyclopropyl-1-methyl-2-(2-trifluoromethoxy-phenyl)-1,2-dihydro-pyrazol-3-one;

4,5-Dicyclopropyl-1-(2,4-difluoro-benzyl)-2-(2,5-difluoro-phenyl)-1,2-dihydro-pyrazol-3-one;

4,5-Dicyclopropyl-2-(2,4-difluoro-phenyl)-1-(3,3,3-trifluoro-propyl)-1,2-dihydro-pyrazol-3-one;

4,5-Dicyclopropyl-2-(2,4-difluoro-phenyl)-1-pyridin-2-ylmethyl-1,2-dihydro-pyrazol-3-one;

4,5-Dicyclopropyl-1-methyl-2-o-tolyl-1,2-dihydro-pyrazol-3-one;

2-Benzothiazol-2-yl-4,5-dicyclopropyl-1-methyl-1,2-dihydro-pyrazol-3-one;

4,5-Dicyclopropyl-2-(2,3-dimethyl-phenyl)-1-methyl-1,2-dihydro-pyrazol-3-one;

4,5-Dicyclopropyl-2-(2-ethyl-phenyl)-1-methyl-1,2-dihydro-pyrazol-3-one;

4,5-Dicyclopropyl-2-(2,5-dichloro-phenyl)-1-methyl-1,2-dihydro-pyrazol-3-one;

4,5-Dicyclopropyl-2-(2-fluoro-3-methyl-6-trifluoromethyl-phenyl)-1-methyl-1,2-dihydro-pyrazol-3-one;

4-Cyclopropyl-1-methyl-5-trifluoromethyl-2-(2-trifluoromethyl-phenyl)-1,2-dihydro-pyrazol-3-one;

4-Cyclopropyl-5-(2,2-difluoro-cyclopropyl)-1-methyl-2-(2-trifluoromethyl-phenyl)-1,2-dihydro-pyrazol-3-one;

4-Cyclopropyl-5-(3,3-difluoro-cyclobutyl)-1-methyl-2-(2-trifluoromethyl-phenyl)-1,2-dihydro-pyrazol-3-one;

4,5-Dicyclopropyl-2-(2,4-difluoro-phenyl)-1-(2,2,2-trifluoro-ethyl)-1,2-dihydro-pyrazol-3-one; and 4,5-Dicyclopropyl-2-(2,2-dimethyl-propyl)-1-methyl-1,2-dihydro-pyrazol-3-one.

18. A process for the preparation of a compound of formula (I)

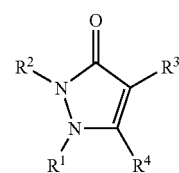

comprising one of the following reactions:

a) reacting a compound according to formula

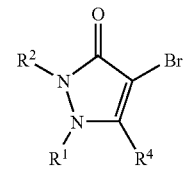

in the presence of a compound of formula

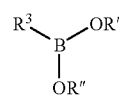

in order to obtain a compound of formula I; or b) reacting a compound of formula

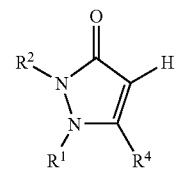

in the presence of $R^3$—OH in order to obtain a compound of formula I;

wherein $R^1$ to $R^4$ are defined as in claim 1 and R' and R" are hydrogen or R' and R" form together —$(CH_2)_2$— or —$(CH_2)_3$—.

19. A pharmaceutical composition, comprising a therapeutically effective amount of a compound according to claim 1 and a therapeutically inert carrier.

* * * * *